(12) United States Patent
Lee et al.

(10) Patent No.: US 7,989,634 B2
(45) Date of Patent: Aug. 2, 2011

(54) MELANOCORTIN RECEPTOR AGONISTS

(75) Inventors: Koo Lee, Daejeon (KR); Heui-Sul Park, Daejeon (KR); In-Ae Ahn, Daejeon (KR); Hyun-Ju Yoo, Daejeon (KR); Jong-Yup Kim, Daejeon (KR); Deog-Young Choi, Daejeon (KR); Hyeon-Joo Yim, Daejeon (KR); Kyung-Ha Chung, Daejeon (KR); Dong-Sup Shim, Daejeon (KR); Sang-Kyun Lee, Daejeon (KR); Yutaka Kondoh, Daejeon (KR); Ryoji Hirabayashi, Daejeon (KR); Shugo Honda, Daejeon (KR); Hidetaka Kaku, Daejeon (KR); Jun-ichi Shishikura, Daejeon (KR); Hiroyuki Ito, Daejeon (KR); Takeshi Kurama, Daejeon (KR)

(73) Assignees: LG Life Sciences Ltd., Seoul (KR); Yamanouchi Pharmaceutical Co., Ltd., Tokyo (JP)

( * ) Notice: Subject to any disclaimer, the term of this patent is extended or adjusted under 35 U.S.C. 154(b) by 1220 days.

(21) Appl. No.: 10/579,042

(22) PCT Filed: Nov. 12, 2004

(86) PCT No.: PCT/KR2004/002929
§ 371 (c)(1),
(2), (4) Date: Jan. 30, 2007

(87) PCT Pub. No.: WO2005/047251
PCT Pub. Date: May 26, 2005

(65) Prior Publication Data
US 2007/0129346 A1   Jun. 7, 2007

(30) Foreign Application Priority Data

Nov. 12, 2003 (KR) .................. 10-2003-0079799
Aug. 20, 2004 (KR) .................. 10-2004-0065820

(51) Int. Cl.
*C07D 213/46* (2006.01)
*C07D 211/70* (2006.01)
*C07D 401/00* (2006.01)
(52) U.S. Cl. ............. 546/314; 546/328; 546/268.1
(58) Field of Classification Search .............. 546/314, 546/328, 268.1
See application file for complete search history.

(56) References Cited

U.S. PATENT DOCUMENTS

| 6,495,715 | B2 * | 12/2002 | Hu et al. ............. 562/471 |
| 6,750,348 | B1 * | 6/2004 | Bridger et al. ............. 546/139 |

FOREIGN PATENT DOCUMENTS

| WO | WO 99/07689 A1 | 2/1999 |
| WO | WO-00/74679 A1 | 12/2000 |
| WO | WO-01/70708 A1 | 9/2001 |
| WO | WO-02/059107 A1 | 8/2002 |
| WO | WO-02/068388 A2 | 9/2002 |
| WO | WO-03/007949 A1 | 1/2003 |

OTHER PUBLICATIONS

Alan R. Jacobson, et al, Minimum-Structure Enkephalin Analogues Incorporating L-Tyrosine, D(orL)-Phenylalanine, and a Diamine Spacer, 32 J Med. Chem. 1708 (1989).*
George Patani and Edmond LaVoie, Bioisosterism: A Rational Approach in Drug Design, 96 Chem. Rev. 3147 (1996).*

* cited by examiner

*Primary Examiner* — Jeffrey S Lundgren
*Assistant Examiner* — Sean Basquill
(74) *Attorney, Agent, or Firm* — Birch, Stewart, Kolasch & Birch, LLP

(57) ABSTRACT

The present invention relates a compound of formula 1, and pharmaceutically acceptable salt, hydrate, solvate, or isomer thereof effective as agonist of melanocortin receptor, and an agonistic composition of melanocortin receptor comprising the same as active ingredient.

7 Claims, No Drawings

MELANOCORTIN RECEPTOR AGONISTS

TECHNICAL FIELD

The present invention relates to a compound of the following formula 1, pharmaceutically acceptable salt, hydrate, solvate, and isomer thereof effective as an agonist for melanocortin receptor.

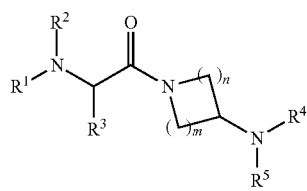

(I)

in which
$R^1$, $R^2$, $R^3$, $R^4$, $R^5$, n and m are defined as described below.

BACKGROUND ART

Five subtypes of receptors have been cloned and characterized in the melanocortin family. These G-protein coupled receptors (GPCR) stimulate the cAMP signal transduction pathway in many different tissues, mediating a wide range of physiological functions. Melanocortin 1 receptor (MC1R) is mainly expressed in melanocytes, monocytes, and mast cells, to mediate pigmentation of the hair and skin and to block inflammation. MC2R is expressed in adipocytes and adrenal cells, to mediate steroidogenesis in the adrenal gland. MC3R is present in the brain, hyphothalamus, heart, gut, and placenta, and has been associated with energy homeostasis and inflammation. MC4R is uniquely expressed in the brain, and controls feeding behavior, energy homeostasis, and erectile function. MC4R knock-out mice revealed the phenotype of hyperphasia and obesity. MC5R is found in a wide range of tissues and is considered to play a role for the exocrine gland system.

With a plethora of physiological functions of melanocortin receptors, a large number of compounds have been designed and synthesized in search for potent agonists and antagonists.

Early examples are synthetic peptides and peptide analogues that have been identified on the basis of endogenous agonist such as αMSH. These peptide agonists have been used to characterize the function of these receptors. NDP-αMSH is a highly potent and nonselective agonist of MC1R, 3R, 4R and 5R, and has been reported to attenuate food intake and body weight gain in rat models. A cyclic heptapeptide MT-II is an agonist with a similar non-selective profile, and its therapeutic use has been proven in clinical trials for the treatment of erectile dysfunction. HP-228, a peptide analogue with similar affinity for all four receptors, was in clinical trials for the treatment of pain and inflammation associated with surgery.

Several small molecule agonists for the melanocortin receptors have been discovered to have significant activity in drug trials to search MC4R agonists for the treatment of obesity, sexual dysfunction or inflamation. For example, the Merck research group has discovered a series of potent and selective MC4R agonists, one of which demonstrated significant effect for augmenting erectile response in mice (*J. Med. Chem.* 2002, 45, 4849). The Chiron research group has discovered a series of guanidine compounds as agonists that have hyphophasic activity and thus anti-obesity effect in the ob/ob mouse model (WO 02/18327). On the other hand, the Bristol-Myers Squibb group has discovered a highly potent selective MC 1R agonist, which showed efficacy in an acute mouse model of inflammation (*J. Med. Chem.* 2003, 46, 1123).

In view of the unresolved deficiencies of the various pharmaceutical compounds as discussed above, there is continuing need in the art for small molecule MCR agonists and pharmacological compositions that have improved pharmacological profiles. It is, therefore, an object of the present invention to provide novel compounds that are useful for the treatment of obesity, diabetes, sexual dysfunction, and inflammation.

Specifically, the present invention provides a compound of formula 1 having agonistic effect against MCRs, in particular selective agonistic effect against MCR4, and pharmaceutically acceptable salt, hydrate, solvate, and isomer thereof.

Another object of the present invention is to provide a melanocortin receptor agonistic composition comprising the compound of formula 1, and pharmaceutically acceptable salt, hydrate, solvate, and isomer thereof, as active ingredients, together with pharmaceutically acceptable carrier.

In particular, the composition according to the present invention has potent effect for the prevention and treatment of diabetes, erectile dysfunction, obesity, and inflammation.

DISCLOSURE OF THE INVENTION

The present invention relates to a compound of the following formula 1, and pharmaceutically acceptable salt, hydrate, solvate, and isomer thereof.

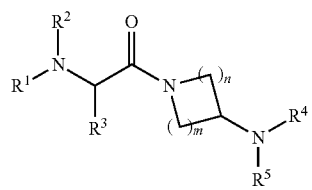

1 in which
m and n each independently represents 1 or 2,
$R^1$ reperesents
 hydrogen,
 —$(CH_2)_p$—$R^6$,
 —$(CH_2)_p$—CO—$(CH_2)_p$—$R^6$,
 —$(CH_2)_p$—CO—$(CH_2)_p$—CH($R^6$)($R^{10}$), or
 —$(CH_2)_p$—$SO_2$—$(CH_2)_p$—$R^6$,
 wherein
 p independently represent 0, 1, 2, or 3,
 $R^6$ represents $C_1$-$C_{10}$-alkyl, $C_1$-$C_8$-alkoxy, $C_3$-$C_8$-cycloalkyl, heterocycle, aryl, heteroaryl, amino, or hydroxy, in each of which is unsubstituted or mono- or poly-substituted by one or more substituents selected from the group consisting of $C_1$-$C_{10}$-alkyl, $C_1$-$C_{10}$-dialkyl, $C_3$-$C_{13}$-cycloalkyl, $C_3$-$C_{13}$-dicycloalkyl, $C_3$-$C_{13}$-tricycloalkyl, perhalo-$C_1$-$C_8$-alkyl, aryl, heteroaryl, heterocycle, hydroxy, $C_1$-$C_8$-alkoxy, $C_1$-$C_8$-alkoxy-$C_1$-$C_8$-alkoxy, trifluoromethoxy, aryl-$C_1$-$C_8$-alkyloxy, aryloxy, oxo, mercapto, $C_1$-$C_8$-alkylcarbonyl, $C_1$-$C_8$-alkoxycarbonyl, $C_1$-$C_8$-alkylsulfonyl, arylsulfonyl, $C_1$-$C_8$-alkylthio, arylthio, cyano, formyl, halogen, carbonyl, thiocarbonyl, $C_3$-$C_8$-cycloalkylcarbonyl, arylcarbonyl, ar-$C_1$-$C_8$-alkyl, ar-$C_1$-$C_8$-alkylcarbonyl, ar-$C_1$-$C_8$-alkylsulfonyl, O-carbamoyl, N-carbamoyl, O-thiocarbamoyl, N-thiocarbamoyl, carbamoyl, $C_1$-$C_8$-alkylcarbamoyl, di($C_1$-$C_8$- alkyl)carbamoyl, O-sulfoneamido, N-sulfonamido, carboxy, isocyanato, thiocyanato, isothiocyanato, nitro, trihalomethanesulfonyl, amino, $C_1$-$C_6$-alkylamino, di($C_1$-$C_6$-alkyl)amino, and protective derivatives thereof, $R^{10}$ represents heterocycle, or represents amino or hydroxy, in each of which is unsubstituted or mono- or poly-substituted by the substituents selected from the group consisting of $R^7$, wherein, $R^7$ represents halogen, amino, $C_1$-$C_6$-alkylamino, di($C_1$-$C_6$-alkyl)amino, hydroxy, $C_1$-$C_8$-alkoxy, trifluoromethoxy, $C_1$-$C_6$-alkylcarbonyl, carboxy, $C_1$-$C_8$-alkyl, mercapto, $C_1$-$C_{10}$-alkylthio, phenoxy, $C_1$-$C_8$-alkoxycarbonyl, arylcarbonyl, carbamoyl, $C_1$-$C_6$-alkylsulfonyl, arylsulfonyl, cyano or oxo, $R^6$ and $R^{10}$ may form 5- or 6-membered single ring together with the atoms to which they attached, hydrogen atom in —$(CH_2)_p$— group can be replaced by $R^6$, $R^1$ represents
hydrogen,
$C_1$-$C_8$-alkyl which is unsubstituted or mono- or poly-substituted by the substituents selected from the group consisting of $R^7$,
$C_3$-$C_7$-cycloalkyl, or
—CO—$(CH_2)_p$—$R^6$, $R^1$ and $R^2$ together with the atoms to which they attached, may form 4- or 8-membered single ring or two ring which can contain heteroatom selected from the group consisting of O, S and N—($C_1$-$C_4$-alkyl), $R^3$ and $R^4$ each independently represents
hydrogen,
$C_1$-$C_8$-alkyl,
—$(CH_2)_p$—$C_3$-$C_8$-cycloalkyl,
—$(CH_2)_p$—$C_6$-$C_{10}$-aryl,
—$(CH_2)_p$-heteroaryl, or
—$(CH_2)_p$-heterocycle, wherein, alkyl, cycloalkyl, heterocycle, aryl, or heteroaryl, in each of which is unsubstituted or mono- or poly-substituted by the substituents selected from the group consisting of $R^7$, $R^5$ represents
hydrogen,
$C_1$-$C_6$-alkyl,
—$(CH_2)_p$—CO—$R^8$,
—$(CH_2)_p$—C(O)N($R^8$)($R^9$),
—$(CH_2)_p$—C(S)N($R^8$)($R^9$),
—$(CH_2)_p$—$SO_2$—N($R^8$)($R^9$), or
—$(CH_2)_p$—$SO_2$—$R^8$, wherein, $R^8$ and $R^9$ each independently represents
hydrogen,
$C_1$-$C_8$-alkyl,
$C_1$-$C_6$-alkoxy,
$C_1$-$C_6$-alkylthio,
$C_3$-$C_7$-cycloalkyl,
$C_3$-$C_7$-cycloalkenyl,
heterocycle,
aryl, or
heteroaryl, wherein
alkyl, cycloalkyl, or aryl is unsubstituted or mono- or poly-substituted by the substituents selected from the group consisting of $R^7$, $C_3$-$C_8$-cycloalkyl, heterocycle, hydroxy-$C_1$-$C_8$-alkyl, halogen-$C_1$-$C_8$-alkyl, $C_1$-$C_8$-alkoxy-$C_1$-$C_8$-alkyl, amino-$C_1$-$C_8$-alkyl, $C_3$-$C_8$-cycloalkyloxy, ar-$C_1$-$C_8$-alkyloxy, aryloxy, arylthio, formyl, $C_1$-$C_8$-alkylcarbamoyl, di($C_1$-$C_8$-alkyl)carbamoyl, $C_1$-$C_8$-alkylcarbonyloxy, $C_1$-$C_8$-alkoxy-$C_1$-$C_8$-alkoxy, $C_3$-$C_8$-cycloalkylcarbonyl, ar-$C_1$-$C_8$-alkylcarbonyl, $C_2$-$C_8$-alkanoyloxy, $C_3$-$C_8$-cycloalkylcarbonyloxy, arylcarbonyloxy which is unsubstituted or substituted by halogen, ar-$C_1$-$C_8$-alkylcarbonyloxy, $C_1$-$C_8$-alkoxyimino, ar-$C_1$-$C_8$-alkylsulfonyl, and $C_1$-$C_8$-alkylsulfonyloxy, heterocycle, cycloalkenyl, or heteroaryl is unsubstituted or mono- or poly-substituted by the substituents selected from the group consisting of $R^7$, and hydroxy-$C_1$-$C_8$-alkyl, $R^4$ and $R^5$ together with the atoms to which they attached, may form 4- or 8-membered single ring or two ring which can contain heteroatom selected from the group consisting of O, S and N—($C_1$-$C_4$-alkyl).

In the radical definitions of the compound of formula (1) according to the present invention, the term "alkyl" means straight-chain or branched hydrocarbon radical when used alone or in combination with hetroatoms such "alkyloxy."

The term "cycloalkyl" represents unsaturated aliphatic ring including cyclohexyl.

The term "aryl" represents 6- to 10-membered aromatic group including phenyl, naphthyl, etc.

The term "heteroaryl" includes 1 to 2 heteroatom(s) from the group consisting of nitrogen atom, oxygen atom, and sulfur atom, and represents aromatic 3- to 6-membered ring which can be fused with benzo or $C_3$-$C_8$-cycloalkyl. Examples of monocyclic heteroaryl are, but are not limited to, thiazole, oxazole, thiophene, furane, pyrrole, imidazole, isoxazole, pyrazole, triazole, thiadiazole, tetrazole, oxadiazole, pyridine, pyridazine, pyrimnidine, pyrazine, and similar group to them. Examples of acyclic heteroaryl are, but are not limited to, indole, benzothiophene, benzofuran, benzimidazole, benzoxazole, benzisoxazole, benzthiazole, benzthiadiazole, benztriazole, quinoline, isoquinoline, purine, furopyridine, and similar group to them.

The term "heterocycle" includes 1 to 2 heteroatom(s) from the group consisting of nitrogen atom, oxygen atom, and sulfur atom, and represents 4- to 8-membered ring which can be fused with benzo or $C_3$-$C_8$-cycloalkyl, and which is saturated or has 1 or 2 of double bond. Its examples are, but are not limited to, piperidine, morpholine, thiamorpholine, pyrrolidine, imidazolidine, tetrahydrofuran, piperazine, and similar group to them.

Preferred compounds among the compounds of formula 1 above are those
wherein
i) $R^1$ represents hydrogen, —$(CH_2)_p$—$R^6$, —$(CH_2)_p$—CO—$R^6$, —CO—$(CH_2)_p$—$R^6$, —$(CH_2)_p$—CO—$(CH_2)_p$—CH($R^6$)($R^{10}$), or —$SO_2$—$(CH_2)_p$—$R^6$, $R^6$ represents $C_1$-$C_{10}$-alkyl, $C_1$-$C_8$-cycloalkyl, heterocycle, aryl, or heteroaryl, or represent amino or hydroxy, hydrogen atom in —$(CH_2)_p$— group can be replaced by $R^6$, wherein $C_1$-$C_{10}$-alkyl, $C_1$-$C_8$-cycloalkyl, heterocycle, aryl, or heteroaryl is unsubstituted or mono- or poly-substituted by the substituents selected from the group consisting of $R^7$, amino or hydroxy is unsubstituted or mono- or di-substituted by the substituents selected from the group consisting of $C_1$-$C_{10}$-alkyl, ar-$C_1$-$C_8$-alkyl, $C_3$-$C_8$-cycloalkyl, $C_2$-$C_8$-alkylcarbonyl, $C_3$-$C_8$-cycloalkylcarbonyl, arylcarbonyl, ar-$C_1$-$C_8$-alkylcarbonyl, $C_1$-$C_8$-alkoxycarbonyl, carbamoyl, di($C_1$-$C_8$-alkyl)carbamoyl, $C_1$-$C_8$-alkylsulfonyl, arylsulfonyl, and ar-$C_1$-$C_8$-alkylsulfonyl, $R^{10}$ is defined as the above description, $R^6$ and $R^{10}$ may form 5- or 6-membered single ring together with the atoms to which they attached, preferably, $R^1$ represents hydrogen, —$(CH_2)_p$—$R^6$, —$(CH_2)_p$—CO—$R^6$, —CO—$(CH_2)_p$—$R^6$ or —$(CH_2)_p$—CO—$(CH_2)_p$—CH($R^6$)($R^{10}$), more preferably, $R^1$ represents hydrogen, —$R^6$ or —CO—CH($R^6$)($R^{10}$), $R^{10}$ represents heterocycle, or represents amino or hydroxy, in each of which is unsubstituted or mono- or polysubstituted by the substituents selected from the group consisting of $R^7$, $R^6$ and $R^{10}$ may form 5- or 6-membered single ring together with the atoms to which they attached, ii) $R^2$ represents hydrogen or $C_1$-$C_6$-alkyl, iii) $R^3$ represents $C_1$-$C_8$-alkyl, —$(CH_2)_p$—$C_3$-$C_7$-cycloalkyl, —$(CH_2)_p$-phenyl, or —$(CH_2)_p$-heteroaryl, in each of which is unsubstituted or mono- to tri-substituted by substituents from the group consisting of $R^7$, preferably, $R^3$ represents —$CH_2$-cyclohexyl or —$CH_2$-phenyl, in each of which is unsubstituted or mono- to tri-substituted by substituents from the group consisting of halogen, cyano, hydroxy, $C_1$-$C_8$-alkoxy, trifluoromethoxy and $C_1$-$C_4$-alkyl, more preferably, $R^3$ represents —$CH_2$-phenyl, in which is unsubstituted or mono- to tri-substituted by substituents from the group consisting of chloro, bromo, cyano, hydroxy, methoxy and metyhl, iv) $R^4$ represents $C_1$-$C_8$-alkyl, or represent $C_3$-$C_8$-cycloalkyl, phenyl, heteroaryl, or heterocycle, in each of which is unsubstituted or mono- to tri-substituted by substituents from the group consisting of $R^7$, preferably, $R^4$ represents $C_3$-$C_8$-cycloalkyl or phenyl, more preferably, $R^4$ represents cyclohexyl, cylcoheptyl or cylcopentyl, in each of which is unsubstituted or mono- to tri-substituted by substituents from the group consisting of methyl, ethyl, t-butyl, hydroxy and oxo, or represent phenyl unsubstituted or mono- to tri-substituted by substituents from the group consisting of fluoro, chloro, methoxy and methyl, v) $R^5$ represents hydrogen, $C_1$-$C_6$-alkyl, —$(CH_2)_p$—CO—$R^8$, —$(CH_2)_p$—C(O)N($R^5$)$^9$), or —$(CH_2)_p$—SO$_2$—$R^8$, preferably, $R^5$ represents —CO—$R^8$ or —C(O)N($R^8$)($R^9$), more preferably, $R^8$ and $R^9$ each independently represents hydrogen, methoxy, amino, $C_1$-$C_8$-alkyl, $C_3$-$C_6$-cycloalkyl, $C_5$-$C_6$-cycloalkenyl, heterocycle, or phenyl, wherein, $C_1$-$C_8$-alkyl or $C_3$-$C_6$-cycloalkyl is unsubstituted or mono-substituted by the substituents selected from the group consisting of methyl, hydroxy, amino, $C_1$-$C_4$-alkoxy, phenoxy, benzyloxy, fluoro, phenylsulfoxy, acetyl, methoxymethylalkoxy, carboxy, formyl, methoxycarbonyl, dimethylcarbamoyl, carboxy, phenylcarbonyloxy, methoxycarbonyl, difluorophenylcarbonyloxy, dimethylphenylcarbonyloxy, cyclohexylcarbonyloxy, arylcarbonyloxy, and oxo, $C_5$-$C_6$-cycloalkenyl represents cyclopentyl or cyclohexyl substituted by hydroxy or amino, heterocycle or phenyl is unsubstituted or mono- or polysubstituted by the substituents selected from the group consisting of hydroxy, methyl, amino, nitrobenzenesulfonyl, and oxo.

vi) $R^1$ represents hydrogen, —$R^6$ or —CO—CH($R^6$)($R^{10}$), $R^{10}$ represents heterocycle, or represents-amino or hydroxy, in each of which is unsubstituted or mono- or polysubstituted by the substituents selected from the group consisting of $R^7$, $R^6$ and $R^{10}$ may form 5- or 6-membered single ring together with the atoms to which they attached, $R^3$ represents —$CH_2$-phenyl, in which is unsubstituted or mono- to tri-substituted by substituents from the group consisting of chloro, bromo, cyano, hydroxy, methoxy and metyhl, $R^4$ represents cyclohexyl, cylcoheptyl or cylcopentyl, in each of which is unsubstituted or mono- to tri-substituted by substituents from the group consisting of methyl, ethyl, t-butyl, hydroxy and oxo, or represent phenyl unsubstituted or mono- to tri-substituted by substituents from the group consisting of fluoro, chloro, methoxy and methyl, $R^5$ represents —CO—$R^8$ or —C(O)N($R^6$)($R^9$), $R^8$ and $R^9$ each independently represents hydrogen, methoxy, amino, $C_1$-$C_8$-alkyl, $C_3$-$C_6$-cycloalkyl, $C_5$-$C_6$-cycloalkenyl, heterocycle, or phenyl, wherein, $C_1$-$C_8$-alkyl or $C_3$-$C_6$-cycloalkyl is unsubstituted or mono-substituted by the substituents selected from the group consisting of methyl, hydroxy, amino, $C_1$-$C_4$-alkoxy, phenoxy, benzyloxy, fluoro, phenylsulfoxy, acetyl, methoxymethylalkoxy, carboxy, formyl, methoxycarbonyl, dimethylcarbamoyl, carboxy, phenylcarbonyloxy, methoxycarbonyl, difluorophenylcarbonyloxy, dimethylphenylcarbonyloxy, cyclohexylcarbonyloxy, arylcarbonyloxy, and oxo, $C_5$-$C_6$-cycloalkenyl represents cyclopentyl or cyclohexyl substituted by hydroxy or amino, heterocycle or phenyl is unsubstituted or mono- or polysubstituted by the substituents selected from the group consisting of hydroxy, methyl, amino, nitrobenzenesulfonyl, and oxo.

Representative compounds of formula 1 according to the present invention include the compounds listed in the following Table 1.

TABLE 1

| $R^1$ | $R^2$ | $R^3$ | *1 | n | m | $R^4$ | *2 | $R^5$ |
|---|---|---|---|---|---|---|---|---|
| H | H | 4-Cl-Bn | R | 2 | 1 | c-Hex | S | C(O)CH(Me)$_2$ |
| H | H | 4-Cl-Bn | R | 2 | 1 | c-Hex | S | C(O)C(Me)$_3$ |
| H | H | 4-Cl-Bn | R | 2 | 1 | c-Hex | S | C(O)OMe |
| H | H | 4-Cl-Bn | R | 2 | 1 | c-Hex | S | C(O)N(Me)$_2$ |
| H | H | 4-Cl-Bn | R | 2 | 1 | c-Hex | S | SO$_2$Me |
| H | H | 4-Cl-Bn | R | 2 | 1 | c-Hex | S | CH$_2$C(O)OMe |
| H | H | 4-Cl-Bn | R | 2 | 1 | c-Hex | S | SO$_2$NH$_2$ |
| H | H | 4-Cl-Bn | R | 2 | 1 | c-Hex | S | Gly |
| H | H | 4-Cl-Bn | R | 2 | 1 | c-Hex | S | CH$_2$C(O)N(Me)$_2$ |
| H | H | 4-Cl-Bn | R | 2 | 1 | c-Hex | S | CH$_2$SO$_2$Me |
| H | H | 4-Cl-Bn | R | 2 | 1 | c-Hex | R | C(O)CH(Me)$_2$ |
| H | H | 4-Cl-Bn | R | 2 | 1 | c-Hex | R | C(O)C(Me)$_3$ |
| H | H | 4-Cl-Bn | R | 2 | 1 | c-Hex | S | C(O)[(R)—CH(Me)CH$_2$OH] |
| H | H | 4-Cl-Bn | R | 2 | 1 | c-Hex | S | C(O)C(Me)$_2$CH$_2$OH |
| H | H | 4-Cl-Bn | R | 2 | 1 | c-Hex | S | C(O)C(Me)$_2$OH |
| H | H | 4-Cl-Bn | R | 2 | 1 | c-Hex | S | C(O)C(Me)$_2$(CH$_2$)$_2$—OH |
| H | H | 4-Cl-Bn | R | 2 | 1 | c-Hex | S | C(O)C(Me)—(CH$_2$OH)$_2$ |

TABLE 1-continued

| R¹ | R² | R³ | *1 | n | m | R⁴ | *2 | R⁵ |
|---|---|---|---|---|---|---|---|---|
| H | H | 4-Cl-Bn | R | 2 | 1 | c-Hex | R | C(O)C(Me)₂CH₂OH |
| H | H | 4-Cl-Bn | R | 2 | 1 | c-Hex | S | C(O)C(Me)₂CH₂OMe |
| H | H | 4-Cl-Bn | R | 2 | 1 | c-Hex | S | C(O)C(Me)₂CH₂OBn |
| H | H | 4-Cl-Bn | R | 2 | 1 | c-Hex | S | C(O)C(—(CH₂)₄—)CH₂OH |
| H | H | 4-Cl-Bn | R | 2 | 1 | c-Hex | S | C(O)C(Me)₂(CH₂)₃O-(2,4-diMe—Ph) |
| H | H | 4-Cl-Bn | R | 2 | 1 | c-Hex | S | C(O)CH(Me)CH₂OAc |
| H | H | 4-Cl-Bn | R | 2 | 1 | c-Hex | S | C(O)C[—(CH₂)₂—]CH₂OH |
| H | H | 4-Cl-Bn | R | 2 | 1 | c-Hex | S | C(O)NH(Pr) |
| H | H | 4-Cl-Bn | R | 2 | 1 | c-Hex | S | C(O)NHEt |
| H | H | 4-Cl-Bn | R | 2 | 1 | c-Hex | S | C(O)NH(Bu) |
| H | H | 4-Cl-Bn | R | 2 | 1 | c-Hex | S | C(O)(3-HO—Ph) |
| H | H | 4-Cl-Bn | R | 2 | 1 | c-Hex | S | C(O)(4-HO—Ph) |
| H | H | 4-Cl-Bn | R | 2 | 1 | c-Hex | S | C(O)[2-(CH₂OH)-1-(c-penten)-1-yl] |
| H | H | 4-Cl-Bn | R | 2 | 1 | c-Hex | S | C(O)[2-(CH₂OH)-1-(c-hexen)-1-yl] |
| H | H | 4-Cl-Bn | R | 2 | 1 | c-Hex | S | C(O)[1-Nos-Pid-4-yl] |
| H | H | 4-Cl-Bn | R | 2 | 1 | c-Hex | S | C(O)[Pid-4-yl] |
| H | H | 4-Cl-Bn | R | 2 | 1 | c-Pen | S | C(O)CH(Me)₂ |
| H | H | 4-Cl-Bn | R | 2 | 1 | c-Hep | S | C(O)CH(Me)₂ |
| H | H | 4-Cl-Bn | R | 2 | 1 | i-Pr | S | C(O)CH(Me)₂ |
| H | H | 4-Cl-Bn | R | 2 | 1 | c-Hex-CH₂ | S | C(O)CH(Me)₂ |
| H | H | 4-Cl-Bn | R | 2 | 1 | 4,4-diMe-c-Hex | S | C(O)CH(Me)₂ |
| H | H | 4-Cl-Bn | R | 2 | 1 | c-Pen | R | C(O)CH(Me)₂ |
| H | H | 4-Cl-Bn | S | 2 | 1 | c-Hex | S | C(O)CH(Me)₂ |
| H | H | Bn | R | 2 | 1 | c-Hex | S | C(O)CH(Me)₂ |
| H | H | Bn | R | 2 | 1 | c-Hex | S | C(O)C(Me)₂CH₂OH |
| H | H | 4-Br-Bn | R | 2 | 1 | c-Hex | S | C(O)CH(Me)₂ |
| H | H | 4-Br-Bn | R | 2 | 1 | c-Hex | S | C(O)C(Me)₂CH₂OH |
| H | H | 4-MeO-Bn | R | 2 | 1 | c-Hex | S | C(O)CH(Me)₂ |
| H | H | 4-MeO-Bn | R | 2 | 1 | c-Hex | S | C(O)C(Me)₂CH₂OH |
| H | H | 3,4-diCl-Bn | R | 2 | 1 | c-Hex | S | C(O)CH(Me)₂ |
| H | H | 4-F-Bn | R | 2 | 1 | c-Hex | S | C(O)CH(Me)₂ |
| H | H | 4-F-Bn | R | 2 | 1 | c-Hex | S | C(O)C(Me)₂CH₂OH |
| H | H | 4-Me-Bn | R | 2 | 1 | c-Hex | S | C(O)C(Me)₂CH₂OH |
| H | H | 4-HO-Bn | R | 2 | 1 | c-Hex | S | C(O)CH(Me)₂ |
| H | H | (c-Hex)-CH₂ | R | 2 | 1 | c-Hex | S | C(O)CH(Me)₂ |
| H | H | (indol-2-yl)-CH₂ | R | 2 | 1 | c-Hex | S | C(O)CH(Me)₂ |
| H | H | i-Bu | R | 2 | 1 | c-Hex | S | C(O)CH(Me)₂ |
| H | H | NH₂C(O)CH₂— | R | 2 | 1 | c-Hex | S | C(O)CH(Me)₂ |
| H | H | 4-Cl-Bn | R | 2 | 1 | 2,3-diF—Ph | S | C(O)CH(Me)₂ |
| H | H | 4-Cl-Bn | R | 2 | 1 | 2,4-diF—Ph | S | C(O)CH(Me)₂ |
| H | H | 4-Cl-Bn | R | 2 | 1 | 2,3-diF—Ph | R | C(O)CH(Me)₂ |
| H | H | 4-Cl-Bn | R | 2 | 1 | 2,4-diF—Ph | R | C(O)CH(Me)₂ |
| H | H | 4-Cl-Bn | R | 2 | 1 | c-Hex | S | C(O)NH(CH₂)₄NH₂ |
| H | H | 4-Cl-Bn | R | 2 | 1 | c-Hex | S | C(O)NH(CH₂)₃NH₂ |
| H | H | 4-Cl-Bn | R | 2 | 1 | c-Hex | S | C(O)NH(CH₂)₂NH₂ |
| H | H | 4-Cl-Bn | R | 2 | 1 | c-Hex | S | C(O)NH(CH₂)₂OH |
| H | H | 4-Cl-Bn | R | 2 | 1 | c-Hex | S | C(O)NH(CH₂)₂OMe |
| H | H | 4-Cl-Bn | R | 2 | 1 | c-Hex | S | C(O)[(3S)-3-(OH)-Pyd-1-yl] |
| H | H | 4-Cl-Bn | R | 2 | 1 | c-Hex | S | C(O)[(2S)-2-(HOCH₂)-Pyd-1-yl] |
| H | H | 4-Cl-Bn | R | 2 | 1 | c-Hex | R | C(O)C(Me)₂CH₂OH |
| H | H | 4-Cl-Bn | R | 2 | 1 | c-Hex | R | C(O)C(Me)CH₂OH |
| H | H | 4-Cl-Bn | R | 2 | 1 | 2,3-diF—Ph | S | C(O)C(Me)₂CH₂OH |
| H | H | 4-Cl-Bn | R | 2 | 1 | 3,5-diMe—Ph | R,S | C(O)C(Me)₂CH₂OH |
| H | H | 4-Cl-Bn | R | 2 | 1 | 2,3-diF-ph | R,S | C(O)C(Me)₂CH₂OH |
| H | H | 4-Cl-Bn | R | 2 | 1 | 4-Me—Ph | R,S | C(O)C(Me)₂CH₂OH |
| H | H | 4-Cl-Bn | R | 2 | 1 | 4-trans-Me-c-Hex | S | C(O)C(Me)₂CH₂OH |
| H | H | 4-Cl-Bn | R | 2 | 1 | 4-cis-Me-c-Hex | S | C(O)C(Me)₂CH₂OH |
| H | H | 4-Cl-Bn | R | 2 | 1 | 4,4-diMe-c-Hex | S | C(O)C(Me)₂CH₂OH |
| H | H | 4-Cl-Bn | R | 2 | 1 | 4-t-Bu-c-Hex | S | C(O)C(Me)₂CH₂OH |
| H | H | 4-Cl-Bn | R | 2 | 1 | 4,4-diF-c-Hex | S | C(O)C(Me)₂CH₂OH |
| H | H | 4-Cl-Bn | R | 2 | 1 | 4-F-c-Hex | S | C(O)C(Me)₂CH₂OH |
| H | H | 4-Cl-Bn | R | 2 | 1 | 4-trans-Et-c-Hex | S | C(O)C(Me)₂CH₂OH |
| H | H | 4-Cl-Bn | R | 2 | 1 | 4-cis-Et-c-Hex | S | C(O)C(Me)₂CH₂OH |
| H | H | 4-Cl-Bn | R | 2 | 1 | 4-oxo-c-Hex | S | C(O)C(Me)₂CH₂OH |
| H | H | 4-Cl-Bn | R | 2 | 1 | 4-OH-c-Hex | S | C(O)C(Me)₂CH₂OH |
| H | H | 4-Cl-Bn | R | 2 | 1 | Spiro[2.5]octane | S | C(O)C(Me)₂CH₂OH |
| H | H | 4-Cl-Bn | R | 2 | 1 | 4-Pid-1-yl | S | C(O)C(Me)₂CH₂OH |
| H | H | 4-Cl-Bn | R | 2 | 1 | 4-Ph-c-Hex | S | C(O)C(Me)₂CH₂OH |
| H | H | 4-Cl-Bn | R | 2 | 1 | Ph | R,S | C(O)C(Me)₂CH₂OH |
| H | H | 4-Cl-Bn | R | 2 | 1 | 2-adamantyl | S | C(O)C(Me)₂CH₂OH |
| H | H | 4-F-Bn | R | 2 | 1 | c-Hex | S | C(O)[(R)—CH(Me)CH₂OH] |
| H | H | 4-Cl-Bn | R | 2 | 1 | 4-trans-Me-c-Hex | S | C(O)[C(Me)(CH₂—OH)₂] |
| H | H | 4-Cl-Bn | R | 2 | 1 | 4-cis-Me-c-Hex | S | C(O)[C(Me)(CH₂—OH)₂] |
| H | H | 4-Cl-Bn | R | 2 | 1 | 4,4-diMe-c-Hex | S | C(O)[C(Me)(CH₂—OH)₂] |
| H | H | 4-Cl-Bn | R | 2 | 1 | c-Hex | S | C(O)[C(OH)(i-Pr)] |
| H | H | 4-Cl-Bn | R | 2 | 1 | c-Hex | S | C(O)[CH₂C(Me)₂—OH] |
| H | H | 4-Cl-Bn | R | 2 | 1 | c-Hex | S | C(O)(—(CH₂)₂—)C(O)OH |
| H | H | 4-Cl-Bn | R | 2 | 1 | c-Hex | S | C(O)(—(CH₂)₂—)C(O)OMe |

TABLE 1-continued

| R¹ | R² | R³ | *1 | n | m | R⁴ | *2 | R⁵ |
|---|---|---|---|---|---|---|---|---|
| H | H | 4-Cl-Bn | R | 2 | 1 | Pid-4-yl | S | C(O)C(Me)₂CH₂OH |
| H | H | 4-Cl-Bn | R | 2 | 1 | c-Hex | S | 2-(CH₂OH)-1-(c-peten)1-yl |
| H | H | 4-Cl-Bn | R | 2 | 1 | c-Hex | S | 2-(CH₂OH)-1-(c-hexen)1-yl |
| H | H | 4-Cl-Bn | R | 2 | 1 | c-Hex | S | C(O)N[(CH)₂OH]₂ |
| H | H | 4-Cl-Bn | R | 2 | 1 | c-Hex | S | C(O)N[(CH)₃OH]₂ |
| Me | H | 4-Cl-Bn | R | 2 | 1 | c-Hex | S | C(O)CH(Me)₂ |
| Me | H | 4-Cl-Bn | R | 2 | 1 | c-Hex | S | C(O)C(Me)₂CH₂OH |
| Me | H | 4-Cl-Bn | R | 2 | 1 | c-Hex | R | C(O)C(Me)₂CH₂OH |
| Me | H | 4-Cl-Bn | R | 2 | 1 | 4-trans-Me-c-Hex | S | C(O)C(Me)₂CH₂OH |
| Me | H | 4-Cl-Bn | R | 2 | 1 | 4-cis-Me-c-Hex | S | C(O)C(Me)₂CH₂OH |
| Me | H | 4-Cl-Bn | R | 2 | 1 | 4,4-diMe-c-Hex | S | C(O)C(Me)₂CH₂OH |
| Me | H | 4-Cl-Bn | R | 2 | 1 | 4-t-Bu-c-Hex | S | C(O)C(Me)₂CH₂OH |
| Me | H | 4-Cl-Bn | R | 2 | 1 | 4,4-diF-c-Hex | S | C(O)C(Me)₂CH₂OH |
| Me | H | 4-Cl-Bn | R | 2 | 1 | Spiro[2.5]octane | S | C(O)C(Me)₂CH₂OH |
| Me | H | 4-Cl-Bn | R | 2 | 1 | 4-F-c-Hex | S | C(O)C(Me)₂CH₂OH |
| Me | H | 4-Cl-Bn | R | 2 | 1 | 4-trans-Et-c-Hex | S | C(O)C(Me)₂CH₂OH |
| Me | H | 4-Cl-Bn | R | 2 | 1 | 4-cis-Et-c-Hex | S | C(O)C(Me)₂CH₂OH |
| Me | H | 4-Cl-Bn | R | 2 | 1 | 4-trans-Me-c-Hex | S | C(O)[C(Me)(CH₂—OH)₂] |
| Me | H | 4-Cl-Bn | R | 2 | 1 | 4-cis-Me-c-Hex | S | C(O)[C(Me)(CH₂—OH)₂] |
| Me | H | 4-Cl-Bn | R | 2 | 1 | 4,4-diMe-c-Hex | S | C(O)[C(Me)(CH₂—OH)₂] |
| Me | H | 4-Cl-Bn | R | 2 | 1 | 4,4-diMe-c-Hex | S | C(—CH₂CH₂)CH₂OH |
| Me | H | Bn | R | 2 | 1 | c-Hex | S | C(O)C(Me)₂CH₂OH |
| Me | H | 4-F-Bn | R | 2 | 1 | c-Hex | S | C(O)C(Me)₂CH₂OH |
| Me | H | 4-Me-Bn | R | 2 | 1 | c-Hex | S | C(O)C(Me)₂CH₂OH |
| Me | H | 4-MeO-Bn | R | 2 | 1 | c-Hex | S | C(O)C(Me)₂CH₂OH |
| i-Pr | H | 4-Cl-Bn | R | 2 | 1 | 4-trans-Me-c-Hex | S | C(O)[C(Me)(CH₂—OH)₂] |
| i-Pr | H | 4-Cl-Bn | R | 2 | 1 | 4-cis-Me-c-Hex | S | C(O)[C(Me)(CH₂—OH)₂] |
| i-Pr | H | 4-Cl-Bn | R | 2 | 1 | 4,4-diMe-c-Hex | S | C(O)[C(Me)(CH₂—OH)₂] |
| i-Pen | H | 4-Cl-Bn | R | 2 | 1 | c-Hex | S | C(O)C(Me)₂CH₂OH |
| Me | Me | 4-Cl-Bn | R | 2 | 1 | c-Hex | S | C(O)CH(Me)₂ |
| Me | Me | 4-Cl-Bn | R | 2 | 1 | c-Hex | S | C(O)C(Me)₃ |
| Me | Me | 4-Cl-Bn | R | 2 | 1 | c-Hex | S | C(O)C(Me)₂CH₂OH |
| Me | Me | 4-Cl-Bn | R | 2 | 1 | 4-trans-Me-c-Hex | S | C(O)C(Me)₂CH₂OH |
| Me | Me | 4-Cl-Bn | R | 2 | 1 | 4-cis-Me-c-Hex | S | C(O)C(Me)₂CH₂OH |
| Me | Me | 4-Cl-Bn | R | 2 | 1 | 4,4-diMe-c-Hex | S | C(O)C(Me)₂CH₂OH |
| Me | Me | 4-Cl-Bn | R | 2 | 1 | 4-trans-Et-c-Hex | S | C(O)C(Me)₂CH₂OH |
| Me | Me | 4-Cl-Bn | R | 2 | 1 | 4-cis-Et-c-Hex | S | C(O)C(Me)₂CH₂OH |
| Me | H | 4-Cl-Bn | R | 2 | 1 | c-Hex | S | C(O)C(Me)(CH₂—OH)₂ |
| Me | H | 4-Cl-Bn | R | 2 | 1 | c-Hex | S | C(O)C(Me)₂(CH₂—OMe) |
| Me | H | 4-Cl-Bn | R | 2 | 1 | c-Hex | S | C(O)C(Me)₂(CH₂—OMOM) |
| i-Pr | Me | 4-Cl-Bn | R | 2 | 1 | c-Hex | S | C(O)[(R)—CH(Me)CH₂OH] |
| Me | Me | 4-Cl-Bn | R | 2 | 1 | c-Hex | S | C(O)[(R)—CH(Me)CH₂OH] |
| Me | Me | 4-Cl-Bn | R | 2 | 1 | c-Hex | S | C(O)[C(Me)(CH₂—OH)₂] |
| Me | Me | 4-Cl-Bn | R | 2 | 1 | c-Hex | S | C(O)C(Me)(—CH₂OC(O)OCH₂—) |
| Me | Me | 4-Cl-Bn | R | 2 | 1 | 4-trans-Me-c-Hex | S | C(O)[C(Me)(CH₂—OH)₂] |
| Me | Me | 4-Cl-Bn | R | 2 | 1 | 4-cis-Me-c-Hex | S | C(O)[C(Me)(CH₂—OH)₂] |
| Me | Me | 4-Cl-Bn | R | 2 | 1 | 4,4-diMe-c-Hex | S | C(O)[C(Me)(CH₂—OH)₂] |
| Me | Me | Bn | R | 2 | 1 | c-Hex | S | C(O)C(Me)₂(CH₂—OH) |
| Me | Me | 4-F-Bn | R | 2 | 1 | c-Hex | S | C(O)C(Me)₂(CH₂—OH) |
| Me | Me | 4-Me-Bn | R | 2 | 1 | c-Hex | S | C(O)C(Me)₂(CH₂—OH) |
| Me | Me | 4-MeO-Bn | R | 2 | 1 | c-Hex | S | C(O)C(Me)₂(CH₂—OH) |
| Me | Me | 4-MeO-Bn | R | 2 | 1 | 4-t-Bu-c-Hex | S | C(O)C(Me)₂(CH₂—OH) |
| Et | Et | 4-Cl-Bn | R | 2 | 1 | c-Hex | S | C(O)C(Me)₂CH₂OH |
| i-Pr | H | 4-Cl-Bn | R | 2 | 1 | c-Hex | S | C(O)C(Me)₂CH₂OH |
| —(CH₂)₅— | | 4-MeO-Bn | R | 2 | 1 | c-Hex | S | C(O)C(Me)₂CH₂OH |
| MeO—(CH₂)₂— | H | 4-Cl-Bn | R | 2 | 1 | c-Hex | S | C(O)C(Me)₂CH₂OH |
| HO(CH₂)₂ | H | 4-Cl-Bn | R | 2 | 1 | c-Hex | S | C(O)C(Me)₂CH₂OH |
| Ac | H | 4-Cl-Bn | R | 2 | 1 | c-Hex | S | C(O)CH(Me)₂ |
| MeSO₂ | H | 4-Cl-Bn | R | 2 | 1 | c-Hex | S | C(O)CH(Me)₂ |
| (iPr)C(O) | H | 4-Cl-Bn | R | 2 | 1 | c-Hex | S | C(O)C(Me)₂CH₂OH |
| EtC(O) | H | 4-Cl-Bn | R | 2 | 1 | c-Hex | S | C(O)C(Me)₂CH₂OH |
| Gly | H | 4-Cl-Bn | R | 2 | 1 | c-Hex | S | C(O)[(R)—CH(Me)CH₂OH] |
| Gly | H | 4-Cl-Bn | R | 2 | 1 | c-Hex | S | C(O)C(Me)₂CH₂OH |
| HO(CH₂)₃C(O) | H | 4-Cl-Bn | R | 2 | 1 | c-Hex | S | C(O)C(Me)₂CH₂OH |
| (Me)₂N-Gly | H | 4-Cl-Bn | R | 2 | 1 | c-Hex | S | C(O)C(Me)₂CH₂OH |
| i-Bu | H | 4-Cl-Bn | R | 2 | 1 | c-Hex | S | C(O)C(Me)₂CH₂OH |
| —(CH₂)₄— | | 4-Cl-Bn | R | 2 | 1 | c-Hex | S | C(O)C(Me)₂CH₂OH |
| —(CH₂)₅— | | 4-Cl-Bn | R | 2 | 1 | c-Hex | S | C(O)C(Me)₂CH₂OH |
| NH₂—(CH₂)₄ | H | 4-Cl-Bn | R | 2 | 1 | c-Hex | S | C(O)C(Me)₂CH₂OH |
| HOCH₂C(Me)₂C(O) | H | 4-Cl-Bn | R | 2 | 1 | c-Hex | S | C(O)C(Me)₂CH₂OH |
| imidazol-2-yl | H | 4-Cl-Bn | R | 2 | 1 | c-Hex | S | C(O)C(Me)₂CH₂OH |
| imidazol-4-yl | H | 4-Cl-Bn | R | 2 | 1 | c-Hex | S | C(O)C(Me)₂CH₂OH |
| HO(CH₂)₄ | H | 4-Cl-Bn | R | 2 | 1 | c-Hex | S | C(O)C(Me)₂CH₂OH |
| PrC(O) | H | 4-Cl-Bn | R | 2 | 1 | c-Hex | S | C(O)C(Me)₂CH₂OH |
| Pyd-3-yl | H | 4-Cl-Bn | R | 2 | 1 | c-Hex | S | C(O)C(Me)₂CH₂OH |
| (S)Pyd-2-CH₂— | H | 4-Cl-Bn | R | 2 | 1 | c-Hex | S | C(O)C(Me)₂CH₂OH |
| MeOC(O)CH₂ | H | 4-Cl-Bn | R | 2 | 1 | c-Hex | S | C(O)C(Me)₂CH₂OH |
| DTic | H | 4-Cl-Bn | R | 2 | 1 | c-Hex | S | C(O)C(Me)₂CH₂OH |

TABLE 1-continued

| R¹ | R² | R³ | *1 | n | m | R⁴ | *2 | R⁵ |
|---|---|---|---|---|---|---|---|---|
| NH₂—(CH₂)₂ | H | 4-Cl-Bn | R | 2 | 1 | c-Hex | S | C(O)C(Me)₂CH₂OH |
| (Me)HN—(CH₂)₂ | H | 4-Cl-Bn | R | 2 | 1 | c-Hex | S | C(O)C(Me)₂CH₂OH |
| (S)Pyd-2-CH₂ | Me | 4-Cl-Bn | R | 2 | 1 | c-Hex | S | C(O)CH(Me)₂ |
| (R)Pyd-2-CH₂ | H | 4-Cl-Bn | R | 2 | 1 | c-Hex | S | C(O)[2-(CH₂OH)-1-(c-penten)-1-yl] |
| (Me)₂NC(O)—CH₂ | H | 4-Cl-Bn | R | 2 | 1 | c-Hex | S | C(O)CH(Me)₂ |
| NH₂C(O)—CH₂ | H | 4-Cl-Bn | R | 2 | 1 | c-Hex | S | C(O)CH(Me)₂ |
| MeO₂C—CH₂ | H | 4-Cl-Bn | R | 2 | 1 | c-Hex | S | C(O)CH(Me)₂ |
| HO₂C—CH₂ | H | 4-Cl-Bn | R | 2 | 1 | c-Hex | S | C(O)CH(Me)₂ |
| Gly | H | 4-Cl-Bn | R | 2 | 1 | c-Hex | S | C(O)CH(Me)₂ |
| N—Me-Gly | H | 4-Cl-Bn | R | 2 | 1 | c-Hex | S | C(O)CH(Me)₂ |
| N-diMe-Gly | H | 4-Cl-Bn | R | 2 | 1 | c-Hex | S | C(O)CH(Me)₂ |
| N—Ac-Gly | H | 4-Cl-Bn | R | 2 | 1 | c-Hex | S | C(O)CH(Me)₂ |
| N-Ms-Gly | H | 4-Cl-Bn | R | 2 | 1 | c-Hex | S | C(O)CH(Me)₂ |
| (R)Ala | H | 4-Cl-Bn | R | 2 | 1 | c-Hex | S | C(O)CH(Me)₂ |
| β-Ala | H | 4-Cl-Bn | R | 2 | 1 | c-Hex | S | C(O)CH(Me)₂ |
| β-Ala | H | 4-Cl-Bn | R | 2 | 1 | c-Hex | S | C(O)C(Me)₃ |
| N—Me-β-Ala | H | 4-Cl-Bn | R | 2 | 1 | c-Hex | S | C(O)CH(Me)₂ |
| N-diMe-β-Ala | H | 4-Cl-Bn | R | 2 | 1 | c-Hex | S | C(O)CH(Me)₂ |
| NH₂(CH₂)₄ | H | 4-Cl-Bn | R | 2 | 1 | c-Hex | S | C(O)CH(Me)₂ |
| (S)Ala | H | 4-Cl-Bn | R | 2 | 1 | c-Hex | S | C(O)CH(Me)₂ |
| (S)His | H | 4-Cl-Bn | R | 2 | 1 | c-Hex | S | C(O)CH(Me)₂ |
| (S)His | H | 4-Cl-Bn | R | 2 | 1 | c-Hex | S | C(O)C(Me)₃ |
| N-Me-(S)His | H | 4-Cl-Bn | R | 2 | 1 | c-Hex | S | C(O)CH(Me)₂ |
| N-Ac-(S)His | H | 4-Cl-Bn | R | 2 | 1 | c-Hex | S | C(O)CH(Me)₂ |
| N-Ac-(S)His | H | 4-Cl-Bn | R | 2 | 1 | c-Hex | S | C(O)C(Me)₃ |
| N-Ms-(S)His | H | 4-Cl-Bn | R | 2 | 1 | c-Hex | S | C(O)CH(Me)₂ |
| (R)His | H | 4-Cl-Bn | R | 2 | 1 | c-Hex | S | C(O)CH(Me)₂ |
| (S)Phe | H | 4-Cl-Bn | R | 2 | 1 | c-Hex | S | C(O)CH(Me)₂ |
| (R)Phe | H | 4-Cl-Bn | R | 2 | 1 | c-Hex | S | C(O)CH(Me)₂ |
| (R)Pro | H | 4-Cl-Bn | R | 2 | 1 | c-Hex | S | C(O)CH(Me)₂ |
| (R)Pro | H | 4-Cl-Bn | R | 2 | 1 | c-Hex | S | C(O)C(Me)₃ |
| N—Me-(R)Pro | H | 4-Cl-Bn | R | 2 | 1 | c-Hex | S | C(O)C(Me)₃ |
| (S)Pro | H | 4-Cl-Bn | R | 2 | 1 | c-Hex | S | C(O)CH(Me)₂ |
| (R)Pid-2-CO | H | 4-Cl-Bn | R | 2 | 1 | c-Hex | S | C(O)CH(Me)₂ |
| (R)Pid-2-CO | H | 4-Cl-Bn | R | 2 | 1 | c-Hex | S | C(O)C(Me)₃ |
| N—Me-(R)Pid-2-CO | H | 4-Cl-Bn | R | 2 | 1 | c-Hex | S | C(O)CH(Me)₂ |
| N—Ac-(R)Pid-2-CO | H | 4-Cl-Bn | R | 2 | 1 | c-Hex | S | C(O)CH(Me)₂ |
| (S)Pid-2-CO | H | 4-Cl-Bn | R | 2 | 1 | c-Hex | S | C(O)CH(Me)₂ |
| (R)Tic | H | 4-Cl-Bn | R | 2 | 1 | c-Hex | S | C(O)CH(Me)₂ |
| (R)Tic | H | Bn | R | 2 | 1 | c-Hex | S | C(O)CH(Me)₂ |
| (S)Tic | H | 4-Cl-Bn | R | 2 | 1 | c-Hex | R | C(O)CH(Me)₂ |
| cis-Dic | H | 4-Cl-Bn | R | 2 | 1 | c-Hex | S | C(O)CH(Me)₂ |
| 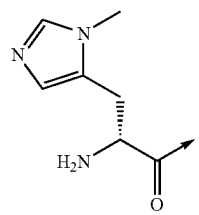 | H | 4-Cl-Bn | R | 2 | 1 | c-Hex | S | C(O)CH(Me)₂ |
| 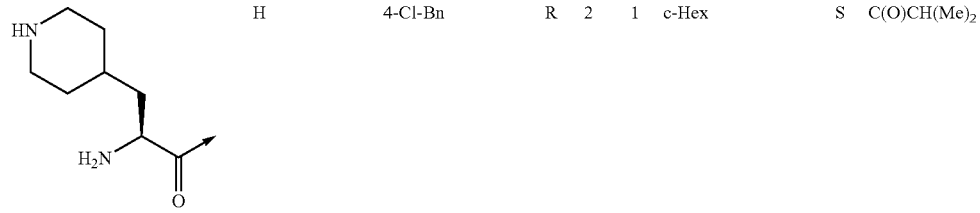 | | | | | | | | |
| | H | 4-Cl-Bn | R | 2 | 1 | c-Hex | S | C(O)CH(Me)₂ |
| 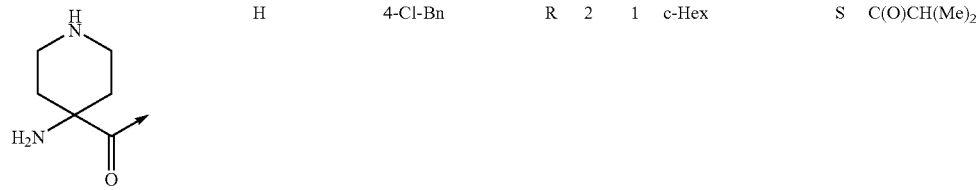 | | | | | | | | |
| | H | 4-Cl-Bn | R | 2 | 1 | c-Hex | S | C(O)CH(Me)₂ |

TABLE 1-continued

| R¹ | R² | R³ | *1 | n | m | R⁴ | *2 | R⁵ |
|---|---|---|---|---|---|---|---|---|
| 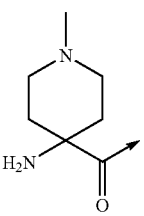 | H | 4-Cl-Bn | R | 2 | 1 | c-Hex | S | C(O)CH(Me)₂ |
| 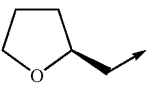 | H | 4-Cl-Bn | R | 2 | 1 | c-Hex | S | C(O)CH(Me)₂ |
| 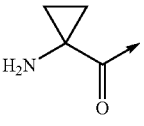 | H | 4-Cl-Bn | R | 2 | 1 | c-Hex | S | C(O)CH(Me)₂ |
| 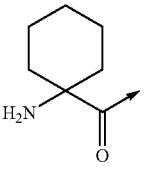 | H | 4-Cl-Bn | R | 2 | 1 | c-Hex | S | C(O)CH(Me)₂ |
| 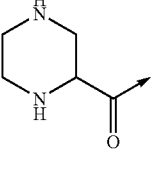 | H | 4-Cl-Bn | R | 2 | 1 | c-Hex | S | C(O)CH(Me)₂ |
| HO—CH₂—C(O) | H | 4-Cl-Bn | R | 2 | 1 | c-Hex | S | C(O)CH(Me)₂ |
| 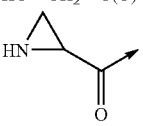 | H | 4-Cl-Bn | R | 2 | 1 | c-Hex | S | C(O)CH(Me)₂ |
| HO—C(O)CH₂ | H | 4-Cl-Bn | R | 2 | 1 | c-Hex | S | C(O)C(Me)₂CH₂OH |
| HO—C(O)CH₂ | HO—C(O)CH₂ | 4-Cl-Bn | R | 2 | 1 | c-Hex | S | C(O)C(Me)₂CH₂OH |
| MeOC(O)CH₂ | H | 4-Cl-Bn | R | 2 | 1 | c-Hex | S | C(O)C(Me)₂ |
| (R)Pyd-2-CH₂ | H | 4-Cl-Bn | R | 2 | 1 | c-Hex | S | C(O)CH(Me)₂ |
| (R)Pyd-2-CH₂ | H | 4-Cl-Bn | R | 2 | 1 | c-Hex | S | C(O)C(Me)₃ |
| (R)Pyd-2-CH₂ | H | 4-Cl-Bn | R | 2 | 1 | c-Hex | R | C(O)CH(Me)₂ |
| (R)Pyd-2-CH₂ | H | 4-Cl-Bn | R | 2 | 1 | 2,3-diF—Ph | R | C(O)CH(Me)₂ |
| (R)Pyd-2-CH₂ | H | 4-Cl-Bn | R | 2 | 1 | 2,4-diF—Ph | R | C(O)CH(Me)₂ |
| (R)Pyd-2-CH₂ | H | 4-Cl-Bn | R | 2 | 1 | c-Pen | S | C(O)CH(Me)₂ |
| (R)Pyd-2-CH₂ | H | Bn | R | 2 | 1 | c-Hex | S | C(O)CH(Me)₂ |
| (R)Pyd-2-CH₂ | H | (c-Hex)-CH₂— | R | 2 | 1 | c-Hex | S | C(O)CH(Me)₂ |
| (R)Pyd-2-CH₂ | Me | 4-Cl-Bn | R | 2 | 1 | c-Hex | S | C(O)CH(Me)₂ |
| (R)-1-Me-Pyd-2-CH₂ | H | 4-Cl-Bn | R | 2 | 1 | c-Hex | S | C(O)CH(Me)₂ |
| (R)-1-Me-Pyd-2-CH₂ | Me | 4-Cl-Bn | R | 2 | 1 | c-Hex | S | C(O)CH(Me)₂ |
| (R)-1-Ac-Pyd-2-CH₂ | H | 4-Cl-Bn | R | 2 | 1 | c-Hex | S | C(O)CH(Me)₂ |
| (S)Pyd-2-CH₂ | H | 4-Cl-Bn | R | 2 | 1 | c-Hex | S | C(O)CH(Me)₂ |
| (S)-1-Me-Pyd-2-CH₂ | H | 4-Cl-Bn | R | 2 | 1 | c-Hex | S | C(O)CH(Me)₂ |
| (R)Pid-2-CH₂ | H | 4-Cl-Bn | R | 2 | 1 | c-Hex | S | C(O)CH(Me)₂ |
| (R)-1-Me-Pid-2-CH₂ | H | 4-Cl-Bn | R | 2 | 1 | c-Hex | S | C(O)CH(Me)₂ |
| (R)-1-Me-Pid-2-CH₂ | Me | 4-Cl-Bn | R | 2 | 1 | c-Hex | S | C(O)CH(Me)₂ |
| (S)Pid-2-CH₂ | H | 4-Cl-Bn | R | 2 | 1 | c-Hex | S | C(O)CH(Me)₂ |
| (S)-1-Me-Pid-2-CH₂ | H | 4-Cl-Bn | R | 2 | 1 | c-Hex | S | C(O)CH(Me)₂ |
| NH₂—(CH₂)₂ | H | 4-Cl-Bn | R | 2 | 1 | c-Hex | S | C(O)CH(Me)₂ |
| NH₂—(CH₂)₂ | Me | 4-Cl-Bn | R | 2 | 1 | c-Hex | S | C(O)CH(Me)₂ |
| (Me)N—(CH₂)₂ | H | 4-Cl-Bn | R | 2 | 1 | c-Hex | S | C(O)CH(Me)₂ |
| (Me)N—(CH₂)₂ | Me | 4-Cl-Bn | R | 2 | 1 | c-Hex | S | C(O)CH(Me)₂ |
| (Me)N—(CH₂)₂ | H | 4-Cl-Bn | R | 2 | 1 | c-Hex | R | C(O)CH(Me)₂ |
| (Me)N—(CH₂)₂ | H | 4-Cl-Bn | R | 2 | 1 | c-Hex | R | C(O)C(Me)₃ |
| (Me)₂N—(CH₂)₂ | H | 4-Cl-Bn | R | 2 | 1 | c-Hex | S | C(O)CH(Me)₂ |
| (Me)₂N—(CH₂)₂ | H | 4-Cl-Bn | R | 2 | 1 | c-Hex | S | C(O)C(Me)₃ |

TABLE 1-continued

| R¹ | R² | R³ | *1 | n | m | R⁴ | *2 | R⁵ |
|---|---|---|---|---|---|---|---|---|
| (Me)₂N—(CH₂)₂ | H | Bn | R | 2 | 1 | c-Hex | S | C(O)CH(Me)₂ |
| (Me)₂N—(CH₂)₂ | H | (c-Hex)-CH₂— | R | 2 | 1 | c-Hex | S | C(O)CH(Me)₂ |
| (Me)₂N—(CH₂)₂ | Me | 4-Cl-Bn | R | 2 | 1 | c-Hex | S | C(O)CH(Me)2 |
| (Me)N—(CH₂)₂— | H | 4-Cl-Bn | R | 2 | 1 | c-Hex | S | C(O)C(Me)₂CH₂OH |
| (Me)₂N—(CH₂)₂— | H | 4-Cl-Bn | R | 2 | 1 | c-Hex | S | C(O)CH(Me)CH₂OH |
| (Me)₂N—(CH₂)₂— | H | 4-Cl-Bn | R | 2 | 1 | c-Hex | S | C(O)C(Me)₂CH₂OH |
| (Me)₂N—(CH₂)₂— | H | 4-Cl-Bn | R | 2 | 1 | c-Hex | S | C(O)C(Me)(CH₂—OH)₂ |
| (Me)₂N—(CH₂)₂— | H | 4-Cl-Bn | R | 2 | 1 | c-Hex | S | C(O)C(Me)₂[CH₂—N(Me)] |
| (Me)₂N—(CH₂)₂— | H | 4-Cl-Bn | R | 2 | 1 | c-Hex | S | C(O)C(Me)₂CH₂—OMe |
| (Me)₂N—(CH₂)₂— | H | 4-Cl-Bn | R | 2 | 1 | c-Hex | S | C(O)C(Me)₂(CH₂—OMOM) |
| (Me)₂N—(CH₂)₂— | H | 4-Cl-Bn | R | 2 | 1 | c-Hex | S | C(O)C(Me)₂CH₂—OBn |
| (Me)₂N—(CH₂)₂— | H | 4-Cl-Bn | R | 2 | 1 | c-Hex | S | C(O)C(Me)₂[CH₂—O(i-Bu)] |
| (Me)₂N—(CH₂)₂— | H | 4-Cl-Bn | R | 2 | 1 | c-Hex | S | C(O)C(Me)₂CH₂—OPh |
| (Me)₂N—(CH₂)₂— | H | 4-Cl-Bn | R | 2 | 1 | c-Hex | S | C(O)C(Me)₂CH₂—SPh |
| (Me)₂N—(CH₂)₂— | H | 4-Cl-Bn | R | 2 | 1 | c-Hex | S | C(O)C(Me)₂CH₂—OCOPh |
| (Me)₂N—(CH₂)₂— | H | 4-Cl-Bn | R | 2 | 1 | c-Hex | S | C(O)C(Me)₂[CH₂—OCO(c-Hex)] |
| (Me)₂N—(CH₂)₂— | H | 4-Cl-Bn | R | 2 | 1 | c-Hex | S | C(O)C(Me)₂CH₂—OCOBn |
| (Me)₂N—(CH₂)₂— | H | 4-Cl-Bn | R | 2 | 1 | c-Hex | S | C(O)C(Me)₂CH₂—OCOBu |
| (Me)₂N—(CH₂)₂— | H | 4-Cl-Bn | R | 2 | 1 | c-Hex | S | C(O)C(Me)₂[CH₂—OCO(i-Pr)] |
| (Me)₂N—(CH₂)₂— | H | 4-Cl-Bn | R | 2 | 1 | c-Hex | S | C(O)C(Me)₂[CH₂—OCO(2,5diF—Ph)] |
| (Me)₂N—(CH₂)₂— | H | 4-Cl-Bn | R | 2 | 1 | c-Hex | S | C(O)C(Me)₂OAc |
| (Me)₂N—(CH₂)₂— | H | 4-Cl-Bn | R | 2 | 1 | c-Hex | S | C(O)[2-(HOCH₂)-1-(c-penten)-1-yl] |
| (Me)₂N—(CH₂)₂— | H | 4-Cl-Bn | R | 2 | 1 | c-Hex | S | C(O)[(3S)-3-(OH)-Pyd-1-yl] |
| (Me)₂N—(CH₂)₂— | H | 4-Cl-Bn | R | 2 | 1 | c-Hex | S | C(O)C(Me)₂(CHO) |
| (Me)₂N—(CH₂)₂— | H | 4-Cl-Bn | R | 2 | 1 | c-Hex | S | C(O)C(Me)₂(CH=N—OMe) |
| (Me)₂N—(CH₂)₂— | H | 4-Cl-Bn | R | 2 | 1 | 2,3-diF—Ph | S | C(O)C(Me)₂(CH₂—OH) |
| (Me)₂N—(CH₂)₂— | H | 4-Cl-Bn | R | 2 | 1 | 2,3-diF—Ph | S | C(O)N(Me)₂ |
| (Me)₂N—(CH₂)₂— | H | 4-Cl-Bn | R | 2 | 1 | 4-cis-Mec-Hex | S | C(O)C(Me)₂CH₂OH |
| (Me)₂N—(CH₂)₂— | H | 4-Cl-Bn | R | 2 | 1 | 4,4-diMe-c-Hex | S | C(O)C(Me)₂CH₂OH |
| AcNH—(CH₂)₂ | H | 4-Cl-Bn | R | 2 | 1 | c-Hex | S | C(O)CH(Me)₂ |
| (Et)₂N—(CH₂)₂ | H | 4-Cl-Bn | R | 2 | 1 | c-Hex | S | C(O)CH(Me)₂ |
| [Me(Et)]N—(CH₂)₂ | H | 4-Cl-Bn | R | 2 | 1 | c-Hex | S | C(O)CH(Me)₂ |
| aziridin-2-yl-CH₂ | H | 4-Cl-Bn | R | 2 | 1 | c-Hex | S | C(O)CH(Me)₂ |
| aziridin-1-yl-(CH₂)₂ | H | 4-Cl-Bn | R | 2 | 1 | c-Hex | S | C(O)CH(Me)₂ |
| 1-Me-azetidin-3-yl | H | 4-Cl-Bn | R | 2 | 1 | c-Hex | S | C(O)CH(Me)₂ |
| azetidin-3-yl | H | 4-Cl-Bn | R | 2 | 1 | c-Hex | S | C(O)CH(Me)₂ |
| (R)Pyd-3-yl | H | 4-Cl-Bn | R | 2 | 1 | c-Hex | S | C(O)CH(Me)₂ |
| azetidin-2-yl-CHO | H | 4-Cl-Bn | R | 2 | 1 | c-Hex | S | C(O)CH(Me)₂ |
| Pid-4-yl | H | 4-Cl-Bn | R | 2 | 1 | c-Hex | S | C(O)CH(Me)₂ |
| Pid-4-yl | Me | 4-Cl-Bn | R | 2 | 1 | c-Hex | S | C(O)CH(Me)₂ |
| 1-Me-Pid-4-yl | Me | 4-Cl-Bn | R | 2 | 1 | c-Hex | S | C(O)CH(Me)₂ |
| (Me)₂N—CH= | H | 4-Cl-Bn | R | 2 | 1 | c-Hex | S | C(O)CH(Me)₂ |
| Pyd-1-(CH₂)₂ | H | 4-Cl-Bn | R | 2 | 1 | c-Hex | S | C(O)CH(Me)₂ |
| H | H | 4-Cl-Bn | R | 2 | 2 | c-Hex | | C(O)CH(Me)₂ |
| H | H | 4-Cl-Bn | R | 2 | 2 | c-Hex | | C(O)C(Me)₃ |
| H | H | 4-Cl-Bn | R | 2 | 2 | c-Hex | | C(O)OMe |
| H | H | 4-Cl-Bn | R | 2 | 2 | c-Hex | | CH₂C(O)OMe |
| H | H | 4-Cl-Bn | R | 2 | 2 | c-Hex | | CH₂C(O)N(Me)₂ |
| H | H | 4-Cl-Bn | R | 2 | 2 | c-Hex | | C(O)N(Me)₂ |
| H | H | 4-Cl-Bn | R | 2 | 2 | c-Hex | | Gly |
| H | H | 4-Cl-Bn | R | 2 | 2 | c-Hex | | C(O)N(Me)₂ |
| H | H | 4-Cl-Bn | R | 2 | 2 | c-Hex | | C(O)NH(i-Pr) |
| H | H | 4-Cl-Bn | R | 2 | 2 | c-Hex | | C(O)N(Me)(i-Pr) |
| H | H | 4-Cl-Bn | R | 2 | 2 | c-Hex | | C(O)NH(Bu) |
| H | H | 4-Cl-Bn | R | 2 | 2 | c-Hex | | C(O)N(Me)(Bu) |
| H | H | 4-Cl-Bn | R | 2 | 2 | c-Hex | | C(O)NH(c-Hex) |
| H | H | 4-Cl-Bn | R | 2 | 2 | c-Hex | | C(O)NHPh |
| H | H | 4-Cl-Bn | R | 2 | 2 | c-Hex | | C(S)NH(Et) |
| H | H | 4-Cl-Bn | R | 2 | 2 | c-Hex | | C(S)N(Me)(Et) |
| H | H | 4-Cl-Bn | R | 2 | 2 | c-Hex | | SO₂Me |

TABLE 1-continued

| R¹ | R² | R³ | *1 | n | m | R⁴ | *2 | R⁵ |
|---|---|---|---|---|---|---|---|---|
| H | H | 4-Cl-Bn | R | 2 | 2 | c-Pen | | C(O)CH(Me)₂ |
| H | H | 4-Cl-Bn | R | 2 | 2 | c-Hep | | C(O)CH(Me)₂ |
| H | H | 4-Cl-Bn | R | 2 | 2 | Ph | | C(O)CH(Me)₂ |
| H | H | 4-Cl-Bn | R | 2 | 2 | 2-MeO-Ph | | C(O)CH(Me)₂ |
| H | H | 4-Cl-Bn | R | 2 | 2 | 3-MeO-Ph | | C(O)CH(Me)₂ |
| H | H | 4-Cl-Bn | R | 2 | 2 | 2-Cl-Ph | | C(O)CH(Me)₂ |
| H | H | 4-Cl-Bn | R | 2 | 2 | 2-F-Ph | | C(O)CH(Me)₂ |
| H | H | 4-Cl-Bn | R | 2 | 2 | 3-F-Ph | | C(O)CH(Me)₂ |
| H | H | 4-Cl-Bn | R | 2 | 2 | 4-F-Ph | | C(O)CH(Me)₂ |
| H | H | 4-Cl-Bn | R | 2 | 2 | 2,3-diF—Ph | | C(O)CH(Me)₂ |
| H | H | 4-Cl-Bn | R | 2 | 2 | 2,4-diF—Ph | | C(O)CH(Me)₂ |
| H | H | 4-Cl-Bn | R | 2 | 2 | 2,5-diF—Ph | | C(O)CH(Me)₂ |
| H | H | 4-Cl-Bn | R | 2 | 2 | 2,6-diF—Ph | | C(O)CH(Me)₂ |
| H | H | 4-Cl-Bn | R | 2 | 2 | 3,4-diF—Ph | | C(O)CH(Me)₂ |
| H | H | 4-Cl-Bn | R | 2 | 2 | 2-F-4-MeO-Ph | | C(O)CH(Me)₂ |
| H | H | 4-Cl-Bn | S | 2 | 2 | c-Hex | | C(O)CH(Me)₂ |
| H | H | 4-Br-Bn | R | 2 | 2 | c-Hex | | C(O)CH(Me)₂ |
| H | H | 3,4-diCl-Bn | R | 2 | 2 | c-Hex | | C(O)CH(Me)₂ |
| H | H | 4-F-Bn | R | 2 | 2 | 2,3-diF—Ph | | C(O)CH(Me)₂ |
| H | H | 4-HO-Bn | R | 2 | 2 | c-Hex | | C(O)CH(Me)₂ |
| H | H | 4-MeO-Bn | R | 2 | 2 | 2,3-diF—Ph | | C(O)CH(Me)₂ |
| H | H | (c-Hex)-CH₂ | R | 2 | 2 | c-Hex | | C(O)CH(Me)₂ |
| H | H | 3,4-diCl-Bn | R | 2 | 2 | c-Hex | | C(O)CH(Me)₂ |
| H | H | 4-F-Bn | R | 2 | 2 | 2,3-diF—Ph | | C(O)CH(Me)₂ |
| H | H | 4-HO-Bn | R | 2 | 2 | c-Hex | | C(O)CH(Me)₂ |
| H | H | 4-MeO-Bn | R | 2 | 2 | 2,3-diF—Ph | | C(O)CH(Me)₂ |
| H | H | (c-Hex)-CH₂ | R | 2 | 2 | c-Hex | | C(O)CH(Me)₂ |
| H | H | 4-Cl-Bn | R | 2 | 2 | 2,3-diF—Ph | | C(O)N(Me)(CH₂)₂OH |
| H | H | 4-Cl-Bn | R | 2 | 2 | 2,3-diF—Ph | | C(O)N(Me)(CH₂)₂OMe |
| H | H | 4-Cl-Bn | R | 2 | 2 | c-Hex | | C(O)CH(Me)CH₂OH |
| H | H | 4-Cl-Bn | R | 2 | 2 | c-Hex | | C(O)C(Me)₂CH₂OH |
| H | H | 4-Cl-Bn | R | 2 | 2 | c-Hex | | C(O)[2-(CH₂OH)-1-(c-penten)-1-yl] |
| H | H | 4-Cl-Bn | R | 2 | 2 | c-Hex | | C(O)[2-(CH₂OH)-1-(c-hexen)-1-yl] |
| H | H | 4-Cl-Bn | R | 2 | 2 | 2,3-diF—Ph | | C(O)C(Me)₂CH₂OH |
| H | H | 4-Cl-Bn | R | 2 | 2 | c-Hex | | C(O)N(Me)(CH₂)₂OH |
| H | H | 4-Cl-Bn | R | 2 | 2 | c-Hex | | C(O)N(Et)(CH₂)₂OH |
| H | H | 4-Cl-Bn | R | 2 | 2 | c-Hex | | C(O)N(n-Pr)(CH₂)₂OH |
| H | H | 4-Cl-Bn | R | 2 | 2 | c-Hex | | C(O)N(c-Pr)(CH₂)₂OH |
| H | H | 4-Cl-Bn | R | 2 | 2 | c-Hex | | C(O)N(i-Pr)(CH₂)₂OH |
| H | H | 4-Cl-Bn | R | 2 | 2 | c-Hex | | C(O)N[(CH₂)₂OMe](CH₂)₂OH |
| H | H | 4-Cl-Bn | R | 2 | 2 | c-Hex | | C(O)N(Me)(CH₂)₂OMe |
| H | H | 4-Cl-Bn | R | 2 | 2 | c-Hex | | C(O)NH(CH₂)₂OMe |
| H | H | 4-Cl-Bn | R | 2 | 2 | c-Hex | | C(O)N(Et)(CH₂)₂OMe |
| H | H | 4-Cl-Bn | R | 2 | 2 | c-Hex | | C(O)N[(CH₂)₂OMe]₂ |
| H | H | 4-Cl-Bn | R | 2 | 2 | c-Hex | | C(O)N[(CH₂)₂OH]₂ |
| H | H | 4-Cl-Bn | R | 2 | 2 | c-Hex | | C(O)N(Me)₂ |
| H | H | 4-Cl-Bn | R | 2 | 2 | c-Hex | | C(O)N(Et)₂ |
| H | H | 4-Cl-Bn | R | 2 | 2 | c-Hex | | C(O)N(Me)OMe |
| H | H | 4-Cl-Bn | R | 2 | 2 | c-Hex | | C(O)N(Me)[C(Me)₂CH₂NH₂] |
| H | H | 4-Cl-Bn | R | 2 | 2 | c-Hex | | C(O)N[(CH₂)₂OMe](CH₂)₂F |
| H | H | 4-Cl-Bn | R | 2 | 2 | c-Hex | | C(O)N(Me)(CH₂)₂F |
| H | H | 4-Cl-Bn | R | 2 | 2 | c-Hex | | C(O)N(Et)(CH₂)₃OH |
| H | H | 4-Cl-Bn | R | 2 | 2 | c-Hex | | C(O)N[(CH₂)₃OH]₂ |
| H | H | 4-Cl-Bn | R | 2 | 2 | c-Hex | | C(O)N[(CH₂)₂OMe](CH₂)₃OH |
| H | H | 4-Cl-Bn | R | 2 | 2 | c-Hex | | C(O)N[(CH₂)₂F](CH₂)₃OH |
| H | H | 4-Cl-Bn | R | 2 | 2 | c-Hex | | C(O)N[(CH₂)₂F](CH₂)₂OH |
| H | H | 4-Cl-Bn | R | 2 | 2 | c-Hex | | C(O)N[(CH₂)₂F]₂ |
| H | H | 4-F-Bn | R | 2 | 2 | c-Hex | | C(O)N(Me)(CH₂)₂OMe |
| H | H | 4-F-Bn | R | 2 | 2 | c-Hex | | C(O)N(Me)(CH₂)₂OH |
| H | H | 4-F-Bn | R | 2 | 2 | c-Hex | | C(O)N(Et)(CH₂)₂OH |
| H | H | 4-F-Bn | R | 2 | 2 | c-Hex | | C(O)N(Et)(CH₂)₂F |
| H | H | 4-F-Bn | R | 2 | 2 | c-Hex | | C(O)N(Et)(CH₂)₃F |
| H | H | 4-F-Bn | R | 2 | 2 | c-Hex | | C(O)N(n-Pr)(CH₂)₂OH |
| H | H | 4-F-Bn | R | 2 | 2 | c-Hex | | C(O)N(c-Pr)(CH₂)₂OH |
| H | H | 4-F-Bn | R | 2 | 2 | c-Hex | | C(O)N[(CH₂)₂OMe](CH₂)₂OH |
| H | H | 4-F-Bn | R | 2 | 2 | c-Hex | | C(O)N(Me)(CH₂)₂OMe |
| H | H | 4-F-Bn | R | 2 | 2 | c-Hex | | C(O)N[(CH₂)₂OMe](CH₂)₂F |
| H | H | 4-F-Bn | R | 2 | 2 | c-Hex | | C(O)N(Me)(CH₂)₂F |
| H | H | 4-F-Bn | R | 2 | 2 | c-Hex | | C(O)N(Et)(CH₂)₃OH |
| H | H | 4-F-Bn | R | 2 | 2 | c-Hex | | C(O)N[(CH₂)₂F](CH₂)₃OH |
| H | H | 4-F-Bn | R | 2 | 2 | c-Hex | | C(O)N[(CH₂)₂F]₂ |
| H | H | 4-Cl-Bn | R | 2 | 2 | c-Hex | | C(O)[(3S)-3-(OH)-Pyd-1-yl] |
| H | H | 4-Cl-Bn | R | 2 | 2 | c-Hex | | C(O)[(3R)-3-(OH)-Pyd-1-yl] |
| H | H | 4-Cl-Bn | R | 2 | 2 | c-Hex | | C(O)[(2R)-2-(HOCH₂)-Pyd-1-yl] |
| H | H | 4-Cl-Bn | R | 2 | 2 | c-Hex | | C(O)[(2S)-2-(HOCH₂)-Pyd-1-yl] |
| H | H | 4-Cl-Bn | R | 2 | 2 | c-Hex | | C(O)[(3R)-3-amino-Pyd-1-yl] |
| H | H | 4-Cl-Bn | R | 2 | 2 | c-Hex | | C(O)[(3S)-3-amino-Pyd-1-yl] |
| H | H | 4-Cl-Bn | R | 2 | 2 | c-Hex | | C(O)[(3R)-3-(OH)-Pid-1-yl] |

TABLE 1-continued

| R¹ | R² | R³ | *1 | n | m | R⁴ | *2 | R⁵ |
|---|---|---|---|---|---|---|---|---|
| H | H | 4-Cl-Bn | R | 2 | 2 | c-Hex | | C(O)[(3S)-3-(OH)-Pid-1-yl] |
| H | H | 4-Cl-Bn | R | 2 | 2 | c-Hex | | C(O)[4-(OH)-Pid-1-yl] |
| H | H | 4-Cl-Bn | R | 2 | 2 | c-Hex | | C(O)[4-amino-Pid-1-yl] |
| H | H | 4-Cl-Bn | R | 2 | 2 | c-Hex | | C(O)(—(CH₂)₂—)C(O)OH |
| H | H | 4-Cl-Bn | R | 2 | 2 | c-Hex | | C(O)(—(CH₂)₂—)C(O)OMe |
| H | H | 4-Cl-Bn | R | 2 | 2 | 4-cis-Me-c-Hex | | C(O)C(Me)₂CH₂OH |
| H | H | 4-Cl-Bn | R | 2 | 2 | 4-trans-Me-c-Hex | | C(O)C(Me)₂CH₂OH |
| H | H | 4-Cl-Bn | R | 2 | 2 | 4-diMe-c-Hex | | C(O)(—(CH₂)₂—)C(O)OMe |
| H | H | 4-Cl-Bn | R | 2 | 2 | c-Hex | | C(O)N(Et)(CH₂)₂F |
| H | H | 4-Cl-Bn | R | 2 | 2 | c-Hex | | C(O)N(Et)(CH₂)₃F |
| H | H | 4-Cl-Bn | R | 2 | 2 | c-Hex | | C(O)N(i-Pr)(CH₂)₂OH |
| H | H | 4-Cl-Bn | R | 2 | 2 | c-Hex | | C(O)N(Et)₂ |
| H | H | 4-Cl-Bn | R | 2 | 2 | c-Hex | | C(O)N(Me)[C(O)(Me)₂CH₂OH] |
| Me | H | 4-Cl-Bn | R | 2 | 2 | c-Hex | | C(O)CH(Me)₂ |
| Me | H | 4-Cl-Bn | R | 2 | 2 | c-Hex | | C(O)C(Me)₃ |
| Me | Me | 4-Cl-Bn | R | 2 | 2 | c-Hex | | C(O)N(Et)₂ |
| Me | Me | 4-Cl-Bn | R | 2 | 2 | c-Hex | | C(O)N(Et)(CH₂)₂OH |
| Me | Me | 4-Cl-Bn | R | 2 | 2 | c-Hex | | C(O)N(c-Pr)(CH₂)₂OH |
| Me | Me | 4-Cl-Bn | R | 2 | 2 | c-Hex | | C(O)N(i-Pr)(CH₂)₂OH |
| Me | Me | 4-Cl-Bn | R | 2 | 2 | c-Hex | | C(O)N[(CH₂)₂OMe](CH₂)₂OH |
| Me | Me | 4-Cl-Bn | R | 2 | 2 | c-Hex | | C(O)N[(CH₂)₂OH]₂ |
| Me | Me | 4-Cl-Bn | R | 2 | 2 | c-Hex | | C(O)N[(CH₂)₂F](CH₂)₂OH |
| Me | Me | 4-Cl-Bn | R | 2 | 2 | c-Hex | | C(O)N(Me)(CH₂)₂OMe |
| Me | Me | 4-Cl-Bn | R | 2 | 2 | c-Hex | | C(O)N[(CH₂)₂F](CH₂)₂OMe |
| Me | Me | 4-Cl-Bn | R | 2 | 2 | c-Hex | | C(O)N(Et)(CH₂)₂F |
| Me | Me | 4-Cl-Bn | R | 2 | 2 | c-Hex | | C(O)N(Et)(CH₂)₃F |
| Me | Me | 4-Cl-Bn | R | 2 | 2 | c-Hex | | C(O)N(Et)(CH₂)₃OH |
| Me | Me | 4-Cl-Bn | R | 2 | 2 | c-Hex | | C(O)N[(CH₂)₂OMe](CH₂)₃OH |
| Me | Me | 4-F-Bn | R | 2 | 2 | c-Hex | | C(O)N(Et)₂ |
| Me | Me | 4-F-Bn | R | 2 | 2 | c-Hex | | C(O)N(Et)(CH₂)₂OH |
| Me | Me | 4-F-Bn | R | 2 | 2 | c-Hex | | C(O)N(i-Pr)(CH₂)₂OH |
| Me | Me | 4-F-Bn | R | 2 | 2 | c-Hex | | C(O)N[(CH₂)₂OH]₂ |
| Me | Me | 4-F-Bn | R | 2 | 2 | c-Hex | | C(O)N[(CH₂)₂F](CH₂)₂OMe |
| Me | Me | 4-F-Bn | R | 2 | 2 | c-Hex | | C(O)N(Et)(CH₂)₃OH |
| MeO₂C—CH₂ | H | 4-Cl-Bn | R | 2 | 2 | c-Hex | | C(O)CH(Me)₂ |
| HO₂C—CH₂ | H | 4-Cl-Bn | R | 2 | 2 | c-Hex | | C(O)CH(Me)₂ |
| N-diMe-Gly | H | 4-Cl-Bn | R | 2 | 2 | c-Hex | | C(O)CH(Me)₂ |
| (R)Ala | H | 4-Cl-Bn | R | 2 | 2 | c-Hex | | C(O)CH(Me)₂ |
| β-Ala | H | 4-Cl-Bn | R | 2 | 2 | c-Hex | | C(O)CH(Me)₂ |
| N-diMe-β-Ala | H | 4-Cl-Bn | R | 2 | 2 | c-Hex | | C(O)CH(Me)₂ |
| (S)His | H | 4-Cl-Bn | R | 2 | 2 | c-Hex | | C(O)CH(Me)₂ |
| (R)Pro | H | 4-Cl-Bn | R | 2 | 2 | c-Hex | | C(O)CH(Me)₂ |
| N-Me-(R)Pro | H | 4-Cl-Bn | R | 2 | 2 | c-Hex | | C(O)CH(Me)₂ |
| (R)Tic | H | 4-Cl-Bn | R | 2 | 2 | c-Hex | | C(O)CH(Me)₂ |
| MeO₂C—CH₂ | H | 4-Cl-Bn | R | 2 | 2 | c-Hex | | C(O)CH(Me)₂ |
| HO₂C—CH₂ | H | 4-Cl-Bn | R | 2 | 2 | c-Hex | | C(O)CH(Me)₂ |
| N-diMe-Gly | H | 4-Cl-Bn | R | 2 | 2 | c-Hex | | C(O)CH(Me)₂ |
| (R)Ala | H | 4-Cl-Bn | R | 2 | 2 | c-Hex | | C(O)CH(Me)₂ |
| β-Ala | H | 4-Cl-Bn | R | 2 | 2 | c-Hex | | C(O)CH(Me)₂ |
| N-diMe-β-Ala | H | 4-Cl-Bn | R | 2 | 2 | c-Hex | | C(O)CH(Me)₂ |
| (S)His | H | 4-Cl-Bn | R | 2 | 2 | c-Hex | | C(O)CH(Me)₂ |
| (R)Pro | H | 4-Cl-Bn | R | 2 | 2 | c-Hex | | C(O)CH(Me)₂ |
| N-Me-(R)Pro | H | 4-Cl-Bn | R | 2 | 2 | c-Hex | | C(O)CH(Me)₂ |
| (R)Tic | H | 4-Cl-Bn | R | 2 | 2 | c-Hex | | C(O)CH(Me)₂ |
| (R)Pyd-2-CH₂ | H | 4-Cl-Bn | R | 2 | 2 | c-Hex | | C(O)CH(Me)₂ |
| (R)Pyd-2-CH₂ | H | 4-Cl-Bn | R | 2 | 2 | c-Hex | | C(O)C(Me)₃ |
| (R)Pyd-2-CH₂ | H | 4-Cl-Bn | R | 2 | 2 | 2,3-diF—Ph | | C(O)CH(Me)₂ |
| (R)Pyd-2-CH₂ | H | 4-Cl-Bn | R | 2 | 2 | 2,4-diF—Ph | | C(O)CH(Me)₂ |
| (S)Pyd-2-CH₂ | H | 4-F-Bn | R | 2 | 2 | 2,3-diF—Ph | | C(O)CH(Me)₂ |
| (2R,4S)-4F-Pyd-2-CH₂ | H | 4-Cl-Bn | R | 2 | 2 | 2,3-diF—Ph | | C(O)CH(Me)₂ |
| (S)Pyd-2-CH₂ | H | 4-Cl-Bn | R | 2 | 2 | c-Hex | | C(O)CH(Me)₂ |
| (S)Pyd-2-CH₂ | H | 4-Cl-Bn | R | 2 | 2 | 2,3-diF—Ph | | C(O)CH(Me)₂ |
| (R)Pyd-2-CH₂— | H | 4-Cl-Bn | R | 2 | 2 | 2,3-diF—Ph | | C(O)C(Me)₂CH₂OH |
| (R)Pyd-2-CH₂— | H | 4-Cl-Bn | R | 2 | 2 | c-Hex | | C(O)C(Me)₂CH₂OH |
| (R)Pyd-2-CH₂ | H | 4-Cl-Bn | R | 2 | 2 | c-Hex | | C(O)N(Et)₂ |
| (R)Pyd-2-CH₂ | H | 4-Cl-Bn | R | 2 | 2 | c-Hex | | C(O)N(i-Pr)(CH₂)₂OH |
| (R)Pyd-2-CH₂ | H | 4-Cl-Bn | R | 2 | 2 | c-Hex | | C(O)N[(CH₂)₂OMe](CH₂)₂OH |
| (R)Pyd-2-CH₂ | H | 4-Cl-Bn | R | 2 | 2 | c-Hex | | C(O)N[(CH₂)₂F](CH₂)₂OH |
| (R)Pyd-2-CH₂ | H | 4-Cl-Bn | R | 2 | 2 | c-Hex | | C(O)N(Et)(CH₂)₂F |
| (R)Pyd-2-CH₂ | H | 4-Cl-Bn | R | 2 | 2 | c-Hex | | C(O)N(Et)(CH₂)₃OH |
| (R)Pyd-2-CH₂ | H | 4-Cl-Bn | R | 2 | 2 | c-Hex | | C(O)N(n-Pr)(CH₂)₂OH |
| (R)Pyd-2-CH₂ | H | 4-Cl-Bn | R | 2 | 2 | c-Hex | | C(O)N[(CH₂)₂OH]₂ |
| (R)Pyd-2-CH₂ | H | 4-Cl-Bn | R | 2 | 2 | c-Hex | | C(O)N(Me)OMe |
| (R)Pyd-2-CH₂ | H | 4-Cl-Bn | R | 2 | 2 | c-Hex | | C(O)N(Me)[C(Me)₂CH₂NH₂] |
| (R)Pyd-2-CH₂ | H | 4-Cl-Bn | R | 2 | 2 | c-Hex | | C(O)N(Et)(CH₂)₂OH |
| (R)Pyd-2-CH₂ | H | 4-Cl-Bn | R | 2 | 2 | c-Hex | | C(O)N[(CH₂)₂OMe]₂ |
| (R)Pyd-2-CH₂ | H | 4-Cl-Bn | R | 2 | 2 | c-Hex | | C(O)N(c-Pr)(CH₂)₂OH |
| (R)Pyd-2-CH₂ | H | 4-Cl-Bn | R | 2 | 2 | c-Hex | | C(O)[(3S)-3-(OH)-Pyd-1-yl] |

TABLE 1-continued

| R¹ | R² | R³ | *1 | n | m | R⁴ | *2 | R⁵ |
|---|---|---|---|---|---|---|---|---|
| (R)Pyd-2-CH₂ | H | 4-Cl-Bn | R | 2 | 2 | c-Hex | | C(O)[(2R)-2-(HOCH₂)-Pyd-1-yl] |
| (R)Pyd-2-CH₂ | H | 4-Cl-Bn | R | 2 | 2 | c-Hex | | C(O)[4-(OH)-Pid-1-yl] |
| (R)Pyd-2-CH₂ | H | 4-Cl-Bn | R | 2 | 2 | c-Hex | | C(O)[(3R)-3-(OH)-Pid-1-yl] |
| (R)Pyd-2-CH₂ | H | 4-F-Bn | R | 2 | 2 | c-Hex | | C(O)N(Et)₂ |
| (R)Pyd-2-CH₂ | H | 4-F-Bn | R | 2 | 2 | c-Hex | | C(O)N(i-Pr)(CH₂)₂OH |
| (R)Pyd-2-CH₂ | H | 4-F-Bn | R | 2 | 2 | c-Hex | | C(O)N[(CH₂)₂OH]₂ |
| (R)Pyd-2-CH₂ | H | 4-F-Bn | R | 2 | 2 | c-Hex | | C(O)N[(CH₂)₂F](CH₂)₂OMe |
| (R)Pyd-2-CH₂ | H | 4-F-Bn | R | 2 | 2 | c-Hex | | C(O)N(Et)(CH₂)₂F |
| (R)Pyd-2-CH₂ | H | 4-F-Bn | R | 2 | 2 | c-Hex | | C(O)N[(CH₂)₂OMe](CH₂)₂OH |
| (R)Pyd-2-CH₂ | H | 4-F-Bn | R | 2 | 2 | c-Hex | | C(O)[(3S)-3-(OH)-Pyd-1-yl] |
| (R)Pyd-2-CH₂ | H | 4-F-Bn | R | 2 | 2 | c-Hex | | C(O)[(2R)-2-(HOCH₂)-Pyd-1-yl] |
| (R)Pyd-2-CH₂ | H | 4-Cl-Bn | R | 2 | 2 | c-Hex | | N(Me)[C(Me)₂CH₂OH] |
| 1-Pyd-(CH₂)₂— | H | 4-Cl-Bn | R | 2 | 2 | c-Hex | | C(O)N(Et)₂ |
| 1-Pyd-(CH₂)₂— | H | 4-Cl-Bn | R | 2 | 2 | c-Hex | | C(O)N(Et)(CH₂)₂OH |
| 1-Pyd-(CH₂)₂— | H | 4-Cl-Bn | R | 2 | 2 | c-Hex | | C(O)N(c-Pr)(CH₂)₂OH |
| 1-Pyd-(CH₂)₂— | H | 4-Cl-Bn | R | 2 | 2 | c-Hex | | C(O)N(i-Pr)(CH₂)₂OH |
| 1-Pyd-(CH₂)₂— | H | 4-Cl-Bn | R | 2 | 2 | c-Hex | | C(O)N[(CH₂)₂OMe](CH₂)₂OH |
| 1-Pyd-(CH₂)₂— | H | 4-Cl-Bn | R | 2 | 2 | c-Hex | | C(O)N[(CH₂)₂OH]₂ |
| 1-Pyd-(CH₂)₂— | H | 4-Cl-Bn | R | 2 | 2 | c-Hex | | C(O)N[(CH₂)₂F](CH₂)₂OH |
| 1-Pyd-(CH₂)₂— | H | 4-Cl-Bn | R | 2 | 2 | c-Hex | | C(O)N(Me)(CH₂)₂OMe |
| 1-Pyd-(CH₂)₂— | H | 4-Cl-Bn | R | 2 | 2 | c-Hex | | C(O)N[(CH₂)₂F](CH₂)₂OMe |
| 1-Pyd-(CH₂)₂— | H | 4-Cl-Bn | R | 2 | 2 | c-Hex | | C(O)N(Et)(CH₂)₂F |
| 1-Pyd-(CH₂)₂— | H | 4-Cl-Bn | R | 2 | 2 | c-Hex | | C(O)N(Et)(CH₂)₃OH |
| 1-Pyd-(CH₂)₂— | H | 4-Cl-Bn | R | 2 | 2 | c-Hex | | C(O)N[(CH₂)₂OMe](CH₂)₃OH |
| 1-Pyd-(CH₂)₂— | H | 4-F-Bn | R | 2 | 2 | c-Hex | | C(O)N(Et)₂ |
| 1-Pyd-(CH₂)₂— | H | 4-F-Bn | R | 2 | 2 | c-Hex | | C(O)N(Et)(CH₂)₂OH |
| 1-Pyd-(CH₂)₂— | H | 4-F-Bn | R | 2 | 2 | c-Hex | | C(O)N(i-Pr)(CH₂)₂OH |
| 1-Pyd-(CH₂)₂— | H | 4-F-Bn | R | 2 | 2 | c-Hex | | C(O)N[(CH₂)₂OH]₂ |
| 1-Pyd-(CH₂)₂— | H | 4-F-Bn | R | 2 | 2 | c-Hex | | C(O)N[(CH₂)₂F](CH₂)₂OMe |
| 1-Pyd-(CH₂)₂— | H | 4-F-Bn | R | 2 | 2 | c-Hex | | C(O)N(Et)(CH₂)₃OH |
| 1-Pyd-(CH₂)₂— | H | 4-Cl-Bn | R | 2 | 2 | c-Hex | | C(O)N(Et)(CH₂)₃F |
| (R)-3-BnO-1-pyd-(CH₂)₂ | H | 4-Cl-Bn | R | 2 | 2 | c-Hex | | C(O)N(Et)(CH₂)₃F |
| (S)-3-BnO-1-pyd-(CH₂)₂ | H | 4-Cl-Bn | R | 2 | 2 | c-Hex | | C(O)N(Et)(CH₂)₃OH |
| (i-Pr)(Me)N—(CH₂)₂ | H | 4-F-Bn | R | 2 | 2 | c-Hex | | C(O)N(Et)(CH₂)₃F |
| NH₂—(CH₂)₂— | H | 4-Cl-Bn | R | 2 | 2 | c-Hex | | C(O)N[(CH₂)₂OH]₂ |
| (Me)NH—(CH₂)₂— | H | 4-Cl-Bn | R | 2 | 2 | c-Hex | | C(O)N[(CH₂)₂OH]₂ |
| (R)Pyd-2-CH₂ | H | 4-Cl-Bn | R | 2 | 2 | c-Hex | | C(O)CH(Me)₂ |
| (R)Pyd-2-CH₂ | H | 4-Cl-Bn | R | 2 | 2 | c-Hex | | C(O)C(Me)₃ |
| (R)Pyd-2-CH₂ | H | 4-Cl-Bn | R | 2 | 2 | 2,3-diF—Ph | | C(O)CH(Me)₂ |
| (R)Pyd-2-CH₂ | H | 4-Cl-Bn | R | 2 | 2 | 2,4-diF—Ph | | C(O)CH(Me)₂ |
| (S)Pyd-2-CH₂ | H | 4-F-Bn | R | 2 | 2 | 2,3-diF—Ph | | C(O)CH(Me)₂ |
| (2R,4S)-4F-Pyd-2-CH₂ | H | 4-Cl-Bn | R | 2 | 2 | 2,3-diF—Ph | | C(O)CH(Me)₂ |
| (S)Pyd-2-CH₂ | H | 4-Cl-Bn | R | 2 | 2 | c-Hex | | C(O)CH(Me)₂ |
| (S)Pyd-2-CH₂ | H | 4-Cl-Bn | R | 2 | 2 | 2,3-diF—Ph | | C(O)CH(Me)₂ |
| (S)Pyd-2-CH₂ | H | 4-Cl-Bn | R | 2 | 2 | 2,4-diF—Ph | | C(O)CH(Me)₂ |
| (R)Pyd-2-CH₂ | H | 4-Cl-Bn | R | 2 | 2 | 2,3-diF—Ph | | C(O)N(Me)(CH₂)₂OH |
| (R)Pyd-2-CH₂ | H | 4-Cl-Bn | R | 2 | 2 | 2,3-diF—Ph | | C(O)N(Me)(CH₂)₂OMe |
| (R)-1-Me-Pid-2-CH₂ | H | 4-Cl-Bn | R | 2 | 2 | c-Hex | | C(O)CH(Me)₂ |
| (S)-1-Me-Pid-3-CH₂ | H | 4-Cl-Bn | R | 2 | 2 | c-Hex | | C(O)CH(Me)₂ |
| (R)-1-Me-Pid-3-CH₂ | H | 4-Cl-Bn | R | 2 | 2 | c-Hex | | C(O)CH(Me)₂ |
| (R)Pyd-3-yl | H | 4-Cl-Bn | R | 2 | 2 | c-Hex | | C(O)CH(Me)₂ |
| (R)Pyd-3-yl | H | Bn | R | 2 | 2 | c-Hex | | C(O)CH(Me)₂ |
| (S)Pyd-3-yl | H | 4-Cl-Bn | R | 2 | 2 | c-Hex | | C(O)N(Et)₂ |
| (S)Pyd-3-yl | H | 4-Cl-Bn | R | 2 | 2 | c-Hex | | C(O)N(Me)(CH₂)₂OH |
| (S)Pyd-3-yl | H | 4-Cl-Bn | R | 2 | 2 | c-Hex | | C(O)N(Et)(CH₂)₂OH |
| 2-oxo-1-Pyd-(CH₂)₂— | H | 4-Cl-Bn | R | 2 | 2 | c-Hex | | C(O)N(Et)(CH₂)₂OH |
| 2-oxo-1-Pyd-(CH₂)₂— | H | 4-Cl-Bn | R | 2 | 2 | c-Hex | | C(O)N(Et)(CH₂)₃OH |
| 3-OH-1-Pyd-(CH₂)₂— | H | 4-Cl-Bn | R | 2 | 2 | c-Hex | | C(O)N(Et)(CH₂)₃F |
| 3-OH-1-Pyd-(CH₂)₂— | H | 4-Cl-Bn | R | 2 | 2 | c-Hex | | C(O)N(Et)(CH₂)₃OH |
| (i-Pr)HN—(CH₂)₂— | H | 4-Cl-Bn | R | 2 | 2 | c-Hex | | C(O)N(Et)(CH₂)₂OH |
| (i-Pr)HN—(CH₂)₂— | H | 4-Cl-Bn | R | 2 | 2 | c-Hex | | C(O)N(Et)₂ |
| (i-Pr)HN—(CH₂)₂— | H | 4-Cl-Bn | R | 2 | 2 | c-Hex | | C(O)N(c-Pr)(CH₂)₂OH |
| (i-Pr)HN—(CH₂)₂— | H | 4-Cl-Bn | R | 2 | 2 | c-Hex | | C(O)N(i-Pr)(CH₂)₂OH |
| (i-Pr)HN—(CH₂)₂— | H | 4-Cl-Bn | R | 2 | 2 | c-Hex | | C(O)N[(CH₂)₂OMe](CH₂)₂OH |
| (i-Pr)HN—(CH₂)₂— | H | 4-Cl-Bn | R | 2 | 2 | c-Hex | | C(O)N[(CH₂)₂OH]₂ |
| (i-Pr)HN—(CH₂)₂— | H | 4-Cl-Bn | R | 2 | 2 | c-Hex | | C(O)N[(CH₂)₂F](CH₂)₂OH |
| (i-Pr)HN—(CH₂)₂— | H | 4-Cl-Bn | R | 2 | 2 | c-Hex | | C(O)N(Me)(CH₂)₂OMe |
| (i-Pr)HN—(CH₂)₂— | H | 4-Cl-Bn | R | 2 | 2 | c-Hex | | C(O)N[(CH₂)₂F](CH₂)₂OMe |
| (i-Pr)HN—(CH₂)₂— | H | 4-Cl-Bn | R | 2 | 2 | c-Hex | | C(O)N(Et)(CH₂)₂F |
| (i-Pr)HN—(CH₂)₂— | H | 4-Cl-Bn | R | 2 | 2 | c-Hex | | C(O)N(Et)(CH₂)₃OH |
| (i-Pr)HN—(CH₂)₂— | H | 4-Cl-Bn | R | 2 | 2 | c-Hex | | C(O)N[(CH₂)₂OMe](CH₂)₃OH |
| (i-Pr)HN—(CH₂)₂— | H | 4-F-Bn | R | 2 | 2 | c-Hex | | C(O)N(Et)₂ |
| (i-Pr)HN—(CH₂)₂— | H | 4-F-Bn | R | 2 | 2 | c-Hex | | C(O)N(Et)(CH₂)₂OH |
| (i-Pr)HN—(CH₂)₂— | H | 4-F-Bn | R | 2 | 2 | c-Hex | | C(O)N(i-Pr)(CH₂)₂OH |
| (i-Pr)HN—(CH₂)₂— | H | 4-F-Bn | R | 2 | 2 | c-Hex | | C(O)N[(CH₂)₂OH]₂ |
| (i-Pr)HN—(CH₂)₂— | H | 4-F-Bn | R | 2 | 2 | c-Hex | | C(O)N[(CH₂)₂F](CH₂)₂OMe |
| (i-Pr)HN—(CH₂)₂— | H | 4-Cl-Bn | R | 2 | 2 | c-Hex | | C(O)N(Et)(CH₂)₃OH |
| (S)-3-OH-Pyd-1-(CH₂)₂ | H | 4-Cl-Bn | R | 2 | 2 | c-Hex | | N(Et)₂ |

TABLE 1-continued

| R¹ | R² | R³ | *1 | n | m | R⁴ | *2 | R⁵ |
|---|---|---|---|---|---|---|---|---|
| (S)-3-OH-Pyd-1-(CH$_2$)$_2$ | H | 4-Cl-Bn | R | 2 | 2 | c-Hex | | N(Et)(CH$_2$)$_2$OH |
| (S)-3-OH-Pyd-1-(CH$_2$)$_2$ | H | 4-Cl-Bn | R | 2 | 2 | c-Hex | | N(c-Pr)(CH$_2$)$_2$OH |
| (S)-3-OH-Pyd-1-(CH$_2$)$_2$ | H | 4-Cl-Bn | R | 2 | 2 | c-Hex | | N(i-Pr)(CH$_2$)$_2$OH |
| (S)-3-OH-Pyd-1-(CH$_2$)$_2$ | H | 4-Cl-Bn | R | 2 | 2 | c-Hex | | N[(CH$_2$)$_2$OMe](CH$_2$)$_2$OH |
| (S)-3-OH-Pyd-1-(CH$_2$)$_2$ | H | 4-Cl-Bn | R | 2 | 2 | c-Hex | | N[(CH$_2$)$_2$OH]$_2$ |
| (S)-3-OH-Pyd-1-(CH$_2$)$_2$ | H | 4-Cl-Bn | R | 2 | 2 | c-Hex | | N[(CH$_2$)$_2$F](CH$_2$)$_2$OH |
| (S)-3-OH-Pyd-1-(CH$_2$)$_2$ | H | 4-Cl-Bn | R | 2 | 2 | c-Hex | | N(Me)(CH$_2$)$_2$OMe |
| (S)-3-OH-Pyd-1-(CH$_2$)$_2$ | H | 4-Cl-Bn | R | 2 | 2 | c-Hex | | N[(CH$_2$)$_2$F](CH$_2$)$_2$OMe |
| (S)-3-OH-Pyd-1-(CH$_2$)$_2$ | H | 4-Cl-Bn | R | 2 | 2 | c-Hex | | N(Et)(CH$_2$)$_3$F |
| (S)-3-OH-Pyd-1-(CH$_2$)$_2$ | H | 4-Cl-Bn | R | 2 | 2 | c-Hex | | N(Et)(CH$_2$)$_2$F |
| (S)-3-OH-Pyd-1-(CH$_2$)$_2$ | H | 4-Cl-Bn | R | 2 | 2 | c-Hex | | N(Et)(CH$_2$)$_3$OH |
| (S)-3-OH-Pyd-1-(CH$_2$)$_2$ | H | 4-Cl-Bn | R | 2 | 2 | c-Hex | | N[(CH$_2$)$_2$OMe](CH$_2$)$_3$OH |
| (S)-3-OH-Pyd-1-(CH$_2$)$_2$ | H | 4-F-Bn | R | 2 | 2 | c-Hex | | N(Et)$_2$ |
| (S)-3-OH-Pyd-1-(CH$_2$)$_2$ | H | 4-F-Bn | R | 2 | 2 | c-Hex | | N(Et)(CH$_2$)$_2$OH |
| (S)-3-OH-Pyd-1-(CH$_2$)$_2$ | H | 4-F-Bn | R | 2 | 2 | c-Hex | | N(i-Pr)(CH$_2$)$_2$OH |
| (S)-3-OH-Pyd-1-(CH$_2$)$_2$ | H | 4-F-Bn | R | 2 | 2 | c-Hex | | N[(CH$_2$)$_2$OH]$_2$ |
| (S)-3-OH-Pyd-1-(CH$_2$)$_2$ | H | 4-F-Bn | R | 2 | 2 | c-Hex | | N[(CH$_2$)$_2$F](CH$_2$)$_2$OMe |
| (S)-3-OH-Pyd-1-(CH$_2$)$_2$ | H | 4-F-Bn | R | 2 | 2 | c-Hex | | N(Et)(CH$_2$)$_3$OH |
| (R)-3-OH-Pyd-1-(CH$_2$)$_2$ | H | 4-Cl-Bn | R | 2 | 2 | c-Hex | | N(Et)$_2$ |
| (R)-3-OH-Pyd-1-(CH$_2$)$_2$ | H | 4-Cl-Bn | R | 2 | 2 | c-Hex | | N(Et)(CH$_2$)$_2$OH |
| (R)-3-OH-Pyd-1-(CH$_2$)$_2$ | H | 4-Cl-Bn | R | 2 | 2 | c-Hex | | N(c-Pr)(CH$_2$)$_2$OH |
| (R)-3-OH-Pyd-1-(CH$_2$)$_2$ | H | 4-Cl-Bn | R | 2 | 2 | c-Hex | | N(i-Pr)(CH$_2$)$_2$OH |
| (R)-3-OH-Pyd-1-(CH$_2$)$_2$ | H | 4-Cl-Bn | R | 2 | 2 | c-Hex | | N[(CH$_2$)$_2$OMe](CH$_2$)$_2$OH |
| (R)-3-OH-Pyd-1-(CH$_2$)$_2$ | H | 4-Cl-Bn | R | 2 | 2 | c-Hex | | N[(CH$_2$)$_2$OH]$_2$ |
| (R)-3-OH-Pyd-1-(CH$_2$)$_2$ | H | 4-Cl-Bn | R | 2 | 2 | c-Hex | | N[(CH$_2$)$_2$F](CH$_2$)$_2$OH |
| (R)-3-OH-Pyd-1-(CH$_2$)$_2$ | H | 4-Cl-Bn | R | 2 | 2 | c-Hex | | N(Me)(CH$_2$)$_2$OMe |
| (R)-3-OH-Pyd-1-(CH$_2$)$_2$ | H | 4-Cl-Bn | R | 2 | 2 | c-Hex | | N[(CH$_2$)$_2$F](CH$_2$)$_2$OMe |
| (R)-3-OH-Pyd-1-(CH$_2$)$_2$ | H | 4-Cl-Bn | R | 2 | 2 | c-Hex | | N(Et)(CH$_2$)$_3$F |
| (R)-3-OH-Pyd-1-(CH$_2$)$_2$ | H | 4-Cl-Bn | R | 2 | 2 | c-Hex | | N(Et)(CH$_2$)$_2$F |
| (R)-3-OH-Pyd-1-(CH$_2$)$_2$ | H | 4-Cl-Bn | R | 2 | 2 | c-Hex | | N(Et)(CH$_2$)$_3$OH |
| (R)-3-OH-Pyd-1-(CH$_2$)$_2$ | H | 4-Cl-Bn | R | 2 | 2 | c-Hex | | N[(CH$_2$)$_2$OMe](CH$_2$)$_3$OH |
| (R)-3-OH-Pyd-1-(CH$_2$)$_2$ | H | 4-F-Bn | R | 2 | 2 | c-Hex | | N(Et)$_2$ |
| (R)-3-OH-Pyd-1-(CH$_2$)$_2$ | H | 4-F-Bn | R | 2 | 2 | c-Hex | | N(Et)(CH$_2$)$_2$OH |
| (R)-3-OH-Pyd-1-(CH$_2$)$_2$ | H | 4-F-Bn | R | 2 | 2 | c-Hex | | N(i-Pr)(CH$_2$)$_2$OH |
| (R)-3-OH-Pyd-1-(CH$_2$)$_2$ | H | 4-F-Bn | R | 2 | 2 | c-Hex | | N[(CH$_2$)$_2$OH]$_2$ |
| (R)-3-OH-Pyd-1-(CH$_2$)$_2$ | H | 4-F-Bn | R | 2 | 2 | c-Hex | | N[(CH$_2$)$_2$F](CH$_2$)$_2$OMe |
| (R)-3-OH-Pyd-1-(CH$_2$)$_2$ | H | 4-F-Bn | R | 2 | 2 | c-Hex | | N(Et)(CH$_2$)$_3$OH |
| 2-oxo-1-pyd--(CH$_2$)$_2$— | H | 4-Cl-Bn | R | 2 | 2 | c-Hex | | N(Et)$_2$ |
| 2-oxo-1-pyd--(CH$_2$)$_2$— | H | 4-Cl-Bn | R | 2 | 2 | c-Hex | | N(Et)(CH$_2$)$_2$OH |
| 2-oxo-1-pyd--(CH$_2$)$_2$— | H | 4-Cl-Bn | R | 2 | 2 | c-Hex | | N(c-Pr)(CH$_2$)$_2$OH |
| 2-oxo-1-pyd--(CH$_2$)$_2$— | H | 4-Cl-Bn | R | 2 | 2 | c-Hex | | N(i-Pr)(CH$_2$)$_2$OH |
| 2-oxo-1-pyd--(CH$_2$)$_2$— | H | 4-Cl-Bn | R | 2 | 2 | c-Hex | | N[(CH$_2$)$_2$OMe](CH$_2$)$_2$OH |
| 2-oxo-1-pyd--(CH$_2$)$_2$— | H | 4-Cl-Bn | R | 2 | 2 | c-Hex | | N[(CH$_2$)$_2$OH]$_2$ |
| 2-oxo-1-pyd--(CH$_2$)$_2$— | H | 4-Cl-Bn | R | 2 | 2 | c-Hex | | N[(CH$_2$)$_2$F](CH$_2$)$_2$OH |
| 2-oxo-1-pyd--(CH$_2$)$_2$— | H | 4-Cl-Bn | R | 2 | 2 | c-Hex | | N(Me)(CH$_2$)$_2$OMe |
| 2-oxo-1-pyd--(CH$_2$)$_2$— | H | 4-Cl-Bn | R | 2 | 2 | c-Hex | | N[(CH$_2$)$_2$F](CH$_2$)$_2$OMe |
| 2-oxo-1-pyd--(CH$_2$)$_2$— | H | 4-Cl-Bn | R | 2 | 2 | c-Hex | | N(Et)(CH$_2$)$_3$F |
| 2-oxo-1-pyd--(CH$_2$)$_2$— | H | 4-Cl-Bn | R | 2 | 2 | c-Hex | | N(Et)(CH$_2$)$_2$F |
| 2-oxo-1-pyd--(CH$_2$)$_2$— | H | 4-Cl-Bn | R | 2 | 2 | c-Hex | | N(Et)(CH$_2$)$_2$OH |
| 2-oxo-1-pyd--(CH$_2$)$_2$— | H | 4-Cl-Bn | R | 2 | 2 | c-Hex | | N(Et)(CH$_2$)$_3$OH |
| 2-oxo-1-pyd--(CH$_2$)$_2$— | H | 4-Cl-Bn | R | 2 | 2 | c-Hex | | N[(CH$_2$)$_2$OMe](CH$_2$)$_3$OH |
| 2-oxo-1-pyd--(CH$_2$)$_2$— | H | 4-F-Bn | R | 2 | 2 | c-Hex | | N(Et)$_2$ |
| 2-oxo-1-pyd--(CH$_2$)$_2$— | H | 4-F-Bn | R | 2 | 2 | c-Hex | | N(Et)(CH$_2$)$_2$OH |
| 2-oxo-1-pyd--(CH$_2$)$_2$— | H | 4-F-Bn | R | 2 | 2 | c-Hex | | N(i-Pr)(CH$_2$)$_2$OH |
| 2-oxo-1-pyd--(CH$_2$)$_2$— | H | 4-F-Bn | R | 2 | 2 | c-Hex | | N[(CH$_2$)$_2$OH]$_2$ |
| 2-oxo-1-pyd--(CH$_2$)$_2$— | H | 4-F-Bn | R | 2 | 2 | c-Hex | | N[(CH$_2$)$_2$F](CH$_2$)$_2$OMe |
| 2-oxo-1-pyd--(CH$_2$)$_2$— | H | 4-F-Bn | R | 2 | 2 | c-Hex | | N(Et)(CH$_2$)$_3$OH |
| Mor-(CH$_2$)$_2$— | H | 4-Cl-Bn | R | 2 | 2 | c-Hex | | C(O)N(c-Pr)(CH$_2$)$_2$OH |
| Mor-(CH$_2$)$_2$— | H | 4-Cl-Bn | R | 2 | 2 | c-Hex | | C(O)N(Et)(CH$_2$)$_2$OH |
| Mor-(CH$_2$)$_2$— | H | 4-Cl-Bn | R | 2 | 2 | c-Hex | | C O N[(CH$_2$)$_2$OMe]$_2$ |
| Mor-(CH$_2$)$_2$— | H | 4-Cl-Bn | R | 2 | 2 | c-Hex | | C(O)N[(CH$_2$)$_2$OH]$_2$ |
| Mor-(CH$_2$)$_2$— | H | 4-Cl-Bn | R | 2 | 2 | c-Hex | | C(O)N[(CH$_2$)$_2$F](CH$_2$)$_2$OH |
| Mor-(CH$_2$)$_2$— | H | 4-Cl-Bn | R | 2 | 2 | c-Hex | | C(O)N(Me)(CH$_2$)$_2$OMe |
| Mor-(CH$_2$)$_2$— | H | 4-Cl-Bn | R | 2 | 2 | c-Hex | | C(O)N[(CH$_2$)$_2$F](CH$_2$)$_2$OMe |
| Mor-(CH$_2$)$_2$— | H | 4-Cl-Bn | R | 2 | 2 | c-Hex | | C(O)N(Et)(CH$_2$)$_2$F |
| Mor-(CH$_2$)$_2$— | H | 4-F-Bn | R | 2 | 2 | c-Hex | | C(O)N(Et)(CH$_2$)$_2$OH |
| Mor-(CH$_2$)$_2$— | H | 4-F-Bn | R | 2 | 2 | c-Hex | | C(O)N(i-Pr)(CH$_2$)$_2$OH |
| Mor-(CH$_2$)$_2$— | H | 4-F-Bn | R | 2 | 2 | c-Hex | | C(O)N[(CH$_2$)$_2$OH]$_2$ |
| NH$_2$—(CH$_2$)$_2$— | H | 4-Cl-Bn | R | 2 | 2 | c-Hex | | C(O)CH(Me)$_2$ |
| (Me)$_2$N—(CH$_2$)$_2$— | H | 4-Cl-Bn | R | 2 | 2 | c-Hex | | C(O)CH(Me)$_2$ |
| (Me)$_2$N—(CH$_2$)$_2$— | H | 4-Cl-Bn | R | 2 | 2 | c-Hex | | C(O)N(Me)OMe |
| (Me)$_2$N—(CH$_2$)$_2$— | H | 4-Cl-Bn | R | 2 | 2 | c-Hex | | C(O)N(Et)(CH$_2$)$_2$—OH |
| (Me)$_2$N—(CH$_2$)$_2$— | H | 4-Cl-Bn | R | 2 | 2 | c-Hex | | C(O)N(n-Pr)(CH$_2$)$_2$—OH |
| (Me)$_2$N—(CH$_2$)$_2$— | H | 4-Cl-Bn | R | 2 | 2 | c-Hex | | C(O)N[(CH$_2$)$_2$—OH]$_2$ |
| (Me)$_2$N—(CH$_2$)$_2$— | H | 4-Cl-Bn | R | 2 | 2 | c-Hex | | C(O)N[(CH$_2$)$_2$—OMe]$_2$ |
| (Me)$_2$N—(CH$_2$)$_2$— | H | 4-Cl-Bn | R | 2 | 2 | c-Hex | | C(O)[(2R)-2-(HOCH$_2$)-Pyd-1-yl] |
| (Me)$_2$N—(CH$_2$)$_2$— | H | 4-Cl-Bn | R | 2 | 2 | c-Hex | | C(O)(4-amino-Pid-1-yl) |
| (Me)$_2$N—(CH$_2$)$_2$— | H | 4-Cl-Bn | R | 2 | 2 | c-Hex | | C(O)N(Me)(CH$_2$)$_2$—OH |

TABLE 1-continued

| R¹ | R² | R³ | *1 | n | m | R⁴ | *2 | R⁵ |
|---|---|---|---|---|---|---|---|---|
| $(Me)_2N-(CH_2)_2-$ | H | 4-Cl-Bn | R | 2 | 2 | c-Hex | | $C(O)N(Me)(CH_2)_2-OMe$ |
| $(Me)_2N-(CH_2)_2-$ | H | 4-Cl-Bn | R | 2 | 2 | c-Hex | | $C(O)N(Et)_2$ |
| $(Me)_2N-(CH_2)_2-$ | H | 4-Cl-Bn | R | 2 | 2 | c-Hex | | $C(O)N(i-Pr)(CH_2)_2OH$ |
| $(Me)_2N-(CH_2)_2-$ | H | 4-Cl-Bn | R | 2 | 2 | c-Hex | | $C(O)N[(CH_2)_2OMe](CH_2)_2OH$ |
| $(Me)_2N-(CH_2)_2-$ | H | 4-Cl-Bn | R | 2 | 2 | c-Hex | | $C(O)N[(CH_2)_2F](CH_2)_2OH$ |
| $(Me)_2N-(CH_2)_2-$ | H | 4-Cl-Bn | R | 2 | 2 | c-Hex | | $C(O)N(Et)(CH_2)_2F$ |
| $(Me)_2N-(CH_2)_2-$ | H | 4-Cl-Bn | R | 2 | 2 | c-Hex | | $C(O)N(Et)(CH_2)_3OH$ |
| $(Me)_2N-(CH_2)_2-$ | H | 4-F-Bn | R | 2 | 2 | c-Hex | | $C(O)N(Me)OMe$ |
| $(Me)_2N-(CH_2)_2-$ | H | 4-F-Bn | R | 2 | 2 | c-Hex | | $C(O)N(Et)(CH_2)_2-OH$ |
| $(Me)_2N-(CH_2)_2-$ | H | 4-F-Bn | R | 2 | 2 | c-Hex | | $C(O)N(n-Pr)(CH_2)_2-OH$ |
| $(Me)_2N-(CH_2)_2-$ | H | 4-F-Bn | R | 2 | 2 | c-Hex | | $C(O)N[(CH_2)_2-OH]_2$ |
| $(Me)_2N-(CH_2)_2-$ | H | 4-F-Bn | R | 2 | 2 | c-Hex | | $C(O)N[(CH_2)_2-OMe]_2$ |
| $(Me)_2N-(CH_2)_2-$ | H | 4-F-Bn | R | 2 | 2 | c-Hex | | $C(O)N(i-Pr)(CH_2)_2OH$ |
| $(Me)_2N-(CH_2)_2-$ | H | 4-F-Bn | R | 2 | 2 | c-Hex | | $C(O)N[(CH_2)_2OMe](CH_2)_2OH$ |
| $(Me)_2N-(CH_2)_2-$ | H | 4-F-Bn | R | 2 | 2 | c-Hex | | $C(O)N[(CH_2)_2F](CH_2)_2OH$ |
| $(Me)_2N-(CH_2)_2-$ | H | 4-F-Bn | R | 2 | 2 | c-Hex | | $C(O)N(Et)(CH_2)_2F$ |
| $(Me)_2N-(CH_2)_2-$ | H | 4-F-Bn | R | 2 | 2 | c-Hex | | $C(O)N(Et)(CH_2)_3OH$ |
| $(Et)_2N-(CH_2)_2-$ | H | 4-Cl-Bn | R | 2 | 2 | c-Hex | | $C(O)N(Et)(CH_2)_3OH$ |
| $(Et)_2N-(CH_2)_2-$ | H | 4-Cl-Bn | R | 2 | 2 | c-Hex | | $C(O)N(Et)(CH_2)_2-OH$ |
| $(Et)_2N-(CH_2)_2-$ | H | 4-Cl-Bn | R | 2 | 2 | c-Hex | | $C(O)N(n-Pr)(CH_2)_2-OH$ |
| $(Et)_2N-(CH_2)_2-$ | H | 4-Cl-Bn | R | 2 | 2 | c-Hex | | $C(O)N[(CH_2)_2-OH]_2$ |
| $(Et)_2N-(CH_2)_2-$ | H | 4-Cl-Bn | R | 2 | 2 | c-Hex | | $C(O)N[(CH_2)_2-OMe]_2$ |
| $(Et)_2N-(CH_2)_2-$ | H | 4-Cl-Bn | R | 2 | 2 | c-Hex | | $C(O)N(i-Pr)(CH_2)_2OH$ |
| $(Et)_2N-(CH_2)_2-$ | H | 4-Cl-Bn | R | 2 | 2 | c-Hex | | $C(O)N[(CH_2)_2OMe](CH_2)_2OH$ |
| $(Et)_2N-(CH_2)_2-$ | H | 4-Cl-Bn | R | 2 | 2 | c-Hex | | $C(O)N[(CH_2)_2F](CH_2)_2OH$ |
| $(Et)_2N-(CH_2)_2-$ | H | 4-Cl-Bn | R | 2 | 2 | c-Hex | | $C(O)N(Et)(CH_2)_2F$ |
| $(Et)_2N-(CH_2)_2-$ | H | 4-F-Bn | R | 2 | 2 | c-Hex | | $C(O)N(Et)(CH_2)_3OH$ |
| $(Et)_2N-(CH_2)_2-$ | H | 4-F-Bn | R | 2 | 2 | c-Hex | | $C(O)N(Et)(CH_2)_2-OH$ |
| $(Et)_2N-(CH_2)_2-$ | H | 4-F-Bn | R | 2 | 2 | c-Hex | | $C(O)N(n-Pr)(CH_2)_2-OH$ |
| $(Et)_2N-(CH_2)_2-$ | H | 4-F-Bn | R | 2 | 2 | c-Hex | | $C(O)N[(CH_2)_2-OH]_2$ |
| $(Et)_2N-(CH_2)_2-$ | H | 4-F-Bn | R | 2 | 2 | c-Hex | | $C(O)N[(CH_2)_2-OMe]_2$ |
| $(Et)_2N-(CH_2)_2-$ | H | 4-F-Bn | R | 2 | 2 | c-Hex | | $C(O)N(i-Pr)(CH_2)_2OH$ |
| $(Et)_2N-(CH_2)_2-$ | H | 4-F-Bn | R | 2 | 2 | c-Hex | | $C(O)N[(CH_2)_2OMe](CH_2)_2OH$ |
| H | H | 4-Cl-Bn | R | 1 | 1 | c-Hex | | $C(O)CH(Me)_2$ |
| H | H | 4-Cl-Bn | R | 1 | 1 | c-Hex | | $C(O)C(Me)_3$ |
| H | H | 4-Cl-Bn | R | 1 | 1 | c-Hex | | $C(O)OMe$ |
| H | H | 4-Cl-Bn | R | 1 | 1 | c-Hex | | $C(O)N(Me)_2$ |
| H | H | 4-Cl-Bn | R | 1 | 1 | c-Hex | | $S(O)_2Me$ |
| H | H | 4-Cl-Bn | R | 1 | 1 | c-Pen | | $C(O)CH(Me)_2$ |
| H | H | 4-Cl-Bn | R | 1 | 1 | c-Hep | | $C(O)CH(Me)_2$ |
| H | H | 4-Cl-Bn | R | 1 | 1 | i-Pr | | $C(O)CH(Me)_2$ |
| H | H | 4-Cl-Bn | R | 1 | 1 | (c-Hex)Me | | $C(O)CH(Me)_2$ |
| H | H | 4-Cl-Bn | R | 1 | 1 | 2-Me-(c-Hex) | | $C(O)CH(Me)_2$ |
| H | H | 4-Cl-Bn | R | 1 | 1 | i-Bu | | $C(O)CH(Me)_2$ |
| $MeO_2C-CH_2$ | H | 4-Cl-Bn | R | 1 | 1 | c-Hex | | $C(O)CH(Me)_2$ |
| $HO_2C-CH_2$ | H | 4-Cl-Bn | R | 1 | 1 | c-Hex | | $C(O)CH(Me)_2$ |
| Gly | H | 4-Cl-Bn | R | 1 | 1 | c-Hex | | $C(O)CH(Me)_2$ |
| N-diMe-Gly | H | 4-Cl-Bn | R | 1 | 1 | c-Hex | | $C(O)CH(Me)_2$ |
| (S)His | H | 4-Cl-Bn | R | 1 | 1 | c-Hex | | $C(O)CH(Me)_2$ |
| N-BOC-(S)His | H | 4-Cl-Bn | R | 1 | 1 | c-Hex | | $C(O)CH(Me)_2$ |
| (R)Pro | H | 4-Cl-Bn | R | 1 | 1 | c-Hex | | $C(O)CH(Me)_2$ |
| N-Me-(R)Pro | H | 4-Cl-Bn | R | 1 | 1 | c-Hex | | $C(O)CH(Me)_2$ |
| (S)Pro | H | 4-Cl-Bn | R | 1 | 1 | c-Hex | | $C(O)CH(Me)_2$ |
| (R)Pid-2-CO | H | 4-Cl-Bn | R | 1 | 1 | c-Hex | | $C(O)CH(Me)_2$ |
| N-Me-(R)Pid-2-CO | H | 4-Cl-Bn | R | 1 | 1 | c-Hex | | $C(O)CH(Me)_2$ |
| (R)Tic | H | 4-Cl-Bn | R | 1 | 1 | c-Hex | | $C(O)CH(Me)_2$ |
| (R)Pyd-2-CH₂ | H | 4-Cl-Bn | R | 1 | 1 | c-Hex | | $C(O)CH(Me)_2$ |
| Pyd-1-(CH₂)₂ | H | 4-Cl-Bn | R | 1 | 1 | c-Hex | | $C(O)CH(Me)_2$ |
| (R)-1-Me-Pid-2-CH₂ | H | 4-Cl-Bn | R | 1 | 1 | c-Hex | | $C(O)CH(Me)_2$ |
| $(Me)_2N-(CH_2)_2$ | H | 4-Cl-Bn | R | 1 | 1 | c-Hex | | $C(O)CH(Me)_2$ |
| (R)-Pid-2-CH₂ | H | 4-Cl-Bn | R | 1 | 1 | c-Hex | | $C(O)CH(Me)_2$ |
| $(Me)_2N-(CH_2)_2$ | H | 4-Cl-Bn | R | 1 | 1 | c-Hex | | $C(O)C(Me)_3$ |
| 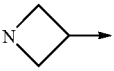 | H | 4-Cl-Bn | R | 1 | 1 | c-Hex | | $C(O)CH(Me)_2$ |

The compounds according to the present invention also can form pharmaceutically acceptable salts. These pharmaceutically acceptable salts include acid forming non-toxic acid addition salt containing pharmaceutically acceptable anion, for example, inorganic acids such as hydrochloric acid, sulfuric acid, nitric acid, phosphoric acid, hydrobromic acid, hydroiodic acid, and the like; organic carboxylic acid such as tartaric, formic, citric, acetic, trichloroacetic, trifluoroacetic, gluconic, benzoic, lactic, fumaric, maleic, and the like; acid-addition salts formed by sulfonic acid such as methanesulfonic acid, benzenesulfonic acid, p-toluenesulfonic acid or naphthalenesulfonic acid, and the like; preferably, acid-addition salts formed by sulfuric acid, methansulfonic acid or hydrohalic acid, and the like. The compounds of formula 1 according to the present invention can be converted to its salts by customary method.

Also, the compounds according to the present invention can have asymmetric carbon center, and so can be present as R or S isomeric forms, racemates, diastereomeric mixtures, and individual diastereomers. The present invention encompasses all these isomeric forms and mixtures.

The compounds according to the present invention can be prepared according to the procedures explained in the following Schemes 1-9. In the following Schemes, compounds of general formula (3), (6), (11), (12), (13), (14), (17), (18), (22), (24), (40) and (43) represent representative compounds of formula 1.

Compounds of formula (3) can be prepared by coupling protected amino acids (1) (P represents protecting groups, such as BOC, Cbz, Fmoc, etc.) with substituted amino-cyclic amine derivatives (2) (cyclic amine represent pyrrolidine, piperidine, or azetidine) under standard peptide coupling conditions, as illustrated in Scheme 1. The protected amino acids (1), starting materials, are either commercially available or may be prepared by known methods (Williams, R. M., Synthesis of Optically Active a-Amino Acids, Pergamon Press: Oxford, 1989). Similarly, the amino-cyclic amine derivatives (2) can be prepared following literature methods described for analogous compounds.

Scheme 1

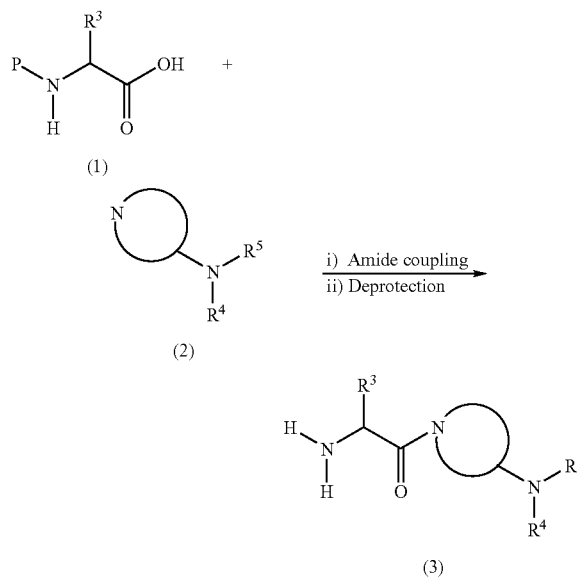

Compounds of formula (6) may be prepared by coupling N-substituted amino acid derivatives (5) with amino-cyclic amine derivatives (2), as illustrated in Scheme 2. Alkyl, acyl, or sulfonyl substituted amino acid derivatives (5) can be converted to amino acid derivatives (6) by hydrolysis in the presence of base.

Scheme 2

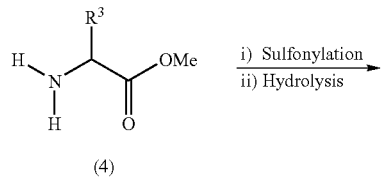

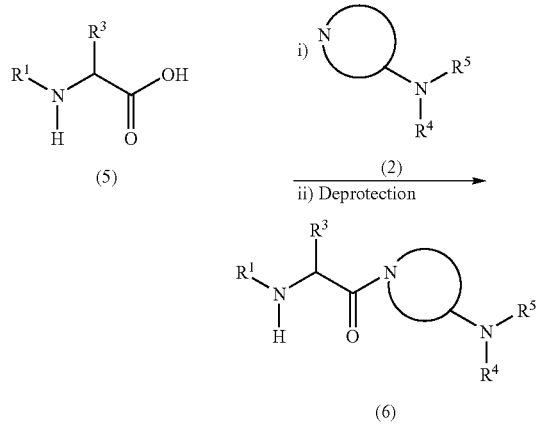

Compounds of formula (10), (11), (12), and (14) may be prepared by coupling protected amino acid derivatives (7), (8), (9), and (10) with the compounds of formula (3) as shown in Scheme 3 [Cy in compound (8) represents pyrrolidine, azetidine, aziridine, piperidine, etc.]. Protected amino acid derivatives (7), (8) and (9) are either commercially available or can be prepared by general protection reaction from various amino acids.

Scheme 3

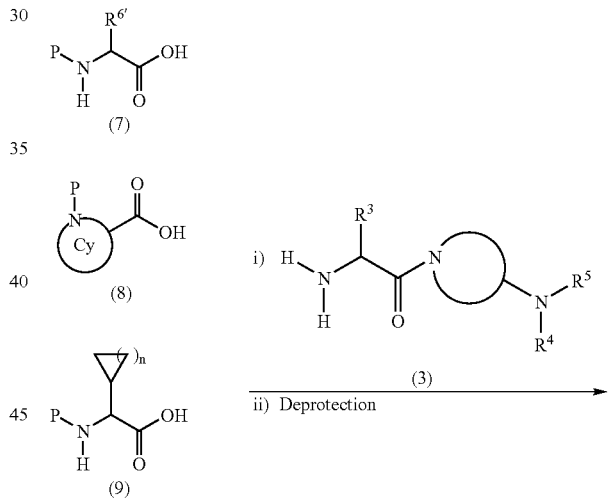

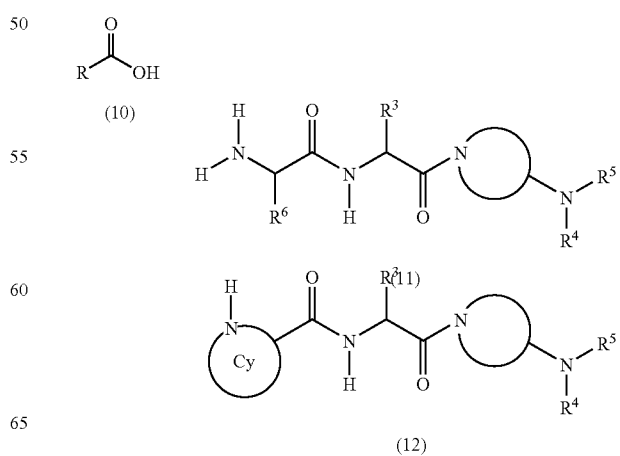

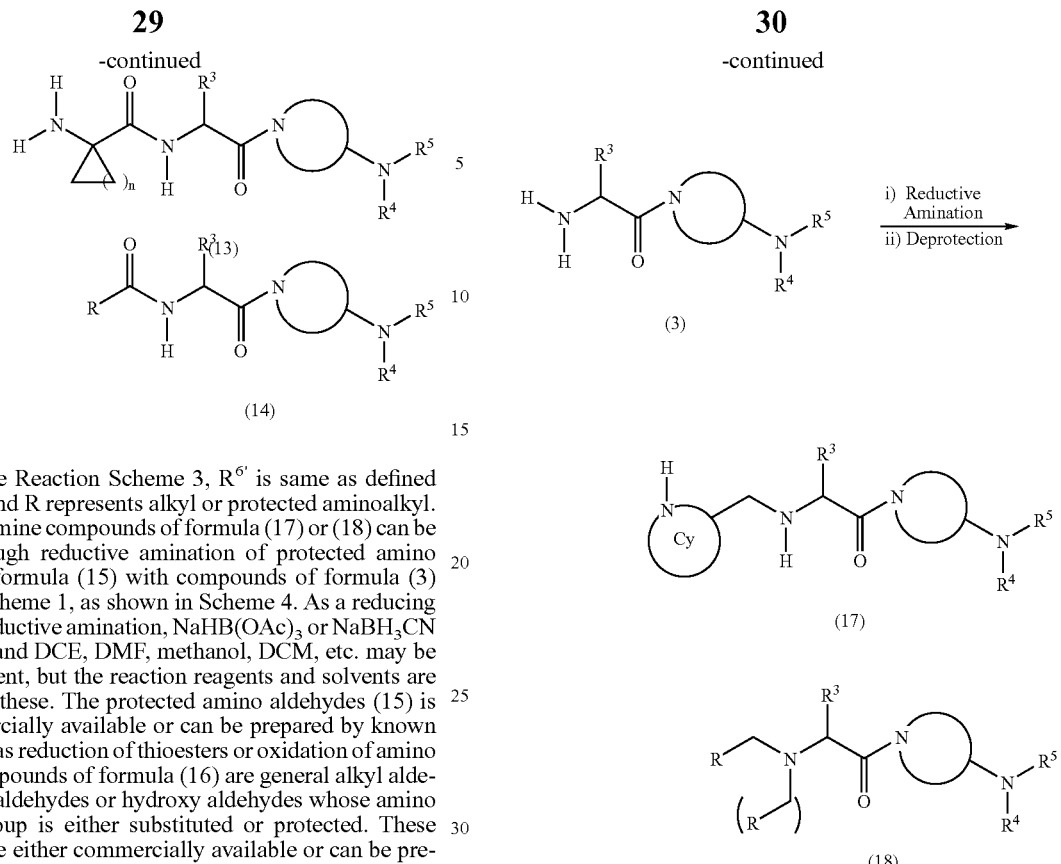

In the above Reaction Scheme 3, $R^{6'}$ is same as defined above in $R^6$, and R represents alkyl or protected aminoalkyl.

Alkylated amine compounds of formula (17) or (18) can be prepared through reductive amination of protected amino aldehydes of formula (15) with compounds of formula (3) prepared in Scheme 1, as shown in Scheme 4. As a reducing agent in the reductive amination, $NaHB(OAc)_3$ or $NaBH_3CN$ may be used, and DCE, DMF, methanol, DCM, etc. may be used as a solvent, but the reaction reagents and solvents are not limited to these. The protected amino aldehydes (15) is either commercially available or can be prepared by known methods such as reduction of thioesters or oxidation of amino alcohols. Compounds of formula (16) are general alkyl aldehydes, amino aldehydes or hydroxy aldehydes whose amino or alcohol group is either substituted or protected. These compounds are either commercially available or can be prepared by protection reaction. Mono- or di-substituted compounds (18) can be prepared by reductive amination and deprotection.

Scheme 4

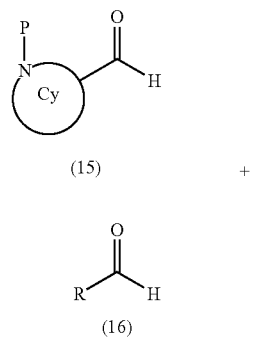

Compounds of formula (22), (23) and (24) can be prepared as shown in the following Scheme 5. Nitrobenzenesulfonyl protected intermediates of formula (19) can be converted to the compounds of formula (21) by alkylation or reductive amination (*Tetrahedron Lett.*, 1995, 36, 6373-6374). In compounds of formula (20) such as dimethylaminoethylchloride or N-BOC-2-aminoethyl-chloride, Q represents aminoalkyl or alkylated aminoalkyl, and X represents halogen. Compounds of formula (23) can be prepared through reductive amination of compounds of formula (21) and then converted into the compounds of formula (24) by alkylation.

Scheme 5

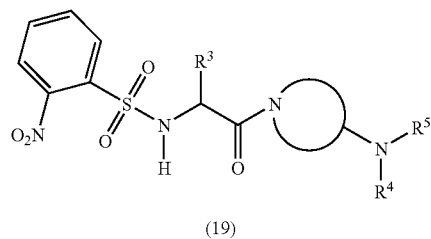

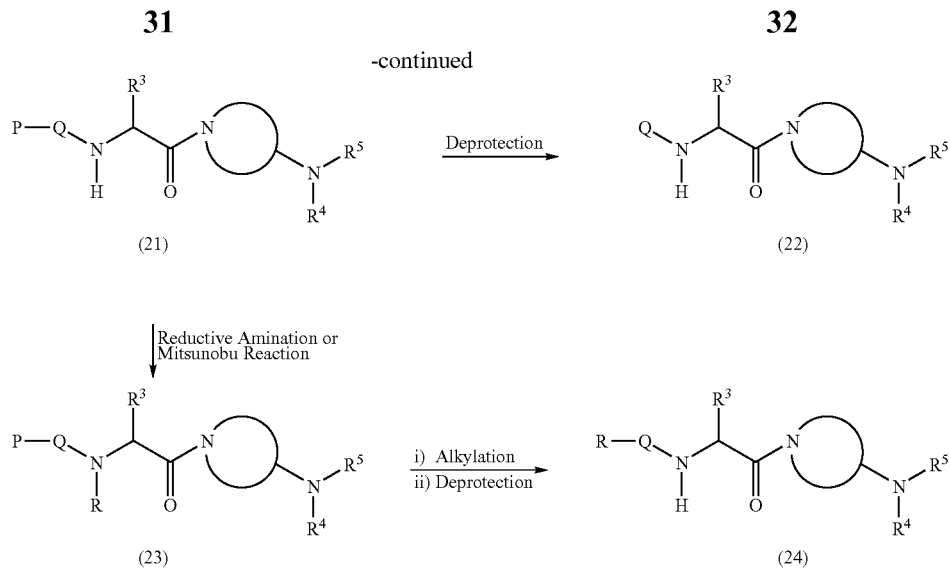

3-Disubstituted amino pyrrolidine derivatives (30) can be prepared as illustrated in Scheme 6. Compound (26) prepared from the commercially available compound (25) can be converted to compounds of formula (28) by reductive amination. Compounds of formula (30) can be prepared by acylation, amide coupling, or alkylation of compounds formula (28), and removing cbz group. Compounds of formula (30) can also be prepared from compound (31) using the similar method illustrated in Scheme 7.

4-Disubstituted piperidine derivatives (35) can be prepared as illustrated in Scheme 7. Compounds of formula (34) can be prepared by introducing various amine groups into compound (32) by reductive amination. Amino piperidine derivatives (35) can be prepared by acylation, amide coupling reaction, or akylation of compounds of formula (34), and deprotection.

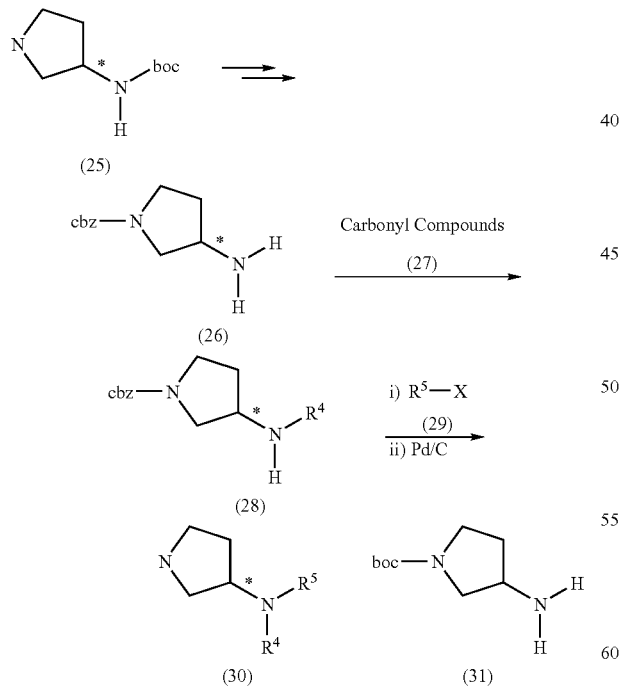

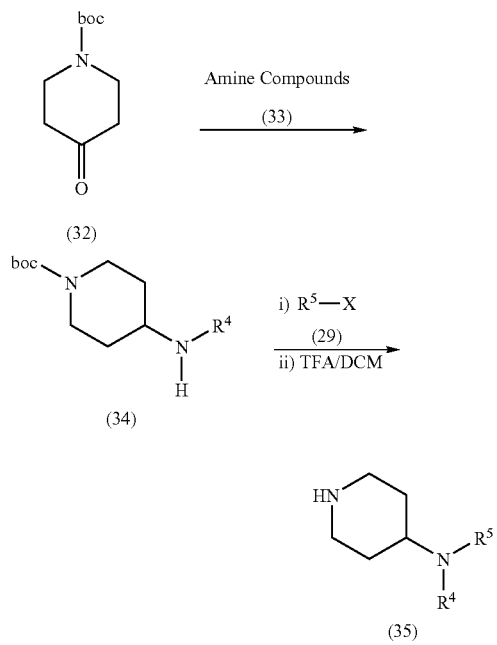

In the above reaction scheme, compound (29) represents alkylhalide, substituted alkylhalide, carboxylic acid, or acid chloride; and $R^6$ is the same as defined above; and X represents OH, Br, Cl, etc.

Azetidine derivatives can be prepared by the method illustrated in Scheme 8. Coupling of protected amino acid derivatives (1) with 3-azetidinol gives compounds of formula (37) which can then be converted into carbonyl compounds of formula (38). Compounds of formula (40) can be prepared from compounds of formula (38) via reductive amination, acylation, amide coupling, and alkylation.

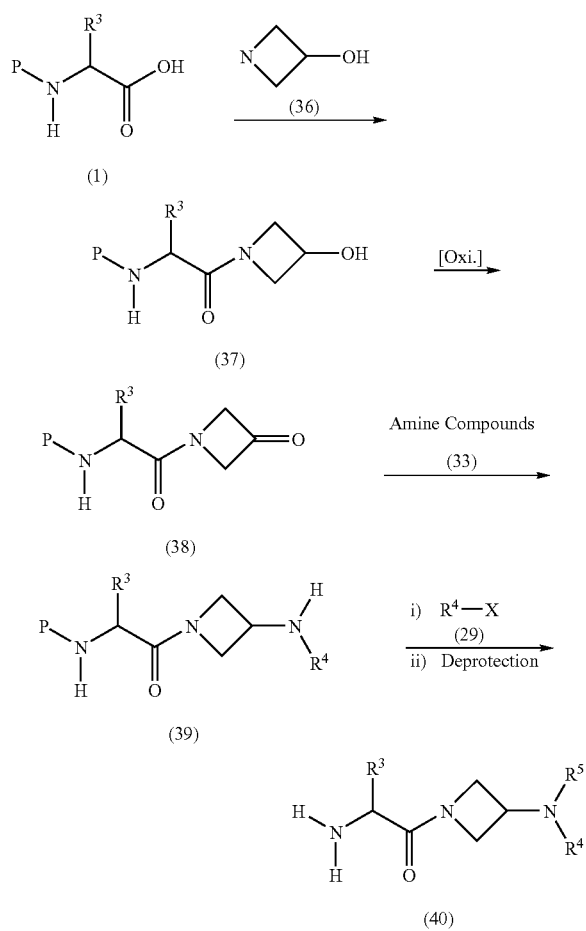

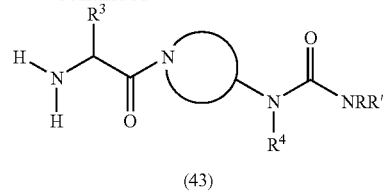

In the above reaction scheme, NRR' represents substituted or unsubstituted amino group among the definition of $R^7$, $R^8$, or $R^9$.

It is preferable to carry out each step of the above methods in conventional solvents which do not have significant deleterious effect to the reaction, and particularly preferable to use one or more kinds selected from the group consisting of, but not limited to, dimethylformamide, dimethylacetamide, tetrahydrofuran, methylene chloride, and chloroform.

Deprotection reaction can be carried out in the presence of strong acid such as hydrochloric acid, trifluoroacetic acid, etc., in the presence of amine base such as triethylamine, diisopropylethylamine, etc., or by hydrogenation. Specific reaction conditions are described in T. W. Green & G. M. Wuts Protective Groups in Organic Synthesis, Chapter 7, pp 309-405.

Known coupling agents usable in coupling reaction are, but are not limited to, carbodiimides such as dicyclohexylcarbodiimide (DCC), 1-(3-dimethylaminopropyl)-3-ethylcarbodiimide (EDC), 1,1'-dicarbonyldiimidazole (CDI), etc. which are used in a mixture with 1-hydroxybenzotriazole (HOBT) or 1-hydroxy-7-azabenzotriazole (HOAT); bis-(2-oxo-3-oxazolidinyl)-phosphinic acid chloride (BOP—Cl), diphenylphosphorylazide (DPPA), O-(7-Azabenzotriazol-1-yl)-N,N,N',N'-tetramethyluronium hexafluorophosphate (HATU), O-Benzotriazol-1-yl-N,N,N',N'-tetramethyluronium hexafluorophosphate (HBTU), etc.

General separation of mixtures is conducted by column chromatography, and in case of final compound, separation can be done by recrystallization or normal or reverse HPLC (Waters, Delta Pack, 300×50 mm I.D., C18 5 μm, 100 A). When recrystallization or HPLC is used for purification, the compound can be obtained in the form of trifluoroacetic acid salt. Hydrochloric acid salt can be obtained by using ion exchange resin.

After the above reactions according to the present invention are completed, products can be separated and purified by customary work-up methods, for example, chromatography, recrystallization, etc.

The compounds of the present invention have potent agonistic effect against melanocortin receptors, and so the present invention provides a melanocortin receptor agonistic composition comprising the compound of formula 1 as active ingredients together with pharmaceutically acceptable carrier. In particular, the composition according to the present invention has potent effect for the prevention and treatment of, but not limited to, diabetes, erectile dysfunction, obesity, and inflammation.

When the compounds according to the present invention are administered for clinical purpose, a preferable daily dose would be within the range of 0.01~10 mg/kg body weight as unitary dosage or separated dosage. However, a dosage level specific to individual patients can be varied, depending upon specific compound to be used, weight, sex, health condition, diet, administration time and method of drug, excretion rate, drug mixing, and severity of disease condition.

Urea derivatives can be prepared by the method illustrated in Scheme 9. Coupling of protected amino acid derivatives (1) with cyclic amine derivatives (41) produces compounds of formula (42). Compounds of formula (42) can be converted to urea derivatives (43) by phosgene-mediated amide coupling.

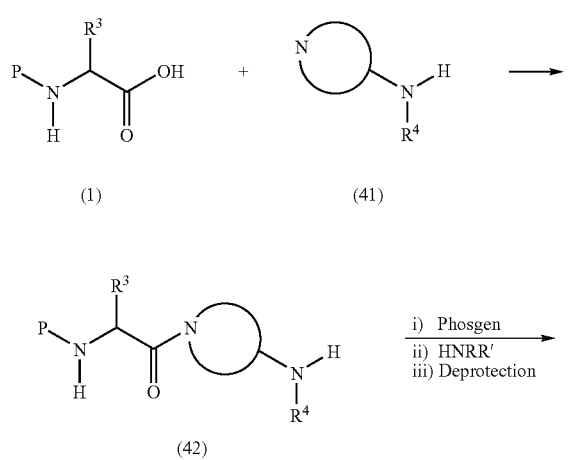

Any route depending on purpose can administer the compounds according to the present invention. Injection, and oral and nasal administration are preferred, but administration may be made through dermal, intraperitoneal, retroperitoneal, and rectal route.

Injectable preparation, for example, aqueous or oily suspension for sterile injection, can be prepared according to known method by using proper dispersants, wetting agents, or suspending agents. Solvents usable for this purpose are water, ringer's solution, and isotonic NaCl solution, and sterilized fixed oil is conventionally used as solvent or suspending media, too. Any non-irritable fixed oil including mono-, di-glyceride can be used for this purpose, and aliphatic acid such as oleic acid can be used for injectable preparation.

Solid dosage forms for oral administrations are capsules, tablets, pills, powders and granules, and in particular, capsules and tablets are useful. Capsules and tablets are preferable to be prepared as enteric coating. Solid dosage forms can be prepared by mixing compound (1) according to the present invention with one or more inert diluents such as sucrose, lactose, starch, etc., and carriers, for example, lubricants like magnesium stearate, disintegrants, binding agents, etc.

Abbreviations used in the above Description, and the following Preparations and Examples are as follows:
Ac acetyl
Bn benzyl
Bu butyl
CBZ(Cbz) benzyloxycarbonyl
BOC(Boc) tert-butoxycarbonyl
Fmoc 9-fluorenylmethoxycarbonyl
c-Hep cycloheptyl
c-Hex cyclohexyl
c-Pr: cyclopropyl
c-Pen cyclopentyl
DAST Diethylaminosulfur trifluoride
DCC dicyclohexylcarbodiimide
DCE dichloroethane
DCM dichloromethane
DEAD diethylazodicarboxylate
Dic decahydroisoquioline-3-carboxylic acid
DIPEA diisopropylethylamine
DMAP 4-dimethylaminopyridine
DMF N,N-dinethylformamide
DMSO Dimethylsulfoxide
DTic (D)-1,2,3,4-tetrahydriosoquinoline-3-carboxylic
EDC 1-(3-dimethylaminopropyl)-3-ethylcarbodiimide HCl
Gly Glycine
Hex hexane
HOBt 1-hydroxybenzotriazole
HBTU O-Benzotriazol-1-yl-N,N,N',N'-tetramethyluronium hexafluorophosphate
i-Bu isobutyl
i-Pr isopropyl
Mor Morpholine
MOM Methoxymethyl
Nos 2-Nitrobenzene sulfonyl
Ph phenyl
Phe phenylalanine
Pid piperidine
Pro proline
Pyd pyrrolidine
TEA triethylamine
TFA trifluoroacetic acid
TH:F Tetrahydrofuran
Tic 1,2,3,4-tetrahydroisoquinoline-3-carboxylic acid The following Intermediates further illustrate preparation of intermediates needed for synthesis of the compounds according to the present invention.

Intermediate 1: (3S)-1-Cbz-3-aminopyrrolidine

Step A: (3S)-1-Cbz-3-(N-BOC-amino)pyrrolidine

To a solution of (3S)-1-Cbz-3-(N-BOC-amino)pyrrolidine (5.00 g, 26.9 mmol) and TEA (7.54 mL, 53.8 mmol) in DCM (6 mL) was added CbzCl (5.50 g, 29.6 mmol) at rt. After 4 h, a saturated aqueous $NH_4Cl$ solution was added and the reaction mixture was extracted with DCM followed by EtOAc. The organic extracts were washed with brine, dried over magnesium sulfate, filtered, and concentrated in vacuo. The crude residue was purified by flash chromatography (EtOAc/Hex=1/2) to give the title compound (9.06 g, 96.1%).
MS [M+H]=321 (M+1)

Step B: (3S)-1-Cbz-3-amino-pyrrolidine

The product of Step A, (3S)-1-Cbz-3-(N-BOC-amino)pyrrolidine, (5.26 g, 16.4 mmol) was dissolved in EtOAc (50 mL) and treated with a saturated HCl in EtOAc (15 mL). After the reaction mixture was stirred at rt for 30 min., the volatiles were removed to provide the title compound (4.11 g, 98.1%) as a colorless solid. The crude product was used without further purification.
MS [M+1]=221 (M+1)

Intermediate 2:
(3S)-1-Cbz-3-(cyclohexylamino)pyrrolidine

To a solution of (3S)-1-Cbz-3-aminopyrrolidine (4.11 g, 16.0 mmol) and cyclohexanone (2.36 g, 24.0 mmol) in DCE (50 mL) was slowly added $NaBH(OAc)_3$ (6.78 g, 32.0 mmol) at rt. The reaction mixture was quenched after 4 h using a saturated aqueous $NaHCO_3$ solution and extracted with DCM followed by EtOAc. The combined organic extracts were washed with brine, dried over $MgSO_4$, filtered and concentrated in vacuo. The crude residue was purified by flash chromatography (EtOAc/Hex=2/1) to give the title compound (4.79 g, 98.1%).
MS [M+1]=303 (M+1)

Intermediate 3: 4,4-Dimethyl-cyclohexan-1-one 4,4-Dimethyl-cyclohexene-1-one (5 g, 52 mmol) and n-pentane (50 mL) were placed in a hydrogen reaction vessel and Pd/C (300 mg) was added. The hydrogen reaction vessel was purged three times with hydrogen and subsequently pressurized with hydrogen (25 psi). After shaking in a Parr hydrogenator for 30 min., the reaction mixture was filtered though Celite and the filtrate concentrated in vacuo to give the title compound.
MS[M+H]=127 (M+1)

Intermediate 4: 1-BOC-4-piperidone

To a solution of 4-piperidone (10 g, 100 mmol) and TEA (28.0 mL, 20 mmol) in DCM (2.00 l) was added di-t-butyl-dicarbonate (30 g, 150 mmol) at rt. After 4 h, the reaction mixture was concentrated in vacuo and the residue was diluted with 1N HCl (500 mL). The reaction mixture was extracted with EtOAc, dried over $MgSO_4$, filtered and concentrated in vacuo. The residue was purified by column chomatography (EtOAc/Hex=1/15) to give the title compound (19.1 g, 96.5%).

MS[M+H]=200 (M+1)

Intermediate 5: Spiro[2,5]octanone

Step A:
4,4-Methylene-1,1-ethyleneketal-4-spiro[2,5]octane

To a solution of DMSO (80 mL), filled with nitrogen, was added NaH (2.3 g, 58 mmol), and the reaction mixture was heated at 50-60° C. When the reaction solution turned light green, MeP (Ph)$_3$Br (21.2 g, 60 mmol) was added, and the reaction solution was cooled to rt and stirred for 1 h. Cyclohexanedione monoethyleneketal (5.64 g, 36 mmol) was slowly added, and then the reaction mixture was heated to 40° C. and stirred for additional 2 h. The reaction solution was cooled to rt and a solution of diethyl ether/ice-water was added. The organic solution extracted with Et$_2$O was dried over MgSO$_4$, filtered and concentrated in vacuo. The residue was purified by column chomatography (EtOAc/Hex=1/5) to give the title compound (4.51 g, 82%).

MS[M+H]=155 (M+1)

Step B: spiro[2,5]octanone

To a solution of 4,4-methylene-1,1-ethyleneketal-4-spiro [2,5]octane (4.5 g, 30 mmol), prepared by Step A, in Et$_2$O was added CH$_2$I$_2$ (12.0 mL, 150 mmol) and Zn—Cu (12.3 g, 48 mmol). The mixture was stirred at rt for 12 h, filtered, and diluted with 1N HCl solution. The organic material was extracted with diethyl ether, dried over MgSO$_4$ and then concentrated in vacuo to give the title compound. The crude product was used without further purification.

Intermediates 6~35

The compounds below were prepared following the procedure described in Intermediate 2 using commercially available amines, carbonyl compounds, amine compound prepared in Intermediate 1, and carbonyl compounds prepared in Intermediates 4, and 5.

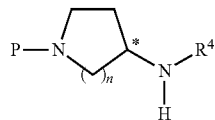

| Intermediate | P   | n | R$^4$ | * | MS (M + 1) |
|---|---|---|---|---|---|
| 6 | BOC | 1 | c-Hex | S | 303 |
| 7 | Cbz | 1 | c-Hex | R | 303 |
| 8 | Cbz | 1 | c-Pen | S | 289 |
| 9 | Cbz | 1 | c-Hep | S | 317 |
| 10 | Cbz | 1 | i-Pr | S | 263 |
| 11 | Cbz | 1 | (c-Hex)-CH$_2$— | S | 317 |
| 12 | Cbz | 1 | Ph | R,S | 297 |
| 13 | Cbz | 1 | 4-Me—Ph | R,S | 311 |
| 14 | Cbz | 1 | 3,5-diMe—Ph | R,S | 325 |
| 15 | Cbz | 1 | 2-Adamantyl | S | 355 |
| 16 | Cbz | 1 | 4-cis-Me-(c-Hex) | S | 317 |
| 17 | Cbz | 1 | 4-trans-Me-(c-Hex) | S | 317 |
| 18 | Cbz | 1 | 4,4-di-Me-(c-Hex) | S | 331 |
| 19 | Cbz | 1 | 4-t-Bu-(c-Hex) | S | 359 |
| 20 | Cbz | 1 | 4-cis-Et-(c-Hex) | S | 331 |
| 21 | Cbz | 1 | 4-trans-Et-(c-Hex) | S | 331 |
| 22 | Cbz | 1 | N—BOC-Pip-4-yl | S | 404 |
| 23 | Cbz | 1 | 4,4-ethyleneketal-(c-Hex) | S | 361 |
| 24 | Cbz | 1 | Spiro[2,5]octan-1-yl | S | 329 |
| 25 | Cbz | 1 | 4-Ph-c-Hex | S | 379 |
| 26 | BOC | 2 | c-Hex |  | 283 |
| 27 | BOC | 2 | c-Pen |  | 269 |
| 28 | BOC | 2 | c-Hep |  | 297 |
| 29 | BOC | 2 | i-Pr |  | 243 |
| 30 | BOC | 2 | (c-Hex)-CH$_2$— |  | 297 |
| 31 | BOC | 2 | i-Bu |  | 257 |
| 32 | BOC | 2 | 2-Me-c-Hex |  | 297 |
| 33 | BOC | 2 | 4,4-diMe-c-Hex |  | 311 |
| 34 | BOC | 2 | 4-trans-Me-c-Hex |  | 297 |
| 35 | BOC | 2 | 4-cis-Me-c-Hex |  | 297 |

Intermediate 36:
(3S)-3-[cyclohexyl(isobutyryl)amino]pyrrolidine

Step A: (3S)-1-Cbz-3-[cyclohexyl(isobutyryl)amino] pyrrolidine

To a solution of (3S)-1-Cbz-3-(cyclohexylamino)pyrolidine (4.75 g, 15.1 mmol) and TEA (4.26 mL, 30.2 mmol) in DCM (50 mL) was added dropwise isobutyryl chloride (1.15 mL, 60.3 mmol). The reaction mixture was stirred at rt for 12 h and quenched with 1N HCl solution. The organic material was extracted with DCM (50 mL×2) followed by EtOAc (50 mL×2), and the extracts were washed with a saline, dried over MgSO$_4$, and concentrated in vacuo. The residue was purified by column chomatography (EtOAc/Hex=1/3) to give the title compound (5.40 g, 96.7%).

MS[M+H]=372 (M+1)

Step B; (3)-3-[cyclohexyl(isobutyryl)amino]pyrrolidine

To a solution of (3S)-1-cbz-3-[cyclohexyl(isobutyryl) amino]pyrrolidine (5.00 g, 13.4 mmol), prepared in Step A, in Dioxane (40 mL) was added dropwise Pd/C (250 mg) at rt. After 12 h, the reaction mixture was filtered though Celite and the filtrate concentrated in vacuo to give the title compound as an oil (3.14 g, 98.5%).

MS[M+H]=239 (M+1)

Intermediates 37-61

The compounds below were prepared following the procedure described in Intermediate 36 or a step B of Intermediate 1 using acylchlorides or carbonyl compounds.

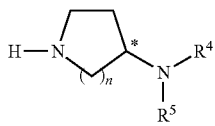

| Intermediates | * | n | R$^4$ | R$^5$ | MS (M + 1) |
|---|---|---|---|---|---|
| 37 | S | 1 | C(O)C(Me)$_3$ | c-Hex | 253 |
| 38 | S | 1 | C(O)Me | c-Hex | 227 |

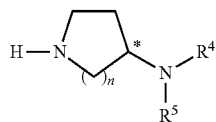

| Intermediates | * | n | R⁴ | R⁵ | MS (M + 1) |
|---|---|---|---|---|---|
| 39 | S | 1 | S(O)₂Me | c-Hex | 247 |
| 40 | S | 1 | C(O)N(Me)₂ | c-Hex | 240 |
| 41 | S | 1 | C(O)CH(Me)₂ | c-Pen | 225 |
| 42 | S | 1 | C(O)CH(Me)₂ | c-Hep | 253 |
| 43 | S | 1 | C(O)CH(Me)₂ | i-Pr | 199 |
| 44 | S | 1 | C(O)CH(Me)₂ | (c-Hex)-CH₂— | 253 |
| 45 | R | 1 | C(O)CH(Me)₂ | c-Hex | 238 |
| 46 | R | 1 | C(O)C(Me)₃ | c-Hex | 253 |
| 47 | R | 1 | C(O)N(Me)₂ | c-Hex | 240 |
| 48 | R | 1 | C(O)CH(Me)₂ | c-Pen | 225 |
| 49 |   | 2 | C(O)CH(Me)₂ | c-Hex | 253 |
| 50 |   | 2 | C(O)C(Me)₃ | c-Hex | 267 |
| 51 |   | 2 | C(O)OMe | c-Hex | 241 |
| 52 |   | 2 | S(O)₂Me | c-Hex | 261 |
| 53 |   | 2 | C(O)N(Me)₂ | c-Hex | 254 |
| 54 |   | 2 | Et | c-Hex | 210 |
| 55 |   | 2 | i-Bu | c-Hex | 238 |
| 56 |   | 2 | C(O)CH(Me)₂ | c-Pen | 239 |
| 57 |   | 2 | C(O)CH(Me)₂ | c-Hep | 267 |
| 58 |   | 2 | C(O)CH(Me)₂ | i-Pr | 212 |
| 59 |   | 2 | C(O)CH(Me)₂ | (c-Hex)-CH₂— | 267 |
| 60 |   | 2 | C(O)CH(Me)₂ | i-Bu | 226 |
| 61 |   | 2 | C(O)N(Me)₂ | 2-Me-c-Hex | 267 |

Intermediate 62: (3S)-1-benzyl-3-[(2,4-difluorophenyl)amino]pyrrolidine

To a solution of (3S)-1-benzyl-3-aminopyrrolidine (0.20 g, 1.1 mmol), tris-(2,4-difluorophenyl)bismuth (0.64 g, 1.2 mmol), and TEA (0.280 mL, 2 mmol) in DCM (5 mL) was added Cu(OAc)₂ (0.21 g, 1.2 mmol). After being stirred at rt for 24 h, the reaction solution was concentrated in vacuo, and the residue was purified by column chomatography (MeOH/CHCl₃=1/25) to give the title compound (150 mg, 46.0%).
MS[M+H]=289 (M+1)

Intermediate 63: (3S)-1-benzyl-3-[isobutyryl(2,4-difluorophenyl)amino]pyrrolidine To a solution of (3S)-1-benzyl-3-[(2,4-difluorophenyl)amino]pyrrolidine (150 mg, 0.52 mmol) and DMAP (6 mg, 0.05 mmol) in pyridine (7 mL) was added isobutyryl chloride (0.16 mL, 1.5 mmol) at 0° C. After being stirred at 60° C. for 18 h, the reaction mixture was quenched with an aqueous NaH(CO)₃ solution and extracted with EtOAc. The extracts were concentrated in vacuo, the reside was purified by column chomatography (MeOH/CHCl₃=1/25) to give the title compound (160 mg, 86.0%).
MS[M+H]=359 (M+1)

Intermediate 64: (3S)-3-[(isobutyryl(2,4-difluorophenyl)amino)pyrrolidine

To a solution of (3S)-1-benzyl-3-[isobutyryl(2,4-difluorophenyl)amino]pyrrolidine in 1N HCl and an aqueous EtOH solution was added Pd/C, and the reaction mixture was stirred at rt for 3 days under hydrogen. The reaction mixture was filtered though Celite, and the filtrate concentrated in vacuo. The crude product was recrystalized from EtOAc to give the title compound (99 mg, 73%) as a colorless prism.
MS[M+H]=269 (M+1)

Intermediate 65: (3S)-3-[(isobutyryl(2,5-difluorophenyl)amino)pyrrolidine

The title compound was prepared following the procedure described in Intermediates 63 and 64 using (3S)-1-benzyl-3-[(2,5-difluorophenyl)amino]pyrrolidine.
MS[M+H]=269 (M+1)

Intermediate 66: (3S)-3-[(isobutyryl(3,4-difluorophenyl)amino)pyrrolidine

The title compound was prepared following the procedure described in Intermediates 63 and 64 using (3S)-1-benzyl-3-[(3,4-difluorophenyl)amino]pyrrolidine.
MS[M+H]=269 (M+1)

Intermediate 67: 1-hydroxymethyl-1-cyclopentanecarboxylic acid

Cyclopentanecarboxylic acid (1.10 g, 10.0 mmol) was placed in a round-bottomed bottomed flask, filled with nitrogen, and 30 mL of THF (30 mL) was added. The solution was cooled to −78° C., and LDA (8.8 mL, 2.5 m in hexane) was added dropwise. After being stirred for 30 min., the solution was bubbled by nitrogen stream containing formaldehyde gas (formaldehyde gas was in situ generated by thermal degradation of anhydrouse paraformaldehyde at 160° C.). When the reaction solution turned light yellow, the reaction mixture was quenched with a saturated aqueous NH₄Cl solution at −78° C., and the organic material was extracted with EtOAc. The organic extracts were dried over MgSO₄, filtered, and concentrated in vacuo to give the title compound.
MS[M+H]=145 (M+1)

Intermediate 68: 2,2-dimethyl-3-methoxypropionic acid

Step A: 2,2-dimethyl-3-methoxypropionic acid ethyl ester

To a solution of 2,2-dimethyl-3-hydroxypropionic acid ethyl ester (1.3 g, 10.0 mmol) in CH₃CN (30 mL) was added Ag₂O (11.5 g, 50.0 mmol) and methyl iodide (0.56 mL, 11 mmol). The reaction mixture was stirred at rt for 12 h and quenched with a saturated aqueous NH₄Cl. The mixture was filtered though Celite, the filtrate concentrated in vacuo, and the residue was purified by column chromatography (EtOAc/Hex=1/10) to give the title compound (1.34 g, 91.2%).
MS[M+H]=147 (M+1)

Step B: 2,2-dimethyl-3-methoxypropionic acid

To a solution of 2,2-dimethyl-3-methoxypropionic acid ethyl ester (1.17 g, 8.00 mmol) in an aqueous MeOH solution (MeOH/H₂O=1/1, 24 mL) was added LiOH (560 mg, 16.0 mmol) at rt. After the rection mixture was stirred for 30 min., the solvent was removed in vacuo, and the residue was diluted with 1N HCl and EtOAc. The organic layer extracted with EtOAc, and the organic extracts were dried over MgSO₄, filtered, and concentrated in vacuo. The crude product was used without further purification.
MS[M+H]=133 (M+1)

Intermediate 69: 2,2-dimethyl-3-benzyloxypropionic acid

The title compound was prepared following the procedure described in Intermediate 68 using 2,2-dimethyl-3-hydroxypropionic acid ethyl ester and benzyl chloride.
MS[M+H]=209 (M+1)

Intermediate 70: 1-BOC-piperidine-4-carboxylic acid

To a solution of piperidine-4-carboxylic acid (1.29 g, 10.0 mmol) in water was added NaOH (800 mg, 20.0 mmol). When the reaction solution was clear, (BOC)$_2$O (2.5 g, 11.0 mmol) was added, and the reaction mixture was stirred at rt for 12 h. The solvent was removed in vacuo, and the residue was diluted with 1N HCl and EtOAc. The organic layer was extracted with EtOAc, and the organic extracts were dried over MgSO$_4$, filtered, and concentrated in vacuo. The product was used without further purification.
MS[M+]=230 (+1)

Intermediate 71: (2R)-2-methyl-3-acetyloxypropionic acid

To a solution of (2R)-2-methyl-3-hydroxypropionic acid (10.0 g, 100 mmol) in pyridine (30 mL) as added acetyl chloride(11.8 g, 15.0 mmol) at 0° C., and the reaction mixture was warmed to rt. After being stirried for 3 h, the reaction mixture was quenched with 1N HCl (30 mL), and the pH of the solution was adjusted to 3-4. The organic material was extracted with EtOAc, and the extracts were washed with 1N HCl at 4-5 times, dried over MgSO$_4$, filtered, and concentrated to give the title compound (11.4 g, 95.0%).
MS[M+H]=147 (M+1)

Intermediates 72-80

The compounds below were prepared following the procedure described in Intermediate 71 using various hydroxy carboxylic acid compounds.

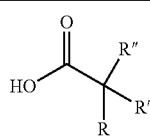

| Intermediate | R | R' | R'' | MS (M + 1) |
|---|---|---|---|---|
| 72 | Me | Me | OAc | 147 |
| 73 | Me | Me | CH$_2$OAc | 161 |
| 74 | Me | Me | (CH$_2$)$_2$OAc | 175 |
| 75 | Me | Me | (CH$_2$)$_3$OAc | 189 |
| 76 | Me | CH$_2$—OAc | CH$_2$OAc | 218 |
| 77 | —(CH$_2$)$_3$— | | CH$_2$OAc | 187 |
| 78 | —(CH$_2$)$_2$— | | CH$_2$OAc | 159 |
| 79 | 2-(AcOCH$_2$)-1-cyclopenten-1-yl | | | 185 |
| 80 | 2-(AcOCH$_2$)-1-cyclohexen-1-yl | | | 199 |

Intermediate 81: (3S)-3-[cyclohexyl(acetyloxypivaloyl)amino]pyrrolidine

Step A: 2,2-dimethyl-3-acetyloxypropionyl chloride

Intermediate 73, 2,2-dimethyl-3-acetyloxypropionic acid (11.76 g, 80 mmol) was dissolved in benzene (100 mL), and the reaction solution was cooled to 0° C. Oxalyl chloride (15.0 g, 120 mmol) was added dropwise. After being stirred for 3 h, the solvent was removed in vacuo, and the residue was distilled in vacuo to give the title compound.
MS[M+H]=179 (M+1)

Step B: (3S)-1-Cbz-3-[cyclohexyl(acetyloxypivaloyl)amino]pyrrolidine

To the mixture of (3S)-1-Cbz-3-(cyclohexylamino)pyrrolidine (3.0 g, 10 mmol), TEA (15 mL), and DMAP (1.25 g, 10 mmol) in THF (15 mL) was added 2,2-dimethyl-3-acetyloxypropionyl chloride (3.58 g, 20 mmol) prepared in Step A. After the reaction mixture was refluxed for 48 h (90-110° C.), the solvent was removed, and the residue was diluted with an aqueous NaHCO$_3$ solution was added to the residue. The organic material was extracted with EtOAc, and the extracts were washed by 1N HCl, dried over MgSO$_4$, and concentrated in vacuo. The crude product was purified by column chomatography (EtOAc/Hex=1/2) to give the title compound (2.80 g, 62.9%).
MS[M+H]=445 (M+1)

Step C: (3S)-3-[cyclohexyl(acetyloxypivaloyl)amino]pyrrolidine

To a solution of (3S)-1-Cbz-3-[cyclohexyl (acetyloxypivaloyl)amino]pyrrolidine (1.00 g, 2.25 mmol), prepared in Step B, in dioxane (10 mL) was added portionwise Pd/C (200 mg), and the mixture was stirred for 12 h under hydrogen. The reaction solution was filtered though Celite and the filtratae concentrated to give the title compound (657 mg, 84%).
MS[M+H]=311 (M+1)

Intermediates 82-125

The compounds below were prepared following the procedure described in Intermediate 81 or Step B of Intermediate 1 using commercially available carboxylic acid or carboxylic acid prepared in Intermediates 67-80, and amine compounds prepared in Intermediates 2, 6 and 6~35.

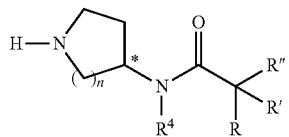

| Intermediate | n | * | R | R' | R" | R⁴ | MS (M + 1) |
|---|---|---|---|---|---|---|---|
| 82 | 1 | S | H | OH | i-Pr | c-Hex | 311 |
| 83 | 1 | S | H | H | C(Me)₂OH | c-Hex | 269 |
| 84 | 1 | S | H | Me | CH₂—OAc | c-Hex | 297 |
| 85 | 1 | S | Me | Me | OAc | c-Hex | 297 |
| 86 | 1 | S | Me | Me | (CH₂)₂—OAc | c-Hex | 325 |
| 87 | 1 | S | Me | Me | (CH₂)₃—OAc | c-Hex | 339 |
| 88 | 1 | S | Me | Me | CH₂—OAc | 4-cis-Me-c-Hex | 325 |
| 89 | 1 | S | Me | Me | CH₂—OAc | 4-trans-Me-(c-Hex) | 325 |
| 90 | 1 | S | Me | Me | CH₂—OAc | 4,4-di-Me-(c-Hex) | 339 |
| 91 | 1 | S | Me | Me | CH₂—OAc | 4-t-Bu-(c-Hex) | 367 |
| 92 | 1 | S | Me | Me | CH₂—OAc | 4-cis-Et-(c-Hex) | 339 |
| 93 | 1 | S | Me | Me | CH₂—OAc | 4-trans-Et-(c-Hex) | 339 |
| 94 | 1 | S | Me | Me | CH₂—OAc | Spiro[2.5]octan-1-yl | 337 |
| 95 | 1 | S | Me | Me | CH₂—OAc | 4-Ph-c-Hex | 387 |
| 96 | 1 | S | Me | Me | CH₂—OAc |  | 369 |
| 97 | 1 | S | Me | CH₂—OAc | CH₂—OAc | 4-cis-Me-(c-Hex) | 383 |
| 98 | 1 | S | Me | CH₂—OAc | CH₂—OAc | 4-trans-Me-(c-Hex) | 383 |
| 99 | 1 | S | Me | CH₂—OAc | CH₂—OAc | 4,4-di-Me-(c-Hex) | 397 |
| 100 | 1 | S | Me | CH₂—OAc | CH₂—OAc | c-Hex | 369 |
| 101 | 1 | S | Me | Me | CH₂—OMe | c-Hex | 283 |
| 102 |   | S | Me | Me | CH₂—OBn | c-Hex | 359 |
| 103 | 1 | S | Me | Me | (CH₂)₃—O-(2,4-diMe)Ph | c-Hex | 401 |
| 104 | 1 | S | —(CH₂)₄— | | CH₂—OAc | c-Hex | 337 |
| 105 | 1 | S | —(CH₂)₂— | | CH₂—OAc | c-Hex | 309 |
| 106 | 1 | S | —(CH₂)₂— | | CO₂Et | c-Hex | 309 |
| 107 | 1 | S | H | | 1-BOC-Pid-4-yl | c-Hex | 380 |
| 108 | 1 | S | H | | 1-(Nos)-Pid-4-yl | c-Hex | 465 |
| 109 | 1 | S |   |   | 3-OH—Ph | c-Hex | 289 |
| 110 | 1 | S |   |   | 2-(AcOCH₂)-1-cyclopenten-1-yl | c-Hex | 335 |
| 111 | 1 | S |   |   | 2-(AcOCH₂)-1-cyclohexen-1-yl | c-Hex | 349 |
| 112 | 1 | R | Me | Me | CH₂—OAc | c-Hex | 311 |
| 113 | 1 | R,S | Me | Me | CH₂—OAc | c-Hex | 311 |
| 114 | 1 | S | Me | Me | CH₂—OAc | 2,3-diF—Ph | 341 |
| 115 | 1 | R,S | Me | Me | CH₂—OAc | 2,3-diF—Ph | 341 |
| 116 | 1 | R,S | Me | Me | CH₂—OAc | 3,5-diMe-ph | 333 |
| 117 | 1 | R,S | Me | Me | CH₂—OAc | 4-Me—Ph | 319 |
| 118 | 1 | R,S | Me | Me | CH₂—OAc | Ph | 305 |
| 119 | 1 | S | Me | Me | CH₂—OAc | 2-Adamantyl | 363 |
| 120 | 2 | S | Me | CH₂—OAc | CH₂—OAc | 4-cis-Me-(c-Hex) | 397 |
| 121 | 2 | S | Me | CH₂—OAc | CH₂—OAc | 4-trans-Me-(c-Hex) | 397 |
| 122 | 2 | S | Me | CH₂—OAc | CH₂—OAc | 4,4-di-Me-(c-Hex) | 411 |
| 123 | 2 | S | Me | Me | CH₂—OAc | c-Hex | 325 |
| 124 | 2 | S |   |   | 2-(AcOCH₂)-1-cyclopenten-1-yl | c-Hex | 349 |
| 125 | 2 | S |   |   | 2-(AcOCH₂)-1-cyclohexen-1-yl | c-Hex | 363 |

Intermediate 126: (3S)-3-[acetyloxypivaloyl(4,4-diF-cyclohexyl)amino]pyrrolidine Step A: (3S)-1-cbz-3-[acetyloxypivaloyl(4-oxo-cyclohexyl)amino]pyrrolidine Intermediate 96, (3S)-1-cbz-3-[acetyloxypivaloyl(4,4-ethyleneketal-cyclohexyl)amino]pyrrolidine (1.86 g, 5.16 mmol) was dissolved in THF (5 mL), and 3N HCl (5 mL) was added. The reaction solution was stirred at 50° C. for 12 h and neutralized by addition of a saturated aqueous 1N NaOH solution. The organic material was extracted with EtOAc and the extracts were dried over MgSO₄, concentrated in vacuo, and purified by column chomatography (EtOAc/Hex=1/1) to give the title compound (1.40 g, 85.7%).

MS[M+H]=459 (M+1)

Step B: (3)-1-cbz-3-[acetyloxypivaloyl(4,4-difluoro-cyclohexyl)amino]pyrrolidine The product of Step A, (3S)-1-cbz-3-[acetyloxypivaloyl(4-oxo-cyclohexyl)amino]pyrrolidine (1.40 g, 4.42 mmol) was dissolved in DCM (15 mL), and DAST (1.42 g, 8.84 mmol) was added at −78° C., and the reaction mixture was warmed to rt. After being stirred for 24 h, the reaction mixture was quenched with a saturated aquenous NaHCO₃ solution w and extracted with DCM. The extracts were dried over MgSO₄ and concentrated in vacuo, and the residue purified by column chomatography (EtOAc/Hex=2/1) to give the title compound (500 mg, 33.5%).

MS[M+H]=481 (N+1)

Step C: 3-[acetyloxypivaloyl(4,4-diF-cyclohexyl)amino]pyrrolidine

The title compound was prepared following the procedure described in Intermediate 64 using the product of Step B, (3S)-1-cbz-3-[acetyloxypivaloyl (4,4-diF-cyclohexyl)amino]pyrrolidine.
MS[M+1]=347 (M+1)

Intermediate 127: (3S)-3-[acetyloxypivaloyl(4-F-cyclohexyl)amino]pyrrolidine

Step A: (3S)-1-cbz-3-[acetyloxypivaloyl(4-hydroxy-cyclohexyl)amino]pyrrolidine

The product of Step A of Intermediate 126, (3S)-1-cbz-3-[acetyloxypivaloyl (4-oxo-cyclohexyl)amino]pyrrolidine (1.60 g, 3.49 mmol) was dissolved in THF (15 mL), and NaBH$_4$ (172 mg, 4.19 mmol) was added at rt. After being stirred for 12 h, the reaction mixture was quenched with water, and the organic material was extracted with EtOAc. The extracts were dried over MgSO$_4$ and concentrated in vacuo, and the residue was purified by column chomatography (EtOAc/Hex=1/1) to give the title compound (1.481 mg, 92.1%).
MS[M+H]=461 (M+1)

Step B: (3S)-1-cbz-3-[acetyloxypivaloyl(4-fluorocyclohexyl)amino]pyrrolidine

The title compound was prepared following the procedure described in Step B of Intermediate 126 using the product of Step A, (3S)-1-cbz-3-[acetyloxypivaloyl(4-hydroxy-cyclohexyl)amino]pyrrolidine.
MS[M+H]=463 (+1)

Step C: (3S)-3-[acetyloxypivaloyl(4-fluorocyclohexyl)amino]pyrrolidine

The title compound was prepared following the procedure described in Intermediate 64 using the product of Step B, (3S)-1-cbz-3-[acetyloxypivaloyl(4-fluoro-cyclohexyl)amino]pyrrolidine.
MS[M+1]=329 (M+1)

Intermediate 128: methyl 2-[(3S)-3-pyrrolidinyl(cyclohexyl)amino]acetate

Step A: methyl 2-[(3S)-1-Cbz-3-pyrolidinyl(cyclohexyl)amino]acetate

NaH (60% in mineral oil, 52.0 mg, 1.30 mmol) was placed in a round-bottom flask, filled with nitrogen, and then THF (10 mL) was added. A solution of (3S)-1-Cbz-3-(cyclohexylamino)pyrrolidine (302 mg, 1.00 mmol) prepared in Intermediate 2 in THF was added dropwise at 0° C., and the reaction mixture was stirred for 30 min until no further gas evolution occurred, followed by slow addition of methyl bromoacetate. After 4 h, the reaction, mixture was quenched with water and extracted with EtOAc. The extracts were dried over MgSO$_4$ and concentrated in vacuo, and the residue was purified by column chomatography (EtOAc/Hex=1/2) to give the title compound (227 mg, 90.0%).
MS[M+H]=375 (M+1)

Step B: methyl 2-[(3S)-3-pyrrolidinyl(cyclohexyl)amino]acetate

The title compound was prepared following the procedure described in Step B of Intermediate 3 using the product of Step A, methyl 2-[(3S)-1-Cbz-pyrrolidin-3-yl (cyclohexyl)amino]acetate.
MS[M+H]=241 (M+1)

Intermediate 129: (3S)-3-{cyclohexyl[(N-BOC)aminoacetyl]amino}pyrrolidine

Step A: A: (3S)-1-Cbz-3-{cyclohexyl[(N-BOC)aminoacetyl]amino}pyrrolidine

To a solution of (3S)-1-Cbz-3-{cyclohexylamino}pyrrolidine (3.0 g, 10.0 mmol), prepared in Intermediate 2, in DMF (30 mL) were added DIPEA (3.50 mL, 20.0 mmol), HBTU (4.88 g, 13 mmol), BOC-Gly (1.92 g, 11 mmol). After the mixture was stirred at rt for 4 h, the solvent was removed in vacuo, and the residue was diluted with an aqueous NaHCO$_3$. The organic material was extracted with EtOAc, and the organic extracts were washed with 1N HCl, dried over MgSO$_4$, concentrated in vacuo. The residue was purified by column chomatography (EtOAc/Hex=1/3) to give the title compound (4.63 g, 92.0%).
MS[M+H]=474 (M+1)

Step B: (3S)-3-{cyclohexyl[(N-BOC)aminoacetyl]amino}pyrrolidine

The title compound was prepared following the procedure described in Step B of Intermediate 3 using the product of Step A, (3S)-1-Cbz-3-{cyclohexyl[(N-BOC)aminoacetyl]amino}pyrrolidine.
MS[M+H]=340 (M+1)

Intermediates 130~134

The compounds below were prepared following the procedure described in Intermediate 36 or 129 using commercially available carboxylic acid and amine compounds prepared in Intermediates 6~35.

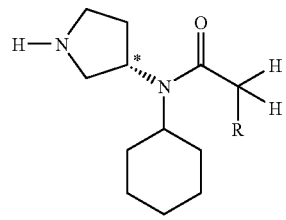

| Intermediate | R | MS (M + 1) |
| --- | --- | --- |
| 130 | CH$_2$NH(BOC) | 354 |
| 131 | CH$_2$CH$_2$NH(BOC) | 368 |
| 132 | CH$_2$C(O)OMe | 297 |
| 133 | CH$_2$OH | 255 |
| 134 | (CH$_2$)$_2$—OC(O)—CF$_3$ | 365 |

Intermediate 135: (2R)-N-methanesulfonyl-(4-chlorophenyl)alanine

Step A: (2R)-N-methanesulfonyl-(4-chlorophenyl)alanine methyl ester

To a solution of (2R)-4-chlorophenylalanine methylester (213 mg, 1.00 mmol) in DCM (5 mL) was added dropwise TEA (280 µl, 2.00 mmol) and then methanesulfonylchloride (100 µl, 1.3 mmol) at 0° C. After 30 min, the reaction mixture was quenched with water and extracted with DCM and EtOAc. The organic solution was washed with 1N HCl, dried over MgSO₄ and concentrated in vacuo, and the residue was purified by column chomatography (MeOH/CHCl₃=1/25) to give the title compound (280 mg, 96.1%).
MS[M+H]=292 (M+1)

Step B: (2R)-N-methanesulfonyl-(4-chlorophenyl)alanine

To a solution of (2R)-N-methanesulfonyl-(4-chlorophenyl)alanine methylester, prepared in Step A, in water/methanol (5 mL, 1/1) was added portionwise LiOH (70.0 mg, 2.00 mmol). After being stirred at rt for 3 h, the reaction mixture was concentrated, and the residue was diluted with 1N HCl solution. The organic material was extracted with EtOAc, the extracts were concentrated in vacuo to give the title compound (179 mg, 94.3%).
MS[M+H]=277 (M+1)

Intermediate 136: (2R)-N-acetyl-(4-chlorobenzyl)alanine

The title compound was prepared following the procedure described in Intermediate 135 using anhydrous (2R)-4-chlorophenylalanine methylester.
MS[M+H]=278 (M+1)

Intermediate 137: (2R)-N-[(N,N-dimethyl)carbamoyl]-(4-chlorobenzyl)alanine

The title compound was prepared following the procedure described in Intermediate 135 using (2R)-4-chlorophenylalanine methylester and chlorodimethyl carbamate.
MS[M+H]=278 (M+1)

Intermediate 138: (2R)-N-BOC-prolinal

Step A: (2R)-N-BOC-proline ethylthioester

To a solution of DCC (2.55 g, 12.4 mmol), DMAP (100 mg), and EtSH (0.71 g, 11.1 mmol) in DCM was added dropwise a solution of (2R)-N-BOC-proline (3.00 g, 9.52 mmol) in DCM (30 mL). The reaction mixture was stirred at rt for 30 min, and filtered though Celite. The filtrate was dried over MgSO₄ and concentrated in vacuo, and the residue was purified by column chomatography (EtOAc/Hex=1/4) to give the title compound (2.34 g, 95.2%).
MS[M+H]=260 (M+1)

Step B: (2R)-N-BOC-prolinal

To a solution of (2R)-N-BOC-proline ethylthioester, prepared in Step A, in acetone were added dropwise triethylsilane (5.39 g, 46.3 mmol) and Pd/C (100 mg) at 0° C. When no further gas evolution occurred, the reaction mixture was warmed to rt and then stirred for additional 30 min. The reaction solution was filtered though Celite, the filtrate concentrated in vacuo. The residue was purified by column chomatography (EtOAc/Hex=1/2) to give the title compound (1.43 g, 93.2%).
MS[M+H]=200 (M+1)

Intermediate 138: (2R)-N-methylprolinal

Step A: (2R)-N-methylproline methyl ester (2R)-proline methylester (1.20 g, 10.0 mmol) was dissolve in DMF (30 mL), and formalin (37% in water, 1.12 mL, 15.0 mmol) and NaBH (OAc)₃ (4.20 g, 20.0 mmol) were added portionwise. After 12 h, the reaction material was concentrated in vacuo, and the residue was diluted with NaHCO₃ (30 mL). The organic material was extracted with EtOAc, and the organic extracts were dried over MgSO₄ and concentrated in vacuo. The residue was purified by column chomatography (EtOAc/Hex=4/1) to give the title compound (1.33 g, 93.0%).
MS[M+H]=144 (M+1)

Step B: (2R)-N-methylprolinal

The title compound was prepared following the procedure described in Step of Intermediate 135 using methyl (2R)-N-methyl-proline methylester prepared in Step A.
MS[M+H]=114 (M+1)

Intermediates 140~148

The compounds below were prepared following the procedure described in Intermediates 138 and 139 using various amino acid derivatives.

| Intermediate | X | n | * | MS (M + 1) |
|---|---|---|---|---|
| 140 | Me | 1 | S | 114 |
| 141 | Ac | 1 | R | 142 |
| 142 | S(O)₂Me | 1 | R | 178 |
| 143 | C(O)N(Me)₂ | 1 | R | 171 |
| 144 | n-Bu | 1 | R | 156 |
| 145 | Me | 2 | S | 128 |
| 146 | Me | 2 | R | 128 |
| 147 | Ac | 2 | R | 156 |
| 148 | S(O)₂Me | 2 | R | 192 |

Intermediate 149: 1-BOC-2-aziridinecarboxylic acid

Step A: Methyl 1-benzyl-2-aziridinecarboxylate

To a solution of methyl 2,3-dibromopropionate (92.50 g, 10.0 mmol) and K₂CO₃ (4.10 g 30.0 mmol) in acetonitrile (30 mL) was added dropwise benzylamine (1.20 mL, 11 mmol). After being stirred at rt for 4 h, and the reaction mixture was quenched with a saturated aqueous NH₄Cl solution. The organic material was extracted with EtOAc, the extracts dried over MgSO₄, concentrated in vacuo. The residue was purified by column chomatography (EtOAc/Hex 2/1) to give the title compound (1.62 g, 85%).
MS[M+H]=192 (M+1)

Step b: Methyl 1-BOC-2-aziridine carboxylate

To a solution of methyl 1-benzyl-2-aziridinecarboxylate (1.00 g, 5.23 mmol) and di-t-butyl-dicarbonate (1.34 g, 5.75 mmol), prepared in Step A, in methanol (20 mL) was added portionwise Pd/C (300 mg). The mixture was stirred at rt under hydrogen for 24 h and filtered though Celite. The filtrate was concentrated in vacuo, and the residue was purified by column chomatography (EtOAc/Hex=2/1) to give the title compound (985 mg, 91.0%).
MS[M+H]=202 (+1)

Step C: 1-BOC-aziridine-2-carboxylic acid

The title compound was prepared following the procedure described in Step B of Intermediate 135 using methyl 1-BOC-2-aziridinecarboxylate prepared in Step B.
MS[+H]=188 (M+1)

Intermediate 150: 1-BOC-aziridine-2-carboxaldehyde

The title compound was prepared following the procedure described in Intermediate 138 using 1-BOC-aziridine-2-carboxylic acid.
MS[M+H]=172(M+1)

Intermediate 151: 2-ethylamino-1-acetyloxyethane

Step A: 2-(BOC)amino-1-acetyloxyethane

To a solution of 2-(BOC)aminoethanol (3.2 g, 20.0 mmol) in DCM (60 mL) were added TEA (5.6 mL, 40.0 mL) and acetyl chloride (3.36 mL, 30 mmol) at 0° C. After the reaction solution was stirred for 2 h, the solvent was removed, and the residue dissolved in water. The organic material was extracted with EtOAc, and the extracts were washed with 1N HCl, dried over $MgSO_4$, concentrated in vacuo. The residue was purified by column chomatography (eluent: EtOAc/Hex=1/10) to give the title compound (3.2 g, 80%).
MS[M+H]=204(M+1)

Step B: 2-amino-1-acetyloxyethane 2-(BOC)amino-1-acetyloxyethane (3.00 g, 15.0 mmol), prepared in Step A, was dissolved in DCM (15.0 mL), and TFA (15.0 mL) was added. After being stirred 30 min, the reaction mixture was concentrated in vacuo to give the title compound. The product was used without further purification.
MS[M+H]=104(M+1)

Step C: 2-[(2-nitrobenzene)sulfonyl]amino-1-acetyloxyethane

To a solution of 2-amino-1-acetyloxyethane (1.00 g, 10.0 mmol), prepared in Step B (1.00 g, 10.0 mmol) and $Et_3N$ (2.80 mL, 20 mmol) in DCM (30 mL) was added dropwise (2-nitrobenzene)sulfonyl chloride (2.43 g, 22 mmol). After being stirred at rt for 4 h, the reaction mixture was quenched with water and extracted with EtOAc. The extracts were washed with 1N HCl, dried over $MgSO_4$, concentrated in vacuo. The residue was purified by column chomatography (eluent: EtOAc/Hex=1/3) to give the title compound (2.72 g, 94.0%).
MS[M+1]=289(M+1)

Step D: 2-{ethyl[(2-nitrobenzene)sulfonyl]}amino-1-acetyloxyethane

To a solution of 2-[(2-nitrobenzene)sulfonyl]amino-1-acetyloxyethane prepared in Step C (1.45 g, 5.00 mmol) and $P(Ph)_3$ (1.3 g, 5 mmol) in THF (15 mL) were added ethanol (0.40 mL, 15 mmol) and DEAD (0.32 mL, 10.0 mmol). After being stirred for 12 h, the solvent was removed and the residue was purified by column chromatography (eluent: EtOAc/Hex=1/5) to give the title compound (1.40 g, 80%).
MS[M+1]=317(M+1)

Step E: 2-ethylamino-1-acetyloxyethane

To a solution of 2-{ethyl[(2-nitrobenzene)sulfonyl]}amino-1-acetyloxyethane (634 mg, 2.00 mmol) prepared in Step D in DMF (10 mL) were added $K_2CO_3$ (540 mg, 4 mmol) and mercaptobenzene (330 mg, 1.5 mmol). The reaction mixture was stirred at rt for 1 h, concentrated in vacuo, and diluted with water. The organic material was extracted with EtOAc, and the extracts were washed with 1N HCl, dried over $MgSO_4$, concentrated in vacuo. The residue was purified by column chomatography (eluent: EtOAc/Hex=1/3) to give the title compound.
MS[M+H]=132(M+1)

Intermediate 152-157

The compounds below were prepared following the procedure described in Intermediates 151 using commercially available aminoalcohol or (N-BOC)aminoethanol.

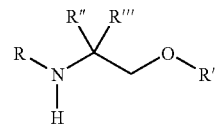

| Intermediate | R | R' | R" | R'" | MS (M + 1) |
|---|---|---|---|---|---|
| 152 | Pr | Ac | H | H | 146 |
| 153 | Et | Me | H | H | 104 |
| 154 | c-Pr | Ac | H | H | 144 |
| 155 | $CH_2CH_2OMe$ | Ac | H | H | 162 |
| 156 | Me | Ac | Me | Me | 146 |
| 157 | $CH_2CH_2OMe$ | Me | H | H | 134 |

Intermediate 158: (2R)-2-(BOC)amino-N-{4-[cyclohexyl(hydroxyethylcarbamoyl)amino]piperidine-1-yl}-3-(4-chlorophenyl)propionamide

Step A; 4-[cyclohexyl)amino]piperidine

The title compound was prepared following the procedure described in Step A of Intermediate 1 using 1-BOC-4-[(cyclohexyl)amino]piperidine prepared in Intermediate 26.
MS[M+H]=183(M+1)

Step B; (2R)-2-(BOC)amino-N-[4-(cyclohexylamino)piperidine-1-yl]-3-(4-chlorophenyl)propionamide The title compound was prepared following the procedure described in Intermediate 129 using (2R)-2-(BOC)amino-3-(4-chlorophenyl)propionic acid and 4-[(cyclohexyl)amino]piperidine.
MS[M+H]=464(M+1)

Step C: N-cyclohexyl[(2R)-2-(BOC)amino-3-(4-chlorophenyl)-1-oxo]piperidine-4-yl}carbamoyl chloride To a solution of (2R)-2-(BOC)amino-N-[4-(cyclohexylamino)poperidine-1-yl]-3-(4-chlorophenyl)propionamide prepared in Step B (4.63 g, 10 mmol) in DCM (30 mL) was added phosgene (25% in toluene, 12.6 mL, 30 mmol). After the reaction solution was stirred at rt for 4 h, the solvent was removed, and the residue was purified by column chomatography (eluent: EtOAc/Hex=1/3) to give the title compound (4.58 g, 87%).

MS[M+H]=526(M+1)

Step D: (2R)-2-(BOC)amino-N-{(4-[cyclohexyl(hydroxyethylcarbamoyl)amino]piperidine-1-yl)-3-(4-chlorophenyl)propionamide The title compound was prepared following the procedure described in Step B of Intermediate 81 using N-cyclohexyl[(2R)-2-(BOC)amino-3-(4-chlorophenyl)-1-oxo]piperidine-4-yl}carbamoyl chloride.

MS[M+H]=551(M+1)

Intermediate 59-190

The compounds below were prepared following the procedure described in Intermediates 158 using commercially available aminoalcohols or amine compounds prepared in Intermediate 6-35.

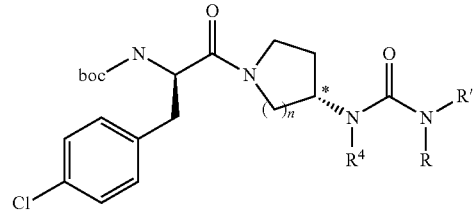

| Intermediate | R | R' | R⁴ | n | * | MS (M+1) |
|---|---|---|---|---|---|---|
| 159 | H | CH$_2$(CH$_2$)$_3$NH(BOC) | c-Hex | 1 | S | 664 |
| 160 | H | CH$_2$(CH$_2$)$_2$NH(BOC) | c-Hex | 1 | S | 650 |
| 161 | H | CH$_2$CH$_2$NH(BOC) | c-Hex | 1 | S | 636 |
| 162 | H | CH$_2$CH$_2$OH | c-Hex | 1 | S | 537 |
| 163 | CH$_2$CH$_2$OH | CH$_2$CH$_2$OH | c-Hex | 1 | S | 581 |
| 164 | H | CH$_2$CH$_2$OMe | c-Hex | 1 | S | 551 |
| 165 | 3(S)-hydroxy-Pyd-1-yl | | c-Hex | 1 | S | 563 |
| 166 | 2(S)-hydroxymethyl-Pyd-1-yl | | c-Hex | 1 | S | 577 |
| 167 | Me | CH$_2$CH$_2$OH | c-Hex | 2 | | 565 |
| 168 | Et | CH$_2$CH$_2$OH | c-Hex | 2 | | 579 |
| 169 | Pr | CH$_2$CH$_2$OH | c-Hex | 2 | | 593 |
| 170 | c-Pr | CH$_2$CH$_2$OH | c-Hex | 2 | | 591 |
| 171 | CH$_2$CH$_2$OMe | CH$_2$CH$_2$OH | c-Hex | 2 | | 609 |
| 172 | Me | CH$_2$CH$_2$OMe | c-Hex | 2 | | 579 |
| 173 | Et | CH$_2$CH$_2$OMe | c-Hex | 2 | | 593 |
| 174 | CH$_2$CH$_2$OMe | CH$_2$CH$_2$OMe | c-Hex | 2 | | 623 |
| 175 | Me | Et | c-Hex | 2 | | 563 |
| 176 | Me | OMe | c-Hex | 2 | | 551 |
| 177 | Me | C(Me)$_2$CH$_2$OH | c-Hex | 2 | | 593 |
| 178 | Me | CH$_2$CH$_2$OH | 2,3-diF—Ph | 2 | | 593 |
| 179 | Me | CH$_2$CH$_2$OMe | 2,3-diF—Ph | 2 | | 609 |
| 180 | CH$_2$CH$_2$F | CH$_2$CH$_2$OMe | c-Hex | 2 | | 611 |
| 181 | 3(R)-hydroxy-Pyd-1-yl | | c-Hex | 2 | | 577 |
| 182 | 3(S)-hydroxy-Pyd-1-yl | | c-Hex | 2 | | 577 |
| 183 | (2R)-hydroxymethyl-Pyd-1-yl | | c-Hex | 2 | | 591 |
| 184 | (2S)-hydroxymethyl-Pyd-1-yl | | c-Hex | 2 | | 591 |
| 185 | (3S)-N-BOC-amino-Pyd-1-yl | | c-Hex | 2 | | 576 |
| 186 | (3R)-N-BOC-amino-Pyd-1-yl | | c-Hex | 2 | | 576 |
| 187 | (3R)-hydroxy-Pid-1-yl | | c-Hex | 2 | | 591 |
| 188 | (3S)-hydroxy-Pid-1-yl | | c-Hex | 2 | | 591 |
| 189 | 4-hydroxy-Pid-1-yl | | c-Hex | 2 | | 591 |
| 190 | 4-N-BOC-amino-Pid-1-yl | | c-Hex | 2 | | 590 |

Intermediate 191: 4-[cyclohexyl(isopropylcarbamoyl)amino]piperidine

Step A: 1-BOC-4-[cyclohexyl(isopropylcarbamoyl)amino]piperidine

To a solution of 1-BOC-4-cyclohexylamino)piperidine (282 mg, 1.00 mmol) in DCM (3 mL) was added isopropyl isocyanate (108 μl, 1.10 mmol). After being stirred at rt for 30 min, the reaction solution was concentrated in vacuo, and the residue was purified by column chomatography (eluent: EtOAc/Hex=1/5) to give the title compound (354 mg, 94.0%).
MS[M+H]=368(M+1)

Step B: 4-[cyclohexyl(N-isopropylcarbamoyl)amino]piperidine

The title compound was prepared following the procedure described in Step B of Intermediate 1 using 1-BOC-4-[cyclohexyl(N-isopropylcarbamoyl)amino]piperidine.
MS[M+H]=268(M+1)

Intermediate 192: 4-{cyclohexyl[methyl(isopropyl)carbamoyl]amino}piperidine

Step A: 1-BOC-4-{cyclohexyl[methyl(isopropyl)carbamoyl]amino}piperidine

The title compound was prepared following the procedure described in Step A of Intermediate 128 using 1-BOC-4-[cyclohexyl(isopropylcarbamoyl)amino]piperidine.
MS[M+H]=382(M+1)

Step B: 4-{cyclohexyl[methyl(isopropyl)carbamoyl]amino}piperidine

The title compound was prepared following the procedure described in Step B of Intermediate 1 using 1-BOC-4-{cyclohexyl[methyl(isopropyl)carbamoyl]amino}piperidine.
MS[M+H]=282(M+1)

Intermediate 193-198

The compounds below were prepared following the procedure described in Intermediates 128 or Step A of Intermediate 191 using 1-BOC-4-(cyclohexylamino)piperidine and isocyanates or isothiocyanates.

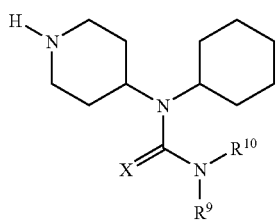

| Intermediate | X | $R^9$ | $R^{10}$ | MS (M + 1) |
|---|---|---|---|---|
| 193 | O | H | n-Bu | 281 |
| 194 | O | H | c-Hex | 307 |
| 195 | O | H | Ph | 301 |
| 196 | O | Me | n-Bu | 295 |
| 197 | S | H | Et | 275 |
| 198 | S | Me | Et | 289 |

Intermediate 199: methyl[cyclohexyl(piperidin-4-yl)amino]acetate

Step A; methyl{cyclohexyl[1-(BOC)piperidin-4-yl]amino}acetate

The title compound was prepared following the procedure described in Step A of Intermediate 128 using 1-BOC-4-(cyclohexylamino)poperidine.
MS[M+H]=355(M+1)

Step B: methyl[cyclohexyl(piperidin-4-yl)amino]acetate

The title compound was prepared following the procedure described in Step B of Intermediate 1 using methyl{cyclohexyl[1-(BOC)piperidin-4-yl]amino}acetate prepared in Step A.
MS[M+H]=255(M+1)

Intermediate 200: (2R)-2-(BOC)amino-N-(3-hydroxyazetidine-1-yl)-3-(4-chlorophenyl)propionamide The title compound was prepared following the procedure described in Step A of Intermediate 129 using (2R)-1-BOC-(4-chlorophenyl)alanine and 3-hydroxyazetidine (*Syn. Lett.*, 1991, 783.).
MS[M+H]=355(M+1)

Intermediate 201: (2R)-2-(BOC)amino-N-(3-oxo-azetidine-1-yl)-3-(4-chlorophenyl)propionamide (2R)-2-(BOC)Amino-N-(3-hydroxyazetidine-1-yl)-3-(4-chlorophenyl)propionamide (3.54 g, 10 mmol) was placed in a round-bottomed flask, filled with nitrogen, and DCM (30 mL) and oxalyl chloride (872 μl, 10 mmol) were added. The mixture was cooled to −78-C, and DMSO (709 μl, 10 mmol) was added. The reaction solution was stirred for 3 h keeping the temperature below −50° C. The reaction mixture was quenched by addition of TEA and warmed to rt. The reaction solution was diluted with a saturated aqueous $NH_4Cl$ solution, and the organic material was extracted with EtOAc. The extracts was dried over $MgSO_4$ and concentrated in vacuo, and the residue was purified by column chomatography (eluent: EtOAc/Hex=1/3) to give the title compound (2.88 g, 84%).
MS[M+H]=353(M+1)

Intermediate 202: (2R)-2-(BOC)amino-N-[3-(cyclohexylamino)azetidine-1-yl]-3-(4-chlorophenyl)propionamide The title compound was prepared following the procedure described in Intermediate 2 using (2R)-2-(BOC-amino)-N-(3-oxo-azetidine-1-yl)-3-(4-chlorophenyl)propionamide prepared in Intermediate 201 and cyclohexylamines.
MS[M+H]=437(M+1)

Intermediate 203: (2R)-2-(BOC)amino-N-{3-[cyclohexyl(isobutyryl)amino]azetidine-1-yl}-3-(4-chlorophenyl)propionamide The title compound was prepared following the procedure described in Step A of Intermediate 36 using (2R)-2-(BOC)amino-N-[3-(cyclohexylamino)azetidine-1-yl]-3-(4-chlorophenyl)propionamide prepared in Intermediate 202 and isobutyrylchloride.
MS[M+H]=507(M+1)

Intermediate 204-217

The compounds below were prepared following the procedure described in Intermediates 201 and 203 using (2R)-2-(BOC)amino-N-(3-hydroxyazetidine-1-yl)-3-(4-chlorophenyl)propionamide prepared in Intermediate 200.

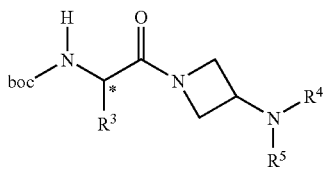

| Intermediate | R³ | * | R⁴ | R⁵ | MS (M + 1) |
|---|---|---|---|---|---|
| 204 | 4-Cl-Bn | R | C(O)C(Me)₃ | c-Hex | 520 |
| 205 | 4-Cl-Bn | R | C(O)OMe | c-Hex | 494 |
| 206 | 4-Cl-Bn | R | S(O)₂Me | c-Hex | 515 |
| 207 | 4-Cl-Bn | R | C(O)N(Me)₂ | c-Hex | 507 |
| 208 | 4-Cl-Bn | R | C(O)CH(Me)₂ | c-Pen | 492 |
| 209 | 4-Cl-Bn | R | C(O)CH(Me)₂ | c-Hep | 520 |
| 210 | 4-Cl-Bn | R | C(O)CH(Me)₂ | i-Pr | 466 |
| 211 | 4-Cl-Bn | R | C(O)CH(Me)₂ | i-Bu | 480 |
| 212 | 4-Cl-Bn | R | C(O)CH(Me)₂ | (c-Hex)-CH₂— | 520 |
| 213 | 4-Cl-Bn | R | C(O)CH(Me)₂ | 2-Me-c-Hex | 520 |
| 214 | Bn | R | C(O)CH(Me)₂ | c-Hex | 472 |
| 215 | Bn | R | C(O)CH(Me)₂ | c-Hex | 486 |
| 216 | Bn | R | C(O)C(Me)₃ | c-Hex | 500 |
| 217 | (c-Hex)-CH₂— | R | C(O)CH(Me)₂ | c-Hex | 478 |

Intermediate 218: (2R)-2-(BOC)amino-N-{3-[cyclohexyl(methoxycarbonyl)amino]azetidine-1-yl}-3-(4-chlorophenyl)propionamide The title compound was prepared following the procedure described in Step A of Intermediate 135 using (2R)-2-(BOC)amino-N-[3-(cyclohexylamino)azetidine-1-yl]-3-(4-chlorophenyl)propionamide prepared in Intermediate 202 and methyl bromoacetate.

MS[M+H]=508(M+1)

The present invention is illustrated by the following examples. However, the scopes of the invention are not limited to these examples.

EXAMPLES

Example 1

(2R)-2-amino-N-{(3S)-3-[cyclohexyl(isobutyryl)amino]pyrrolidine-1-yl}-3-(4-chlorophenyl)propionamide.TFA Step A: (2R)-2-(BOC-amino)-N-{(3S)-3-[cyclohexyl(isobutyryl)amino]pyrrolidine-1-yl}-3-(4-chlorophenyl)propionamide To a solution of (3S)-3-[cyclohexyl(isobutyryl)amino]pyrrolidine (HCl salt, 917 mg, 3.30 mmol) in DMF (30 mL) were added DIPEA (1.15 mL, 6.70 mmol), (2R)-N-BOC-(4-chlorophenyl)alanine (1.00 mg, 3.30 mmol), HOBT (668 mg, 5.00 mmol), and EDC (845 mg, 4.30 mmol). After being stirred at rt for 12 h, the reaction solution was concentrated in vacuo, and the residue was diluted with a saturated NaHCO₃ solution and EtOAc. The organic layer was extracted with EtOAc and subsequently washed with a saturated aqueous NaHCO₃ solution, water and an aqueous 1N HCl solution. The organic solution was dried over MgSO₄ and concentrated in vacuo. The residue was purified by column chomatography (eluent: EtOAc/Hex=1/2) to give the title compound (1.58 g, 93.9%).

MS[M+H]=520(M+1)

Step B: (2R)-2-amino-N-{(3R)-3-[cyclohexyl(isobutyryl)amino]pyrrolidine-1-yl}-3-(4-chlorophenyl)propionamide.TFA (2R)-2-(BOC-amino)-N-{(3R)-3-[cyclohexyl(isobutyryl)amino]pyrrolidine-1-yl}-3-(4-chlorophenyl)propionamide, prepared in Step A, (1.00 g, 1.93 mmol) was dissolved in DCM (7 mL), and TFA (7 mL) was added dropwise. After the solution was stirred at rt for 1 h, the solvent was removed in vacuo, and the residue was purified by HPLC to give the title compound (TFA salt, 979 mg, 95.1%).

MS [M+H]=420 (M+1)

Example 2

(2R)-2-{[(2R)-pyrrolidine-2-yl]carbonyl}amino-N-{(3S)-3-[cyclohexyl(isobutyryl)amino]pyrrolidine-1-yl}-3-(4-chlorophenyl)propionamide.2TFA Step A: (2R)-2-{[(2R)-1-(BOC)pyrrolidine-2-yl]carbonyl}amino-N-{(3S)-3-[cyclohexyl(isobutyryl)amino]pyrrolidine-1-yl}-3-(4-chlorophenyl)propionamide To a solution of (2R)-2-amino-N-{(3S)-3-[cyclohexyl(isobutyryl)amino]pyrrolidine-1-yl}-3-(4-chlorophenyl)propionamide TFA, prepared in Example 1, (100 mg, 0.188 mmol) in DMF (3 mL) were added DIPEA (66.1 mL, 0.381 mmol), EDC (48.7 mg, 0.252 mmol), HOBT (43.6 mg, 0.322 mmol), and (2R)-N-BOC-proline (40.9 mg, 0.190 mmol). After the reaction mixture was stirred at rt for 12 h, DMF was removed in vacuo, and the residue was diluted with a saturated aqueous NaHCO₃ solution and EtOAc. The organic layer was extracted with EtOAc and subsequently washed with a saturated aqueous NaHCO$_3$ solution, water and an aqueous 1N HCl solution. The organic solution was dried over MgSO$_4$ and concentrated in vacuo. The residue was purified by column chomatography (eluent: EtOAc/Hex=2/1) to give the title compound (107 g, 90.8%).
MS [M+H]=617 (+1)

Step B: (2R)-2-{[(2R)-pyrrolidine-2-yl]carbonyl}amino-N-{(3S)-3-[cyclohexyl(isobutyryl)amino]pyrrolidine-1-yl}-3-(4-chlorophenyl)propionamide 2TFA To a solution of (2R)-2-{[(2R)-1-(BOC)pyrrolidine-2-yl]carbonyl}amino-N-{(3S)-3-[cyclohexyl(isobutyryl)amino]pyrrolidine-1-yl}-3-(4-chlorophenyl)propionamide, prepared in Step A, (50.0 mg, 0.081 mmol) in DCM (2 mL) was added TFA (2 mL). After the reaction solution was stirred at rt for 30 min. the solvent was removed in vacuo, and the residue was purified by HPLC to give the title compound (50.0 mg, 98.2%).
MS[M+H]=517(M+1)

Example 3

(2R)-2-{[(2R)-pyrrolidine-2-yl]methyl}amino-N-{(3S)-3-[cyclohexyl(isobutyryl)amino]pyrrolidine-1-yl}-3-(4-chlorophenyl)propionamide 2TFA

Step A: (2R)-2-{[(2R)-1-(BOC)pyrrolidine-2-yl]methyl}amino-N-{(3S)-3-[cyclohexyl(isobutyryl)amino]pyrrolidine-1-yl}-3-(4-chlorophenyl)propionamide To a solution of (2R)-2-amino-N-{(3S)-3-[cyclohexyl(isobutyryl)amino]pyrrolidine-1-yl}-3-(4-chlorophenyl)propionamide, prepared in Example 1, (TFA salt, 100 mg, 0.191 mmol) and (2R)-N-BOC-proline carboxyaldehyde (39.6 mg, 0.2 mmol) in DCE (3 mL) was added and NaBH(OAc)$_3$ (96 mg, 4 mmol) at rt. After being stirred 4 h, the reaction mixture was quenched with a saturated aqueous NaHCO$_3$ solution, and the organic material was extracted with DCM followed by EtOAc. The extracts were dried over MgSO$_4$, filtered, and concentrated in vacuo. The residue was purified by column chomatography (eluent: DCM/MeOH=9/1) to give the title compound (107 mg, 90.80%).
MS [M+H]=603 (M+1)

Step B: (2R)-2-{[(2R)-pyrrolidine-2-yl]methyl}amino-N-{(3S)-3-[cyclohexyl(isobutyryl)amino]pyrrolidine-1-yl}-3-(4-chlorophenyl)propionamide 2TFA To a solution of (2R)-2-{[(2R)-1-(BOC)pyrrolidine-2-yl]methyl}amino-N-{(3S)-3-[cyclohexyl(isobutyryl)amino]pyrrolidine-1-yl}-3-(4-chlorophenyl)propionamide(50 mg, 0.0831 mmol), prepared in Step A, in DCM (2 mL) was added TFA (2 mL). After being stirred at rt for 1 h, the reaction solution was concentrated in vacuo, and the residue was purified by HPLC to give the title compound (58.8 mg, 97.1%).
MS[M+H]=517(M+1)

Example 4

(2R)-2-{methyl[((2R)-pyrrolidine-2-yl)methyl]}amino-N-{(3S)-3-[cyclohexyl(isobutyryl)amino]pyrrolidine-1-yl}-3-(4-chlorophenyl)propionamide 2TFA The title compound was prepared following the procedure described in Example 3 using (2R)-2-{[(2R)-1-(BOC)pyrrolidine-2-yl]methyl}amino-N-{(3S)-3-[cyclohexyl(isobutyryl)amino]pyrrolidine-1-yl}-3-(4-chlorophenyl)propionamide prepared in Step B of Example 3 and formaline.
MS[M+H]=531(M+1)

Example 5

(2R)-(dimethyl)amino-N-{(3S)-3-[cyclohexyl(isobutyryl)amino]pyrrolidine-1-yl}-3-(4-chlorophenyl) propionamide 2TFA The title compound was prepared following the procedure described in Example 3 using (2R)-2-amino-N-{(3S)-3-[cyclohexyl(isobutyryl)amino]pyrrolidine-1-yl}-3-(4-chlorophenyl)propionamide TEA prepared in Example 1 and formaline.
MS[M+H]=449(M+1)

Example 6

(2R)-2-[1-(methyl)azetidine-3-yl]amino-N-{(3S)-3-[cyclohexyl(isobutyryl)amino]pyrrolidine-1-yl}-3-(4-chlorophenyl)propionamide 2TFA

Step A: (2R)-2-[1-(BOC)azetidine-3-yl]amino-N-{(3S)-3-[cyclohexyl(isobutyryl)amino]pyrrolidine-1-yl}-3-(4-chlorophenyl)propionamide The title compound was prepared following the procedure described in Step A of Example 3 using (2R)-2-amino-N-{(3S)-3-[cyclohexyl(isobutyryl)amino]pyrrolidine-1-yl}-3-(4-chlorophenyl)propionamide TFA prepared in Example 1 and BOC-3-oxo-azetidine.
MS[M+H]=575(M+1)

Step B: (2R)-2-{Fmoc[1-(BOC)azetidine-3-yl]}amino-N-f{(3S)-3-[cyclohexyl(isobutyryl)amino]pyrrolidine-1-yl}-3-(4-chlorophenyl)propionamide The title compound was prepared following the procedure described in Step A of Intermediate 1 using (2R)-2-[1-(BOC)azetidine-3-yl]amino-N-{(3S)-3-[cyclohexyl(isobutyryl)amino]pyrrolidine-1-yl}-3-(4-chlorophenyl)propionamide prepared Step A.
MS[M+H]=797(M+1)

Step C: (2R)-2-[Fmoc(azetidine-3-yl)]amino-N-{(3S)-3-[cyclohexyl(isobutyryl)amino]pyrrolidine-1-yl}-3-(4-chlorophenyl)propionamide TFA The title compound was prepared following the procedure described in Step B of Example 1 using (2R)-2-{Fmoc[1-(BOC)azetidine-3-yl]}amino-N-{(3S)-3-[cyclohexyl(isobutyryl)amino]pyrrolidine-1-yl}-3-(4-chlorophenyl)propionamide prepared in Step B
MS[M+H]=697(M+1)

Step D: (2R)-2-{Fmoc[1-(methyl)azetidine-3-yl]}amino-N-{(3S)-3-[cyclohexyl(isobutyryl)amino]pyrrolidine-1-yl}-3-(4-chlorophenyl)propionamide The title compound was prepared following the procedure described in Step A of Example 3 using (2R)-2-[Fmoc(azetidine-3-yl)]amino-N-{(3S)-3-[cyclohexyl(isobutyryl)amino]pyrrolidine-1-yl}-3-(4-chlorophenyl)propionamide TFA prepared Step C.
MS[M+H]=711(M+1)

Step E: (2R)-2-[1-(methyl)azetidine-3-yl]amino-N-{(3S)-3-[cyclohexyl(isobutyryl)amino]pyrrolidine-1-yl}-3-(4-chlorophenyl)propionamide 2TFA (2R)-2-{Fmoc[1-(methyl)azetidine-3-yl]}amino-N-{(3S)-3-[cyclohexyl(isobutyryl)amino]pyrrolidine-1-yl}-3-(4-chlorophenyl)propionamide prepared in Step D (71.1 mg, 1 mmol) was dissolved in 50% of piperidine-DMF (2 mL). After being stirred 30 min., the reaction mixture was concentrated in vacuo, and the residue was purified by HPLC to give the title compound (52 mg, 73.5%).

MS[M+H]=489(M+1)

Example 7-186

The compounds below were prepared following the procedure described in Example 1-6 using pyrrolidine, piperidine, or azetidine derivatives prepared in the above Intermediates.

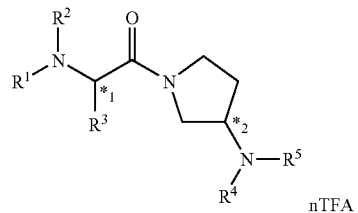

nTFA

| Exm. | $R^1$ | $R^2$ | $R^3$ | *1 | $R^4$ | *2 | $R^5$ | n | MS (M + 1) |
|---|---|---|---|---|---|---|---|---|---|
| 7 | H | H | 4-Cl-Bn | R | c-Hex | S | C(O)C(Me)$_3$ | 1 | 434 |
| 8 | H | H | 4-Cl-Bn | R | c-Hex | S | C(O)OMe | 1 | 408 |
| 9 | H | H | 4-Cl-Bn | R | c-Hex | S | C(O)N(Me)$_2$ | 1 | 421 |
| 10 | H | H | 4-Cl-Bn | R | c-Hex | S | SO$_2$Me | 1 | 428 |
| 11 | H | H | 4-Cl-Bn | R | c-Hex | S | CH$_2$C(O)OMe | 1 | 422 |
| 12 | H | H | 4-Cl-Bn | R | c-Hex | S | SO$_2$NH$_2$ | 1 | 429 |
| 13 | H | H | 4-Cl-Bn | R | c-Hex | S | Gly | 2 | 409 |
| 14 | H | H | 4-Cl-Bn | R | c-Hex | S | CH$_2$C(O)N(Me)$_2$ | 2 | 435 |
| 15 | H | H | 4-Cl-Bn | R | c-Hex | S | CH$_2$SO$_2$Me | 1 | 442 |
| 16 | H | H | 4-Cl-Bn | R | c-Hex | R | C(O)CH(Me)$_2$ | 1 | 420 |
| 17 | H | H | 4-Cl-Bn | R | c-Hex | R | C(O)C(Me)$_3$ | 1 | 434 |
| 18 | H | H | 4-Cl-Bn | R | c-Pen | S | C(O)CH(Me)$_2$ | 1 | 406 |
| 19 | H | H | 4-Cl-Bn | R | c-Hep | S | C(O)CH(Me)$_2$ | 1 | 434 |
| 20 | H | H | 4-Cl-Bn | R | i-Pr | S | C(O)CH(Me)$_2$ | 1 | 480 |
| 21 | H | H | 4-Cl-Bn | R | (c-Hex)-CH$_2$ | S | C(O)CH(Me)$_2$ | 1 | 434 |
| 22 | H | H | 4-Cl-Bn | R | 4,4-diMe-c-Hex | S | C(O)CH(Me)$_2$ | 1 | 448 |
| 23 | H | H | 4-Cl-Bn | R | c-Pen | R | C(O)CH(Me)$_2$ | 1 | 406 |
| 24 | H | H | 4-Cl-Bn | S | c-Hex | S | C(O)CH(Me)$_2$ | 1 | 420 |
| 25 | H | H | Bn | R | c-Hex | S | C(O)CH(Me)$_2$ | 1 | 386 |
| 26 | H | H | 4-Br-Bn | R | c-Hex | S | C(O)CH(Me)$_2$ | 1 | 465 |
| 27 | H | H | 4-MeO-Bn | R | c-Hex | S | C(O)CH(Me)$_2$ | 1 | 416 |
| 28 | H | H | 3,4-diCl-Bn | R | c-Hex | S | C(O)CH(Me)$_2$ | 1 | 454 |
| 29 | H | H | 4-F-Bn | R | c-Hex | S | C(O)CH(Me)$_2$ | 1 | 404 |
| 30 | H | H | 4-HO-Bn | R | c-Hex | S | C(O)CH(Me)$_2$ | 1 | 402 |
| 31 | H | H | (c-Hex)-CH$_2$ | R | c-Hex | S | C(O)CH(Me)$_2$ | 1 | 392 |
| 32 | H | H | (indol-2-yl)-CH$_2$ | R | c-Hex | S | C(O)CH(Me)$_2$ | 2 | 425 |
| 33 | H | H | i-Bu | R | c-Hex | S | C(O)CH(Me)$_2$ | 1 | 352 |
| 34 | H | H | NH$_2$C(O)CH$_2$ | R | c-Hex | S | C(O)CH(Me)$_2$ | 1 | 353 |
| 35 | H | H | 4-Cl-Bn | R | 2,3-diF—Ph | S | C(O)CH(Me)$_2$ | 1 | 450 |
| 36 | H | H | 4-Cl-Bn | R | 2,4-diF—Ph | S | C(O)CH(Me)$_2$ | 1 | 450 |
| 37 | H | H | 4-Cl-Bn | R | 2,3-diF—Ph | R | C(O)CH(Me)$_2$ | 1 | 450 |
| 38 | H | H | 4-Cl-Bn | R | 2,4-diF—Ph | R | C(O)CH(Me)$_2$ | 1 | 450 |
| 39 | Me | Me | 4-Cl-Bn | R | c-Hex | S | C(O)C(Me)$_3$ | 1 | 465 |
| 40 | Ac | H | 4-Cl-Bn | R | c-Hex | S | C(O)CH(Me)$_2$ | 0 | 462 |
| 41 | MeSO$_2$ | H | 4-Cl-Bn | R | c-Hex | S | C(O)CH(Me)$_2$ | 0 | 498 |
| 42 | (Me)$_2$NC(O)—CH$_2$ | H | 4-Cl-Bn | R | c-Hex | S | C(O)CH(Me)$_2$ | 1 | 505 |
| 43 | Gly | H | 4-Cl-Bn | R | c-Hex | S | C(O)CH(Me)$_2$ | 1 | 477 |
| 44 | H$_2$NC(O)—CH$_2$ | H | 4-Cl-Bn | R | c-Hex | S | C(O)CH(Me)$_2$ | 1 | 477 |
| 45 | N-diMe-Gly | H | 4-Cl-Bn | R | c-Hex | S | C(O)CH(Me)$_2$ | 1 | 505 |
| 46 | N-Ac-Gly | H | 4-Cl-Bn | R | c-Hex | S | C(O)CH(Me)$_2$ | 0 | 519 |
| 47 | N-Ms-Gly | H | 4-Cl-Bn | R | c-Hex | S | C(O)CH(Me)$_2$ | 0 | 555 |
| 48 | (R)Ala | H | 4-Cl-Bn | R | c-Hex | S | C(O)CH(Me)$_2$ | 1 | 491 |
| 49 | β-Ala | H | 4-Cl-Bn | R | c-Hex | S | C(O)CH(Me)$_2$ | 1 | 491 |
| 50 | β-Ala | H | 4-Cl-Bn | R | c-Hex | S | C(O)C(Me)$_3$ | 1 | 505 |
| 51 | N-diMe-β-Ala | H | 4-Cl-Bn | R | c-Hex | S | C(O)CH(Me)$_2$ | 1 | 533 |
| 52 | 4-amino-Bu | H | 4-Cl-Bn | R | c-Hex | S | C(O)CH(Me)$_2$ | 0 | 505 |
| 53 | (S)Ala | H | 4-Cl-Bn | R | c-Hex | S | C(O)CH(Me)$_2$ | 1 | 491 |
| 54 | (S)His | H | 4-Cl-Bn | R | c-Hex | S | C(O)CH(Me)$_2$ | 2 | 606 |
| 55 | N—Me-(S)His | H | 4-Cl-Bn | R | c-Hex | S | C(O)CH(Me)$_2$ | 2 | 620 |
| 56 | N—Ac-(S)His | H | 4-Cl-Bn | R | c-Hex | S | C(O)CH(Me)$_2$ | 1 | 648 |
| 57 | N—Ac-(S)His | H | 4-Cl-Bn | R | c-Hex | S | C(O)C(Me)$_3$ | 1 | 662 |
| 58 | N—Ms-(S)His | H | 4-Cl-Bn | R | c-Hex | S | C(O)CH(Me)$_2$ | 1 | 684 |
| 59 | (R)His | H | 4-Cl-Bn | R | c-Hex | S | C(O)CH(Me)$_2$ | 2 | 606 |
| 60 | (S)Phe | H | 4-Cl-Bn | R | c-Hex | S | C(O)CH(Me)$_2$ | 1 | 567 |
| 61 | (R)Phe | H | 4-Cl-Bn | R | c-Hex | S | C(O)CH(Me)$_2$ | 1 | 567 |

-continued

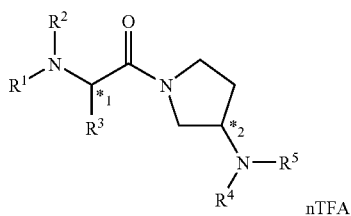
nTFA

| Exm. | R¹ | R² | R³ | *1 | R⁴ | *2 | R⁵ | n | MS (M + 1) |
|---|---|---|---|---|---|---|---|---|---|
| 62 | (R)Pro | H | 4-Cl-Bn | R | c-Hex | S | C(O)C(Me)₃ | 1 | 531 |
| 63 | N—Me-(R)Pro | H | 4-Cl-Bn | R | c-Hex | S | C(O)C(Me)₃ | 1 | 545 |
| 64 | (S)Pro | H | 4-Cl-Bn | R | c-Hex | S | C(O)CH(Me)₂ | 1 | 517 |
| 65 | (R)Pid-2-CO | H | 4-Cl-Bn | R | c-Hex | S | C(O)CH(Me)₂ | 1 | 531 |
| 66 | (R)Pid-2-CO | H | 4-Cl-Bn | R | c-Hex | S | C(O)C(Me)₃ | 1 | 545 |
| 67 | 1-Me-(R)Pid-2-CO | H | 4-Cl-Bn | R | c-Hex | S | C(O)CH(Me)₂ | 1 | 545 |
| 68 | 1-Ac-(R)Pid-2-CO | H | 4-Cl-Bn | R | c-Hex | S | C(O)CH(Me)₂ | 0 | 573 |
| 69 | (S)Pid-2-CO | H | 4-Cl-Bn | R | c-Hex | S | C(O)CH(Me)₂ | 1 | 531 |
| 70 | (R)Tic | H | 4-Cl-Bn | R | c-Hex | S | C(O)CH(Me)₂ | 1 | 579 |
| 71 | (R)Tic | H | Bn | R | c-Hex | S | C(O)CH(Me)₂ | 1 | 545 |
| 72 | (S)Tic | H | 4-Cl-Bn | R | c-Hex | R | C(O)CH(Me)₂ | 1 | 579 |
| 73 | cis-Dic | H | 4-Cl-Bn | R | c-Hex | S | C(O)CH(Me)₂ | 1 | 583 |
| 74 | ![structure] | H | 4-Cl-Bn | R | c-Hex | S | C(O)CH(Me)₂ | 1 | 503 |
| 75 | ![structure] | H | 4-Cl-Bn | R | c-Hex | S | C(O)CH(Me)₂ | 1 | 545 |
| 76 | ![structure] | H | 4-Cl-Bn | R | c-Hex | S | C(O)CH(Me)₂ | 2 | 570 |
| 77 | ![structure] | H | 4-Cl-Bn | R | c-Hex | S | C(O)CH(Me)₂ | 2 | 574 |
| 78 | ![structure] | H | 4-Cl-Bn | R | c-Hex | S | C(O)CH(Me)₂ | 2 | 546 |

-continued

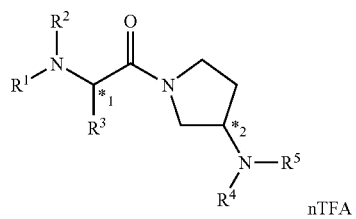

nTFA

| Exm. | R¹ | R² | R³ | *1 | R⁴ | *2 | R⁵ | n | MS (M + 1) |
|---|---|---|---|---|---|---|---|---|---|
| 79 | (1-methyl-4-amino-piperidine-4-carbonyl) | H | 4-Cl-Bn | R | c-Hex | S | C(O)CH(Me)₂ | 2 | 560 |
| 80 | (tetrahydrofuran-2-yl-methyl) | H | 4-Cl-Bn | R | c-Hex | S | C(O)CH(Me)₂ | 1 | 504 |
| 81 | (piperazine-2-carbonyl) | H | 4-Cl-Bn | R | c-Hex | S | C(O)CH(Me)₂ | 1 | 532 |
| 82 | HO—CH₂—C(O) | H | 4-Cl-Bn | R | c-Hex | S | C(O)CH(Me)₂ | 0 | 478 |
| 83 | (aziridine-2-carbonyl) | H | 4-Cl-Bn | R | c-Hex | S | C(O)CH(Me)₂ | 1 | 489 |
| 84 | (R)Pyd-2-CH₂ | H | 4-Cl-Bn | R | c-Hex | S | C(O)C(Me)₃ | 2 | 517 |
| 85 | (R)Pyd-2-CH₂ | H | 4-Cl-Bn | R | c-Hex | R | C(O)CH(Me)₂ | 2 | 503 |
| 86 | (R)Pyd-2-CH₂ | H | 4-Cl-Bn | R | 2,3-diF—Ph | R | C(O)CH(Me)₂ | 2 | 533 |
| 87 | (R)Pyd-2-CH₂ | H | 4-Cl-Bn | R | 2,4-DiF—Ph | R | C(O)CH(Me)₂ | 2 | 533 |
| 88 | (R)Pyd-2-CH₂ | H | 4-Cl-Bn | R | c-Pen | S | C(O)CH(Me)₂ | 2 | 589 |
| 89 | (R)Pyd-2-CH₂ | H | Bn | R | c-Hex | S | C(O)CH(Me)₂ | 2 | 569 |
| 90 | (R)Pyd-2-CH₂ | H | (c-Hex)-CH₂— | R | c-Hex | S | C(O)CH(Me)₂ | 2 | 475 |
| 91 | (R)-1-Ac-Pyd-2-CH₂ | H | 4-Cl-Bn | R | c-Hex | S | C(O)CH(Me)₂ | 1 | 545 |
| 92 | (S)Pyd-2-CH₂ | H | 4-Cl-Bn | R | c-Hex | S | C(O)CH(Me)₂ | 2 | 503 |
| 93 | (S)Pyd-2-CH₂ | Me | 4-Cl-Bn | R | c-Hex | S | C(O)CH(Me)₂ | 2 | 517 |
| 94 | (S)-1-Me-Pyd-2-CH₂ | H | 4-Cl-Bn | R | c-Hex | S | C(O)CH(Me)₂ | 2 | 517 |
| 95 | (R)Pid-2-CH₂ | H | 4-Cl-Bn | R | c-Hex | S | C(O)CH(Me)₂ | 2 | 517 |
| 96 | (R)-1-Me-Pid-2-CH₂ | H | 4-Cl-Bn | R | c-Hex | S | C(O)CH(Me)₂ | 2 | 531 |
| 97 | (R)-1-Me-Pid-2-CH₂ | Me | 4-Cl-Bn | R | c-Hex | S | C(O)CH(Me)₂ | 2 | 559 |
| 98 | (S)Pid-2-CH₂ | H | 4-Cl-Bn | R | c-Hex | S | C(O)CH(Me)₂ | 2 | 517 |
| 99 | (S)-1-Me-Pid-2-CH₂ | H | 4-Cl-Bn | R | c-Hex | S | C(O)CH(Me)₂ | 2 | 531 |
| 100 | (aziridin-2-yl-methyl) | H | 4-Cl-Bn | R | c-Hex | S | C(O)CH(Me)₂ | 2 | 475 |
| 101 | (azetidin-3-yl) | H | 4-Cl-Bn | R | c-Hex | S | C(O)CH(Me)₂ | 2 | 475 |
| 102 | 1-Me-Pid-4-yl | H | 4-Cl-Bn | R | c-Hex | S | C(O)CH(Me)₂ | 2 | 503 |
| 103 | Pid-4-yl | H | 4-Cl-Bn | R | c-Hex | S | C(O)CH(Me)₂ | 2 | 503 |
| 104 | Pid-4-yl | Me | 4-Cl-Bn | R | c-Hex | S | C(O)C(Me)₂ | 2 | 517 |

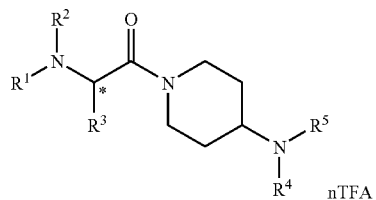

| Exm. | R¹ | R² | R³ | * | R⁴ | R⁵ | n | MS (M+1) |
|---|---|---|---|---|---|---|---|---|
| 105 | H | H | 4-Cl-Bn | R | c-Hex | C(O)CH(Me)$_2$ | 1 | 434 |
| 106 | H | H | 4-Cl-Bn | R | c-Hex | C(O)C(Me)$_3$ | 1 | 448 |
| 107 | H | H | 4-Cl-Bn | R | c-Hex | C(O)OMe | 1 | 422 |
| 108 | H | H | 4-Cl-Bn | R | c-Hex | C(O)N(Me)$_2$ | 1 | 435 |
| 109 | H | H | 4-Cl-Bn | R | c-Hex | CH$_2$C(O)OMe | 2 | 436 |
| 110 | H | H | 4-Cl-Bn | R | c-Hex | Gly | 1 | 423 |
| 111 | H | H | 4-Cl-Bn | R | c-Hex | CH$_2$C(O)N(Me)$_2$ | 2 | 449 |
| 112 | H | H | 4-Cl-Bn | R | c-Hex | C(O)NH(i-Pr) | 1 | 449 |
| 113 | H | H | 4-Cl-Bn | R | c-Hex | C(O)N(i-Pr)(Me) | 1 | 463 |
| 114 | H | H | 4-Cl-Bn | R | c-Hex | C(O)N(Bu) | 1 | 463 |
| 115 | H | H | 4-Cl-Bn | R | c-Hex | C(O)N(Bu)(Me) | 1 | 477 |
| 116 | H | H | 4-Cl-Bn | R | c-Hex | C(O)N(c-Hex) | 1 | 489 |
| 117 | H | H | 4-Cl-Bn | R | c-Hex | C(O)N(Ph) | 1 | 485 |
| 118 | H | H | 4-Cl-Bn | R | c-Hex | C(S)N(Et) | 1 | 451 |
| 119 | H | H | 4-Cl-Bn | R | c-Hex | C(S)N(Et)(Me) | 1 | 465 |
| 120 | H | H | 4-Cl-Bn | R | c-Hex | S(O)$_2$Me | 1 | 456 |
| 121 | H | H | 4-Cl-Bn | R | c-Pen | C(O)CH(Me)$_2$ | 1 | 420 |
| 122 | H | H | 4-Cl-Bn | R | c-Hep | C(O)CH(Me)$_2$ | 1 | 448 |
| 123 | H | H | 4-Cl-Bn | R | ph | C(O)CH(Me)$_2$ | 1 | 428 |
| 124 | H | H | 4-Cl-Bn | R | 2-MeO—Ph | C(O)CH(Me)$_2$ | 1 | 458 |
| 125 | H | H | 4-Cl-Bn | R | 3-MeO—Ph | C(O)CH(Me)$_2$ | 1 | 458 |
| 126 | H | H | 4-Cl-Bn | R | 2-Cl—Ph | C(O)CH(Me)$_2$ | 1 | 462 |
| 127 | H | H | 4-Cl-Bn | R | 2-F—Ph | C(O)CH(Me)$_2$ | 1 | 446 |
| 128 | H | H | 4-Cl-Bn | R | 3-F—Ph | C(O)CH(Me)$_2$ | 1 | 446 |
| 129 | H | H | 4-Cl-Bn | R | 4-F—Ph | C(O)CH(Me)$_2$ | 1 | 446 |
| 130 | H | H | 4-Cl-Bn | R | 2,3-diF—Ph | C(O)CH(Me)$_2$ | 1 | 464 |
| 131 | H | H | 4-Cl-Bn | R | 2,4-diF—Ph | C(O)CH(Me)$_2$ | 1 | 464 |
| 132 | H | H | 4-Cl-Bn | R | 2,5-diF—Ph | C(O)CH(Me)$_2$ | 1 | 464 |
| 133 | H | H | 4-Cl-Bn | R | 2,6-diF—Ph | C(O)CH(Me)$_2$ | 1 | 464 |
| 134 | H | H | 4-Cl-Bn | R | 3,4-diF—Ph | C(O)CH(Me)$_2$ | 1 | 464 |
| 135 | H | H | 4-Cl-Bn | R | 2-F-4-MeO—Ph | C(O)CH(Me)$_2$ | 1 | 476 |
| 136 | H | H | 4-Cl-Bn | S | c-Hex | C(O)CH(Me)$_2$ | 1 | 434 |
| 137 | H | H | 4-Br-Bn | R | c-Hex | C(O)CH(Me)$_2$ | 1 | 479 |
| 138 | H | H | 3,4-di-F-Bn | R | c-Hex | C(O)CH(Me)$_2$ | 1 | 468 |
| 139 | H | H | 3-F-Bn | R | 2,3-diF—Ph | C(O)CH(Me)$_2$ | 1 | 448 |
| 140 | H | H | 4-HO-Bn | R | c-Hex | C(O)CH(Me)$_2$ | 1 | 416 |
| 141 | H | H | 4-MeO-Bn | R | 2,3-diF—Ph | C(O)CH(Me)$_2$ | 1 | 448 |
| 142 | H | H | (c-Hex)-CH$_2$ | R | c-Hex | C(O)CH(Me)$_2$ | 1 | 406 |
| 143 | N-diMe-Gly | H | 4-Cl-Bn | R | c-Hex | C(O)CH(Me)$_2$ | 1 | 519 |
| 144 | (R)Ala | H | 4-Cl-Bn | R | c-Hex | C(O)CH(Me)$_2$ | 1 | 505 |
| 145 | β-Ala | H | 4-Cl-Bn | R | c-Hex | C(O)CH(Me)$_2$ | 1 | 519 |
| 146 | N-diMe-β-Ala | H | 4-Cl-Bn | R | c-Hex | C(O)CH(Me)$_2$ | 1 | 547 |
| 147 | (S)His | H | 4-Cl-Bn | R | c-Hex | C(O)CH(Me)$_2$ | 2 | 620 |
| 148 | (R)Pro | H | 4-Cl-Bn | R | c-Hex | C(O)CH(Me)$_2$ | 1 | 531 |
| 149 | N—Me-(R)Pro | H | 4-Cl-Bn | R | c-Hex | C(O)CH(Me)$_2$ | 1 | 617 |
| 150 | (R)Tic | H | 4-Cl-Bn | R | c-Hex | C(O)CH(Me)$_2$ | 1 | 591 |
| 151 | (R)Pyd-2-CH$_2$ | H | 4-Cl-Bn | R | c-Hex | C(O)CH(Me)$_2$ | 2 | 517 |
| 152 | (R)Pyd-2-CH$_2$ | H | 4-Cl-Bn | R | c-Hex | C(O)C(Me)$_3$ | 2 | 531 |
| 153 | (R)Pyd-2-CH$_2$ | H | 4-Cl-Bn | R | 2,3-diF—Ph | C(O)CH(Me)$_2$ | 2 | 547 |
| 154 | (R)Pyd-2-CH$_2$ | H | 4-Cl-Bn | R | 2,4-diF—Ph | C(O)CH(Me)$_2$ | 2 | 547 |
| 155 | (S)Pyd-2-CH$_2$ | H | 4-F-Bn | R | 2,3-diF—Ph | C(O)CH(Me)$_2$ | 2 | 547 |
| 156 | (2R, 4S)-4F-Pyd-2-CH$_2$ | H | 4-Cl-Bn | R | 2,3-diF—Ph | C(O)CH(Me)$_2$ | 2 | 554 |
| 157 | (S)Pyd-2-CH$_2$ | H | 4-Cl-Bn | R | c-Hex | C(O)CH(Me)$_2$ | 2 | 517 |
| 158 | (S)Pyd-2-CH$_2$ | H | 4-Cl-Bn | R | 2,3-diF—Ph | C(O)CH(Me)$_2$ | 2 | 547 |
| 159 | (S)Pyd-2-CH$_2$ | H | 4-Cl-Bn | R | 2,4-diF—Ph | C(O)CH(Me)$_2$ | 2 | 547 |
| 160 | (R)-1-Me-Pid-2-CH$_2$ | H | 4-Cl-Bn | R | c-Hex | C(O)CH(Me)$_2$ | 2 | 545 |
| 161 | (R)-1-Me-Pid-3-CH$_2$ | H | 4-Cl-Bn | R | c-Hex | C(O)CH(Me)$_2$ | 2 | 545 |

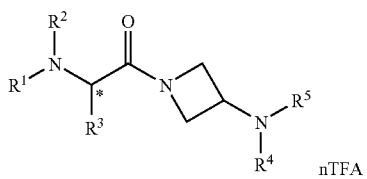

nTFA

| Example | R¹ | R² | R³ | * | R⁴ | R⁵ | n | MS (M + 1) |
|---|---|---|---|---|---|---|---|---|
| 162 | H | H | 4-Cl-Bn |   | c-Hex | C(O)CH(Me)₂ | 1 | 406 |
| 163 | H | H | 4-Cl-Bn |   | c-Hex | C(O)C(Me)₃ | 1 | 420 |
| 164 | H | H | 4-Cl-Bn | R | c-Hex | C(O)OMe | 1 | 394 |
| 165 | H | H | 4-Cl-Bn | R | c-Hex | C(O)N(Me)₂ | 1 | 407 |
| 166 | H | H | 4-Cl-Bn | R | c-Hex | S(O)₂Me | 1 | 414 |
| 167 | H | H | 4-Cl-Bn | R | c-Pen | C(O)CH(Me)₂ | 1 | 392 |
| 168 | H | H | 4-Cl-Bn | R | c-Hep | C(O)CH(Me)₂ | 1 | 420 |
| 169 | H | H | 4-Cl-Bn | R | i-Pr | C(O)CH(Me)₂ | 1 | 466 |
| 170 | H | H | 4-Cl-Bn | R | (c-Hex)-CH₂ | C(O)CH(Me)₂ | 1 | 420 |
| 171 | H | H | 4-Cl-Bn | R | 2-Me-(c-Hex) | C(O)CH(Me)₂ | 1 | 420 |
| 172 | H | H | 4-Cl-Bn | R | i-Bu | C(O)CH(Me)₂ | 1 | 480 |
| 173 | Gly | H | 4-Cl-Bn | R | c-Hex | C(O)CH(Me)₂ | 1 | 463 |
| 174 | N-diMe-Gly | H | 4-Cl-Bn | R | c-Hex | C(O)CH(Me)₂ | 1 | 505 |
| 175 | (S)His | H | 4-Cl-Bn | R | c-Hex | C(O)CH(Me)₂ | 2 | 592 |
| 176 | N—BOC-(S)His | H | 4-Cl-Bn | R | c-Hex | C(O)CH(Me)₂ | 1 | 692 |
| 177 | (R)Pro | H | 4-Cl-Bn | R | c-Hex | C(O)CH(Me)₂ | 1 | 503 |
| 178 | N—Me-(R)Pro | H | 4-Cl-Bn | R | c-Hex | C(O)CH(Me)₂ | 1 | 517 |
| 179 | (S)Pro | H | 4-Cl-Bn | R | c-Hex | C(O)CH(Me)₂ | 1 | 503 |
| 180 | (R)Pid-2-CO | H | 4-Cl-Bn | R | c-Hex | C(O)CH(Me)₂ | 1 | 517 |
| 181 | N—Me-(R)Pid-2-CO | H | 4-Cl-Bn | R | c-Hex | C(O)CH(Me)₂ | 1 | 531 |
| 182 | (R)Tic | H | 4-Cl-Bn | R | c-Hex | C(O)CH(Me)₂ | 1 | 565 |
| 183 | azetidinyl | H | 4-Cl-Bn | R | c-Hex | C(O)CH(Me)₂ | 2 | 489 |
| 184 | (R)Pyd-2-CH₂ | H | 4-Cl-Bn | R | c-Hex | C(O)CH(Me)₂ | 2 | 589 |
| 185 | (R)-1-Me-Pid-2-CH₂ | H | 4-Cl-Bn | R | c-Hex | C(O)CH(Me)₂ | 2 | 631 |
| 186 | (R)Pid-2-CH₂ | H | 4-Cl-Bn | R | c-Hex | C(O)CH(Me)₂ | 2 | 617 |

Example 187

(2R)-2-amino-N-{(3S)-3-{[cyclohexyl((2R)-2-methyl-3-hydroxypropionyl)amino]pyrrolidine-1-yl}-3-(4-chlorophenyl)propionamide HCl

Step A: (2R)-2-(BOC)amino-N-{(3S)-3-[cyclohexyl((2R)-2-methyl-3-acetyloxypropionyl)amino]pyrrolidine-1-yl}-3-(4-chlorophenyl)propionamide The title compound was prepared following the procedure described in Step A of Example 1 using 3(S)-3-{cyclohexyl[(2R)-2-methyl-3-acetyloxypropionyl]amino}pyrrolidine.

MS[M+H]=520(M+1)

Step B: (2R)-2-amino-N-{(3S)-3-[cyclohexyl((2R)-2-methyl-3-acetyloxypropionyl)amino]pyrrolidine-1-yl}-3-(4-chlorophenyl)propionamide TFA To a solution of (2R)-2-(BOC)amino-N-{(3S)-3-[cyclohexyl((2R)-2-methyl-3-acetyloxypropionyl)amino]pyrrolidine-1-yl}-3-(4-chlorophenyl)propionamide, prepared in Step A, in DCM (7 mL) was added TFA (7 mL). After being stirred at rt for 1 h, the reaction mixture was concentrated iii vacuo to give the title compound. The product was used without further purification.

MS[M+1]=420(M+1)

Step C: (2R)-2-amino-N-{(3S)-3-[cyclohexyl((2R)-2-methyl-3-propionyl)amino]pyrrolidine-1-yl}-3-(4-chlorophenyl)propionamide TFA To a solution of (2R)-2-amino-N-{(3S)-3-[cyclohexyl((2R)-2-methyl-3-acetyloxypropionyl)amino]pyrrolidine-1-yl}-3-(4-chlorophenyl)propionamide TFA, prepared in Step B, (592 mg, 1.00 mmol) in MeOH/H₂O=1/1, 10 mL) was added LiOH (70 mg, 2.00 mmol) portionwise. After the reaction mixture was stirred at rt for 30 min., the solvent was removed in vacuo, and the residue was dilute with a saturatd aqueous NaHCO₃ solution. The organic material was extracted with EtOAc, and the extracts were dried over MgSO₄ and concentrated in vacu. The residue was purified by HPLC to give the title compound (495 mg, 90.0%).

MS[M+1]=420(M+1)

Step D: (2R)-2-amino-N-{(3S)-3-[cyclohexyl((2R)-2-methyl-3-hydroxypropionyl)amino]pyrrolidine-1-yl}-3-(4-chlorophenyl)propionamide HCl (2R)-2-amino-N-{(3S)-3-[cyclohexyl((2R)-2-methyl-3-hydroxypropionyl)amino]pyrrolidine-1-yl}-3-(4-chlorophenyl)propionamide TFA prepared in the above Step C was dissolved in methanol, and passed though HCl-substituted ion exchange resin to give the title compound.

MS[M+1]=420(M+1)

Example 188

(2R)-2-(aminoacetyl)amino-N-{(3S)-3-[cyclohexyl((2R)-2-methyl-3-hydroxypropionyl)amino]pyrrolidine-1-yl}-3-(4-chlorophenyl)propionamide HCl Step A: (2R)-2-[(BOC)aminoacetyl]amino-N-{(3S)-3-[cyclohexyl((2R)-2-methyl-3-acetyloxypropionyl)amino]pyrrolidine-1-yl}-3-(4-chlorophenyl)propionamide The title compound was prepared following the procedure described in Step A of Example 1 using (2R)-2-amino-N-{(3S)-3-[cyclohexyl((2R)-2-methyl-3-acetyloxypropionyl)amino]pyrrolidine-1-yl}-3-(4-chlorophenyl)propionamide prepared in Step B of Example 187 and N-BOC-Gly.

MS[M+H]=635(M+1)

Step B: (2R)-2-(aminoacetyl)amino-N-{(3S)-3-[cyclohexyl((2R)-2-methyl-3-acetyloxypropionyl)amino]pyrrolidine-1-yl}-3-(4-chlorophenyl)propionamide TFA The title compound was prepared following the procedure described in Step B of Example 187 using (2R)-2-[(BOC)aminoacetyl]amino-N-{(3S)-3-[cyclohexyl((2R)-2-methyl-3-acetyloxypropionyl)amino]pyrrolidine-1-yl}-3-(4-chlorophenyl)propionamide prepared in Step A.

MS[M+H]=535(M+1)

Step C: (2R)-2-(aminoacetyl)amino-N-{(3S)-3-[cyclohexyl((2R)-2-methyl-3-hydroxypropionyl)amino]pyrrolidine-1-yl}-3-(4-chlorophenyl)propionamide TFA The title compound was prepared following the procedure described in Step C of Example 187 using (2R)-2-(aminoacetyl)amino-N-{(3S)-3-[cyclohexyl((2R)-2-methyl-3-acetyloxypropionyl)amino]pyrrolidine-1-yl}-3-(4-chlorophenyl)propionamide prepared in Step B.

MS[M+H]=493(M+1)

Step D: (2R)-2-(aminoacetyl)amino-N-{(3S)-3-[cyclohexyl((2R)-2-methyl-3-hydroxypropionyl)amino]pyrrolidine-1-yl}-3-(4-chlorophenyl)propionamide HCl The title compound was prepared following the procedure described in Step D of Example 187 using (2R)-2-(aminoacetyl)amino-N-{(3S)-3-[cyclohexyl((2R)-2-methyl-3-hydroxypropionyl)amino]pyrrolidine-1-yl}-3-(4-chlorophenyl)propionamide TFA prepared in Step C.

MS[M+H]=493(M+1)

Example 189

(2R)-2-(dimethyl)amino-N-{(3S)-3-[cyclohexyl((2R)-2-methyl-3-hydroxypropionyl)amino]pyrrolidine-1-yl}-3-(4-chlorophenyl)propionamide HCl Step A: (2R)-2-(dimethyl)amino-N-{(3S)-3-[cyclohexyl((2R)-2-methyl-3-acetyloxypropionyl)amino]pyrrolidine-1-yl}-3-(4-chlorophenyl)propionamide To a solution of (2R)-2-amino-N-{(3S)-3-[cyclohexyl((2R)-2-methyl-3-acetyloxypropionyl)amino]pyrrolidine-1-yl}-3-(4-chlorophenyl)propionamide TFA, prepared in Step B of Example 187, (592 mg, 1.00 mmol) and formaline (0.72 mL, 10.0 mmol) in DCE (3 mL) was added NaBH(OAc)$_3$ (460 mg, 2.00 mmol). After the being stirred at rt for 4 h, the reaction mixture was quenched with an aqueous NaHCO$_3$ solution and extracted with DCM followed by EtOAc. The extracts were dried over MgSO$_4$ and concentrated in vacuo, and the residue was purified by column chomatography (eluent: DCM/MeOH=9/1) to give the title compound (512 mg, 90.0%).

MS[M+H]=563(M+1)

Step B: (2R)-2-(dimethyl)amino-N-{(3S)-3-[cyclohexyl((2R)-2-methyl-3-hydroxypropionyl)amino]pyrrolidine-1-yl}-3-(4-chlorophenyl)propionamide TFA The title compound was prepared following the procedure described in Step C of Example 187 using (2R)-2-(dimethyl)amino-N-{(3S)-3-[cyclohexyl((2R)-2-methyl-3-acetyloxypropionyl)amino]pyrrolidine-1-yl}-3-(4-chlorophenyl)propionamide prepared in the above Step A.

MS[M+H]=521(M+1)

Step C: (2R)-2-(dimethyl)amino-N-{(3S)-3-[cyclohexyl((2R)-2-methyl-3-hydroxypropionyl)amino]pyrrolidine-1-yl}-3-(4-chlorophenyl)propionamide HCl The title compound was prepared following the procedure described in Step D of Example 187 using (2R)-2-(dimethyl)amino-N-{(3S)-3-[cyclohexyl((2R)-2-methyl-3-hydroxypropionyl)amino]pyrrolidine-1-yl}-3-(4-chlorophenyl)propionamide TFA prepared in the above Step B.

MS[M+H]=521(M+1)

Example 190-293

The compounds below were prepared following the procedure described in Example 187-189 using pyrrolidine and piperidine derivatives prepared in the above Intermediates.

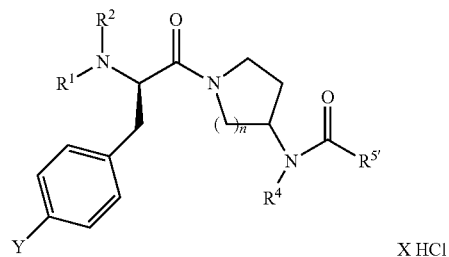

| Exm. | R¹ | R² | Y | R⁴ | R⁵' | * | n | x | MS [M + 1] |
|---|---|---|---|---|---|---|---|---|---|
| 190 | H | H | Cl | c-Hex | C(Me)₂CH₂OH | S | 1 | 1 | 464 |
| 191 | H | H | Cl | c-Hex | C(Me)₂OH | S | 1 | 1 | 436 |
| 192 | H | H | Cl | c-Hex | C(Me)₂(CH₂)₂OH | S | 1 | 1 | 478 |
| 193 | H | H | Cl | c-Hex | C(Me)(CH₂OH)₂ | S | 1 | 1 | 466 |
| 194 | H | H | Cl | c-Hex | C(Me)₂CH₂OH | R | 1 | 1 | 464 |
| 195 | H | H | Cl | c-Hex | C(Me)₂CH₂OMe | S | 1 | 1 | 464 |
| 196 | H | H | Cl | c-Hex | C(Me)₂CH₂OBn | S | 1 | 1 | 540 |
| 197 | H | H | Cl | c-Hex | C(—(CH₂)₄—)CH₂OH | S | 1 | 1 | 464 |
| 198 | H | H | Cl | c-Hex | C(Me)₂(CH₂)₃O-(2,4-diMe—Ph) | S | 1 | 1 | 582 |
| 199 | H | H | Cl | c-Hex | C(Me)CH₂OAc | S | 1 | 1 | 478 |
| 200 | H | H | Cl | c-Hex | C(—(CH₂)₂—)C(O)OH | S | 1 | 1 | 461 |
| 201 | H | H | Cl | c-Hex | N(n-Pr) | S | 1 | 2 | 450 |
| 202 | H | H | Cl | c-Hex | N(Et) | S | 1 | 2 | 436 |
| 203 | H | H | Cl | c-Hex | N(n-Bu) | S | 1 | 2 | 464 |
| 204 | H | H | Cl | c-Hex | 3-OH—Ph | S | 1 | 1 | 470 |
| 205 | H | H | Cl | c-Hex | 4-OH—Ph | S | 1 | 1 | 470 |
| 206 | H | H | Cl | c-Hex | 2-(CH₂OH)-1-(c-penten)-1-yl | S | 1 | 1 | 474 |
| 207 | H | H | Cl | c-Hex | 2-(CH₂OH)-1-(c-Hexen)-1-yl | S | 1 | 1 | 488 |
| 208 | H | H | Cl | c-Hex | 1-Nos-Pid-4-yl | S | 1 | 1 | 646 |
| 209 | H | H | Cl | c-Hex | Pid-4-yl | S | 1 | 2 | 461 |
| 210 | H | H | Cl | c-Hex | C(OH)(i-Pr) | S | 1 | 1 | 449 |
| 211 | H | H | Cl | c-Hex | CH₂C(Me)₂OH | S | 1 | 1 | 449 |
| 212 | H | H | Cl | c-Hex | (cyclopropyl)-CO₂Me | S | 1 | 1 | 475 |
| 213 | H | H | Cl | c-Hex | (cyclopropyl)-OH | S | 1 | 1 | 447 |
| 214 | H | H | H | c-Hex | C(Me)₂CH₂OH | S | 1 | 1 | 415 |
| 215 | H | H | F | c-Hex | C(Me)₂CH₂OH | S | 1 | 1 | 433 |
| 216 | H | H | Me | c-Hex | C(Me)₂CH₂OH | S | 1 | 1 | 429 |
| 217 | H | H | MeO | c-Hex | C(Me)₂CH₂OH | S | 1 | 1 | 445 |
| 218 | Me | Me | Cl | c-Hex | C(Me)₂CH₂OH | S | 1 | 1 | 478 |
| 219 | Me | Me | Cl | c-Hex | C(Me)(CH₂OH)₂ | S | 1 | 1 | 494 |
| 220 | Me | Me | Cl | c-Hex | (methyl-1,3-dioxan-2-one) | S | 1 | 1 | 520 |
| 221 | Me | Me | H | c-Hex | C(Me)₂CH₂OH | S | 1 | 1 | 443 |
| 222 | Me | Me | F | c-Hex | C(Me)₂CH₂OH | S | 1 | 1 | 461 |
| 223 | Me | Me | Me | c-Hex | C(Me)₂CH₂OH | S | 1 | 1 | 457 |
| 224 | Me | Me | MeO | c-Hex | C(Me)₂CH₂OH | S | 1 | 1 | 473 |
| 225 | Et | Et | Cl | c-Hex | C(Me)₂CH₂OH | S | 1 | 1 | 506 |
| 226 | iPr | H | Cl | c-Hex | C(Me)₂CH₂OH | S | 1 | 1 | 492 |
| 227 | —(CH₂)₅— | | Cl | c-Hex | C(Me)₂CH₂OH | S | 1 | 1 | 518 |
| 228 | HOCH₂C(Me)₂C(O) | H | Cl | c-Hex | C(Me)₂CH₂OH | S | 1 | 0 | 550 |
| 229 | Imidazol-2-yl | H | Cl | c-Hex | C(Me)₂CH₂OH | S | 1 | 2 | 530 |
| 230 | Imidazol-4-yl | H | Cl | c-Hex | C(Me)₂CH₂OH | S | 1 | 2 | 530 |
| 231 | (i-Pr)C(O) | H | Cl | c-Hex | C(Me)₂CH₂OH | S | 1 | 0 | 520 |
| 232 | Gly | H | Cl | c-Hex | C(Me)CH₂OH | S | 1 | 1 | 507 |
| 233 | NH₂—(CH₂)₄ | H | Cl | c-Hex | C(Me)CH₂OH | S | 1 | 1 | 535 |
| 234 | N-diMe-Gly | H | Cl | c-Hex | C(Me)₂CH₂OH | S | 1 | 1 | 535 |
| 235 | HO—(CH₂)₃—C(O) | H | Cl | c-Hex | C(Me)₂CH₂OH | S | 1 | 0 | 536 |
| 236 | EtC(O) | H | Cl | c-Hex | C(Me)₂CH₂OH | S | 1 | 0 | 506 |
| 237 | Pyd-3-yl | H | Cl | c-Hex | C(Me)₂CH₂OH | S | 1 | 2 | 519 |
| 238 | (S)Pyd-2-CH₂— | H | Cl | c-Hex | C(Me)₂CH₂OH | S | 1 | 2 | 533 |
| 239 | MeOC(O)CH₂ | H | Cl | c-Hex | C(Me)₂CH₂OH | S | 1 | 0 | 522 |
| 240 | DTic | H | Cl | c-Hex | C(Me)₂CH₂OH | S | 1 | 1 | 609 |

-continued

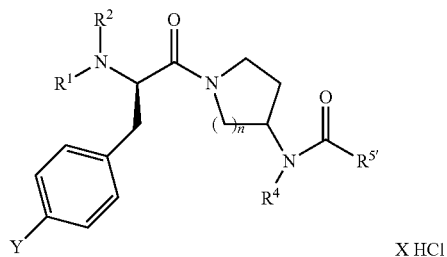

X HCl

| Exm. | R¹ | R² | Y | R⁴ | R⁵' | * | n | x | MS [M + 1] |
|---|---|---|---|---|---|---|---|---|---|
| 241 | NH₂—(CH₂)₂ | H | Cl | c-Hex | C(Me)₂CH₂OH | S | 1 | 2 | 493 |
| 242 | (Me)NH—(CH₂)₂ | H | Cl | c-Hex | C(Me)₂CH₂OH | S | 1 | 2 | 507 |
| 243 | Pyd-2-CH₂— | H | Cl | c-Hex | 2-(CH₂OH)-1-(c-Penen)-1-yl | S | 1 | 2 | 557 |
| 244 | H | H | Cl | 4-cis-Me-c-Hex | C(Me)₂CH₂OH | S | 1 | 1 | 464 |
| 245 | H | H | Cl | 4-trans-Me-c-Hex | C(Me)₂CH₂OH | S | 1 | 1 | 464 |
| 246 | H | H | Cl | 4-t-Bu-c-Hex | C(Me)₂CH₂OH | S | 1 | 1 | 506 |
| 247 | H | H | Cl | 4-Ph-c-Hex | C(Me)₂CH₂OH | S | 1 | 1 | 526 |
| 248 | H | H | Cl | 4,4-diMe-c-Hex | C(Me)₂CH₂OH | S | 1 | 1 | 478 |
| 249 | H | H | Cl | Pid-4-yl | C(Me)₂CH₂OH | S | 1 | 2 | 451 |
| 250 | H | H | Cl | 4-oxo-c-Hex | C(Me)₂CH₂OH | S | 1 | 1 | 464 |
| 251 | H | H | Cl | 4,4-diF-c-Hex | C(Me)₂CH₂OH | S | 1 | 1 | 486 |
| 252 | H | H | Cl | 4-OH-c-Hex | C(Me)₂CH₂OH | S | 1 | 1 | 466 |
| 253 | H | H | Cl | 4-F-c-Hex | C(Me)₂CH₂OH | S | 1 | 1 | 468 |
| 254 | H | H | Cl | Spiro[2,5]octane | C(Me)₂CH₂OH | S | 1 | 1 | 476 |
| 255 | H | H | Cl | 4-cis-Et-c-Hex | C(Me)₂CH₂OH | S | 1 | 1 | 478 |
| 256 | H | H | Cl | 4-trans-Et-c-Hex | C(Me)₂CH₂OH | S | 1 | 1 | 478 |
| 257 | H | H | Cl | 4-cis-Me-c-Hex | C(Me)(CH₂OH)₂ | S | 1 | 1 | 480 |
| 258 | H | H | Cl | 4-trans-Me-c-Hex | C(Me)(CH₂OH)₂ | S | 1 | 1 | 480 |
| 259 | H | H | Cl | 4,4-diMe-c-Hex | C(Me)(CH₂OH)₂ | S | 1 | 1 | 494 |
| 270 | Me | Me | Cl | 4-cis-Me-c-Hex | C(Me)₂CH₂OH | S | 1 | 1 | 492 |
| 271 | Me | Me | Cl | 4-trans-Me-c-Hex | C(Me)₂CH₂OH | S | 1 | 1 | 492 |
| 272 | Me | Me | Cl | 4-t-Bu-c-Hex | C(Me)₂CH₂OH | S | 1 | 1 | 534 |
| 273 | Me | Me | Cl | 4,4-diMe-c-Hex | C(Me)₂CH₂OH | S | 1 | 1 | 514 |
| 274 | Me | Me | Cl | 4-cis-Et-c-Hex | C(Me)₂CH₂OH | S | 1 | 1 | 506 |
| 275 | Me | Me | Cl | 4-trans-Et-c-Hex | C(Me)₂CH₂OH | S | 1 | 1 | 506 |
| 276 | Me | Me | Cl | 4-cis-Me-c-Hex | C(Me)(CH₂OH)₂ | S | 1 | 1 | 508 |
| 277 | Me | Me | Cl | 4-trans-Me-c-Hex | C(Me)(CH₂OH)₂ | S | 1 | 1 | 508 |
| 278 | Me | Me | Cl | 4,4-diMe-c-Hex | C(Me)(CH₂OH)₂ | S | 1 | 1 | 522 |
| 279 | H | H | Cl | 2,3-diF—Ph | C(Me)₂CH₂OH | S | 1 | 1 | 480 |
| 280 | H | H | Cl | 3,5-DiMe—Ph | C(Me)₂CH₂OH | R,S | 1 | 1 | 472 |
| 281 | H | H | Cl | 2,5-diF—Ph | C(Me)₂CH₂OH | R,S | 1 | 1 | 480 |
| 282 | H | H | Cl | 4-Me—Ph | C(Me)₂CH₂OH | R,S | 1 | 1 | 458 |
| 283 | H | H | Cl | Ph | C(Me)₂CH₂OH | R,S | 1 | 1 | 444 |
| 284 | H | H | Cl | 2-Adamantyl | C(Me)₂CH₂OH | S | 1 | 1 | 472 |
| 285 | H | H | Cl | c-Hex | C(Me)₂CH₂OH | R | 2 | 1 | 464 |
| 286 | H | H | Cl | c-Hex | C(Me)(CH₂OH)₂ | R | 2 | 1 | 479 |
| 287 | H | H | Cl | c-Hex | 2-(CH₂OH)-1-(c-penten)-1-yl | S | 2 | 1 | 488 |
| 288 | H | H | Cl | c-Hex | 2-(CH₂OH)-1-(c-hexen)-1-yl | S | 2 | 1 | 502 |
| 289 | H | H | Cl | 4-cis-Me-c-Hex | C(Me)₂CH₂OH | S | 2 | 2 | 477 |
| 290 | H | H | Cl | 4,4-diMe-c-Hex | C(Me)₂CH₂OH | S | 2 | 2 | 591 |
| 291 | H | H | Cl | 4-trans-Me-c-Hex | C(Me)₂CH₂OH | S | 2 | 2 | 493 |
| 292 | (R)Pyd-2-CH₂— | H | Cl | 2,3-diF—Ph | C(Me)₂CH₂OH | S | 2 | 2 | 576 |
| 293 | (R)Pyd-2-CH₂— | H | Cl | c-Hex | C(Me)₂CH₂OH | S | 2 | 2 | 546 |

Example 294

(2R)-2-[isopropyl(methyl)]amino-N-{(3S)-3-[cyclohexyl(hydroxypivaloyl)amino]pyrrolidine-1-yl}-3-(4-chlorophenyl)propionamide HCl Step A: (2R)-2-[isopropyl(methyl)]amino-N-{(3S)-3-[cyclohexyl(hydroxypivaloyl)amino]pyrrolidine-1-yl}-3-(4-chlorophenyl)propionamide TFA The title compound was prepared following the procedure described in Step A of Example 189 using (2R)-2-(isopropyl)amino-N-{(3S)-3-[cyclohexyl(hydroxypivaloyl)amino]pyrroridine-1-yl}-3-(4-chlorophenyl)propionamide TFA prepared in Example 226 (purified by HPLC).

MS[M+H]=492(M+1)

Step B: (2R)-2-[isopropyl(methyl)]amino-N-{(3S)-3-[cyclohexyl(hydroxypivaloyl)amino]pyrrolidine-1-yl}-3-(4-chlorophenyl)propionamide HCl The title compound was prepared following the procedure described in Step D of Example 187 using (2R)-2-[isopropyl(methyl)]amino-N-{(3S)-3-[cyclohexyl(hydroxypivaloyl)amino]pyrrolidine 1-yl}-3-(4-chlorophenyl)propionamide TFA prepared in Step A.

MS[M+H]=492(M+1)

Example 295

(2R)-2-[(2-hydroxy-2-oxo)ethyl]amino-N-{(3S)-3-[cyclohexyl(hydroxypivaloyl)amino]pyrrolidine-1-yl}-3-(4-chlorophenyl)propionamide HCl Step A: (2R)-2-[(2-hydroxy-2-oxo)ethyl]amino-N-{(3S)-3-[cyclohexyl(acetyloxypivaloyl)amino]pyrrolidine-1-yl}-3-(4-chlorophenyl)propionamide TFA To a solution of (2R)-2-amino-N-{(3S)-3-[cyclohexyl(acetyloxypivaloyl)amino]pyrrolidine-1-yl}-3-(4-chlorophenyl)propionamide, prepared in Example 190, (492 mg, 1.00 mmol) in acetonitrile (5 mL) were added DIEA (0.435 mL, 2.50 mmol) was added dropwise and methylbromoacetate (0.085 mL, 1.00 mmol). After the reaction mixture was stirred at 60° C. for 4 h, the solvent was removed in vacuo, and the residue was diluted with an aqueous $NaHCO_3$ solution. The organic material was extracted with EtOAc, and the extracts were washed with 1N HCl, dried over $MgSO_4$, and concentrated in vacuo to give the title compound. The product was used without further purification.
MS[M+H]=564(M+1)

Step B: (2R)-2-[(2-hydroxy-2-oxo)ethyl]amino-N-{(3S)-3-[cyclohexyl(hydroxypivaloyl)amino]pyrrolidine-1-yl}-3-(4-chlorophenyl)propionamide TFA The title compound was prepared following the procedure described in Step C of Example 187 using (2R)-2-[(2-hydroxy-2-oxo)ethyl]amino-N-{(3S)-3-[cyclohexyl(acetyloxypivaloyl)amino]pyrrolidine-1-yl}-3-(4-chlorophenyl)propionamide TFA prepared in Step A.
MS[M+H]=508(M+1)

Step C: (2R)-2-[(2-hydroxy-2-oxo)ethyl]amino-N-{(3S)-3-[cyclohexyl(hydroxypivaloyl)amino]pyrrolidine-1-yl}-3-(4-chlorophenyl)propionamide HCl The title compound was prepared following the procedure described in Step D of Example 187 using (2R)-2-[(2-hydroxy-2-oxo)ethyl]amino-N-{(3S)-3-[cyclohexyl(hydroxypivaloyl)amino]pyrrolidine-1-yl}-3-(4-chlorophenyl)propionamide TFA prepared in Step B.
MS[M+H]=508(M+1)

Example 296

(2R)-2-[di(hydroxyacetyl)]amino-N-{(3S)-3-[cyclohexyl(hydroxypivaloyl)amino]pyrrolidine-1-yl}-3-(4-chlorophenyl)propionamide HCl The title compound was prepared following the procedure described in Example 295 using (2R)-2-amino-N-{(3S)-3-[cyclohexyl(acetyloxypivaloyl)amino]pyrrolidine-1-yl}-3-(4-chlorophenyl)propionamide. MS[M+H]=566(M+1)

Example 297

(2R)-2-amino-N-{(3S)-3-[cyclohexyl(4-aminobutylcarbamoyl)amino]pyrrolidine-1-yl}-3-(4-chlorophenyl)propionamide 2HCl Step A: (2R)-2-amino-N-{(3S)-3-[cyclohexyl(4-aminobutylcarbamoyl)amino]pyrrolidine-1-yl}-3-(4-chlorophenyl)propionamide 2TFA The title compound was prepared following the procedure described in Step B of Example 187 using (3S)-3-[cyclohexyl[4-(BOC)aminobutylcarbamoyl]amino]pyrrolidine prepared in Intermediate 159.
MS[M+H]=549(M+1)

Step B: (2R)-2-amino-N-{(3S)-3-[cyclohexyl(4-aminobutylcarbamoyl)amino]pyrrolidine-1-yl}-3-(4-chlorophenyl)propionamide 2HCl The title compound was prepared following the procedure described in Step D of Example 187 using (2R)-2-amino-N-{(3S)-3-[cyclohexyl(4-aminobutylcarbamoyl)amino]pyrrolidine-1-yl}-3-(4-chlorophenyl)propionamide 2TFA prepared in Step A.
MS[M+H]=549(M+1)

Example 298-357

The compounds below were prepared following the procedure described in Example 189 and 297 using pyrrolidine and piperidine derivatives prepared in the above Intermediates.

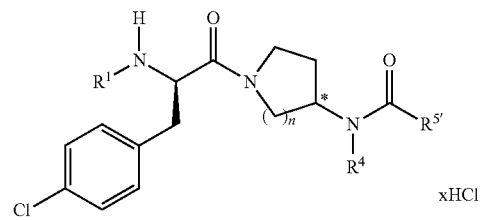

| Exm. | $R^1$ | $R^4$ | $R^{5'}$ | * | n | x | MS [M+1] |
|---|---|---|---|---|---|---|---|
| 298 | H | c-Hex | N—$(CH_2)_3$—$NH_2$ | S | 1 | 2 | 450 |
| 299 | H | c-Hex | N—$(CH_2)_2$—$NH_2$ | S | 1 | 2 | 436 |
| 300 | H | c-Hex | N—$(CH_2)_2$—OH | S | 1 | 1 | 437 |
| 301 | H | c-Hex | N—$(CH_2)_2$—OMe | S | 1 | 1 | 451 |
| 302 | H | c-Hex | (3S)-3-(OH)-Pyd-1-yl | S | 1 | 1 | 463 |
| 303 | H | c-Hex | (2S)-2-($HOCH_2$)-Pyd-1-yl | S | 1 | 1 | 477 |
| 304 | H | c-Hex | N[$(CH_2)_2OH]_2$ | S | 1 | 1 | 495 |
| 305 | H | c-Hex | N[$(CH_2)_3OH]_2$ | S | 1 | 1 | 523 |
| 306 | H | c-Hex | N(Me)$(CH_2)_2$OH | | 2 | 1 | 465 |

-continued

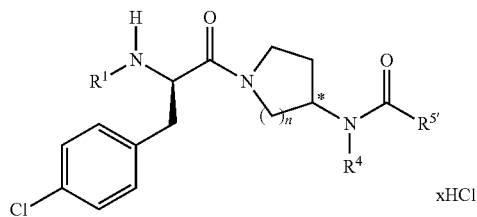

xHCl

| Exm. | R¹ | R⁴ | R⁵' | * | n | x | MS [M + 1] |
|---|---|---|---|---|---|---|---|
| 307 | H | c-Hex | N(Et)(CH₂)₂OH | | 2 | 1 | 479 |
| 308 | H | c-Hex | N(Et)(CH₂)₃OH | | 2 | 1 | 493 |
| 309 | H | c-Hex | N(Et)(CH₂)₂F | | 2 | 1 | 481 |
| 310 | H | c-Hex | N(Et)(CH₂)₃F | | 2 | 1 | 495 |
| 311 | H | c-Hex | N(n-Pr)(CH₂)₂OH | | 2 | 1 | 493 |
| 312 | H | c-Hex | N(c-Pr)(CH₂)₂OH | | 2 | 1 | 491 |
| 313 | H | c-Hex | N(i-Pr)(CH₂)₂OH | | 2 | 1 | 493 |
| 314 | H | c-Hex | N[(CH₂)₂OMe](CH₂)₂OH | | 2 | 1 | 509 |
| 315 | H | c-Hex | N[(CH₂)₂F](CH₂)₂OH | | 2 | 1 | 497 |
| 316 | H | c-Hex | N(Me)(CH₂)₂OMe | | 2 | 1 | 479 |
| 317 | H | c-Hex | N(H)(CH₂)₂OMe | | 2 | 1 | 465 |
| 318 | H | c-Hex | N(Et)(CH₂)₂OMe | | 2 | 1 | 493 |
| 319 | H | c-Hex | N[(CH₂)₂OMe]₂ | | 2 | 1 | 523 |
| 320 | H | c-Hex | N(c-Pen)[(CH₂)₂OMe] | | 2 | 1 | 533 |
| 321 | H | c-Hex | N(Et)₂ | | 2 | 1 | 463 |
| 322 | H | c-Hex | N(Me)OMe | | 2 | 1 | 451 |
| 323 | H | c-Hex | N(Me)[C(O)(Me)₂CH₂OH] | | 2 | 1 | 493 |
| 324 | H | c-Hex | N[(CH₂)₂OMe][(CH₂)₂F] | | 2 | 1 | 511 |
| 325 | H | c-Hex | (3S)-3-(OH)-Pyd-1-yl | | 2 | 1 | 477 |
| 326 | H | c-Hex | (3R)-3-(OH)-Pyd-1-yl | | 2 | 1 | 477 |
| 327 | H | c-Hex | (2R)-2-(HOCH₂)-Pyd-1-yl | | 2 | 1 | 491 |
| 328 | H | c-Hex | (2S)-2-(HOCH₂)-Pyd-1-yl | | 2 | 1 | 491 |
| 329 | H | c-Hex | (3R)-3-amino-Pyd-1-yl | | 2 | 1 | 476 |
| 330 | H | c-Hex | (3S)-3-amino-Pyd-1-yl | | 2 | 1 | 476 |
| 331 | H | c-Hex | (3R)-3-(OH)-Pid-1-yl | | 2 | 1 | 491 |
| 332 | H | c-Hex | (3S)-3-(OH)-Pid-1-yl | | 2 | 1 | 491 |
| 333 | H | c-Hex | 4-(OH)-Pid-1-yl | | 2 | 1 | 491 |
| 334 | H | c-Hex | 4-amino-Pid-1-yl | | 2 | 1 | 490 |
| 335 | (R)Pyd-2-CH₂ | c-Hex | N(n-Pr)(CH₂)₂OH | | 2 | 2 | 576 |
| 336 | (R)Pyd-2-CH₂ | c-Hex | N[(CH₂)₂OH]₂ | | 2 | 2 | 578 |
| 337 | (R)Pyd-2-CH₂ | c-Hex | N(Me)OMe | | 2 | 2 | 534 |
| 338 | (R)Pyd-2-CH₂ | c-Hex | N(Me)[C(Me)₂CH₂OH] | | 2 | 2 | 562 |
| 339 | (R)Pyd-2-CH₂ | c-Hex | N(Et)(CH₂)₂OH | | 2 | 2 | 576 |
| 340 | (R)Pyd-2-CH₂ | c-Hex | N[(CH₂)₂OMe]₂ | | 2 | 2 | 620 |
| 341 | (R)Pyd-2-CH₂ | c-Hex | N(c-Pr)(CH₂)₂OH | | 2 | 2 | 588 |
| 342 | (R)Pyd-2-CH₂ | c-Hex | (3S)-3-(OH)-Pyd-1-yl | | 2 | 2 | 560 |
| 343 | (R)Pyd-2-CH₂ | c-Hex | (2R)-2-(HOCH₂)-Pyd-1-yl | | 2 | 2 | 574 |
| 344 | (R)Pyd-2-CH₂ | c-Hex | 4-(OH)-Pid-1-yl | | 2 | 2 | 574 |
| 345 | (R)Pyd-2-CH₂ | c-Hex | (3R)-3-(OH)-Pid-1-yl | | 2 | 2 | 574 |
| 346 | (S)Pyd-3-yl | c-Hex | N[Et]₂ | | 2 | 2 | 532 |
| 347 | (S)Pyd-3-yl | c-Hex | N(Me)(CH₂)₂OH | | 2 | 2 | 548 |
| 348 | NH₂—(CH₂)₂— | c-Hex | N[(CH₂)₂OH]₂ | | 2 | 2 | 552 |
| 349 | (Me)NH—(CH₂)₂ | c-Hex | N[(CH₂)₂OH]₂ | | 2 | 2 | 566 |
| 350 | (i-Pr)NH—(CH₂)₂— | c-Hex | N(Et)(CH₂)₂OH | | 2 | 2 | 564 |
| 351 | Mor-(CH₂)₂ | c-Hex | N(c-Pr)(CH₂)₂OH | | 2 | 2 | 604 |
| 352 | Mor-(CH₂)₂ | c-Hex | N(Et)(CH₂)₂OH | | 2 | 2 | 592 |
| 353 | Mor-(CH₂)₂ | c-Hex | N[(CH₂)₂OMe]₂ | | 2 | 2 | 636 |
| 354 | H | 2,3-diF—Ph | N(Me)(CH₂)₂OH | | 2 | 1 | 495 |
| 355 | H | 2,3-diF—Ph | N(Me)(CH₂)₂OMe | | 2 | 1 | 495 |
| 356 | (R)Pyd-2-CH₂ | 2,3-diF—Ph | N(Me)(CH₂)₂OH | | 2 | 2 | 578 |
| 357 | (R)Pyd-2-CH₂ | 2,3-diF—Ph | N(Me)(CH₂)₂OMe | | 2 | 2 | 592 |

Example 358

(2R)-2-[2-(dimethylamino)ethyl]amino-N-{(3S)-3-[cyclohexyl(isobutyryl)amino]pyrrolidine-1-yl}-3-(4-chlorophenyl)propionamide 2TFA Step A: (2R)-2-[(2-nitrobenzene)sulfonyl]amino-N-{(3S)-3-[cyclohexyl(isobutyryl)amino]pyrrolidine-1-yl}-3-(4-chlorophenyl)propionamide To a solution of (2R)-2-amino-N-{(3S)-3-[cyclohexyl(isobutyryl)amino]pyrrolidine-1-yl}-3-(4-chlorophenyl)propionamide TFA, prepared in Example 1 (420 mg, 1 mmol), in DMF (10 mL) were added TEA (280 μl, 2 mmol) and (2-nitrobenzene)sulfonylchloride (222 mg, 1.00 mmol). After the being stirred at rt for 4 h, the reaction mixture was quenched with a saturated aqueous NH$_4$Cl solution and was extracted with DCM followed by EtOAc. The extracts were dried over MgSO$_4$, filtered, and concentrated in vacuo. The residue was purified by column chomatography (eluent: EtOAc/Hex=1/3) to give the title compound (568 mg, 94.0%).
MS[M+H]=585(M+1)

Step B: (2R)-2-{(2-nitrobenzene)sulfonyl[2-(dimethylamino)ethyl]}amino-N-{(3S)-3-[cyclohexyl(isobutyryl)amino]pyrrolidine-1-yl}-3-(4-chlorophenyl)propionamide To a solution of (2R)-2-[(2-nitrobenzene)sulfonyl]amino-N-{(3S)-3-[cyclohexyl(isobutyryl)amino]pyrrolidine-1-yl}-3-(4-chlorophenyl)propionamide(200 mg. 0.331 mmol), prepared in Step A, in DMF (3 mL) were added K$_2$CO$_3$ and 2-(dimethylamino)ethyl chloride (HCl salts, 73.9 mg, 0.533 mmol). After being stirred at rt for 24 h, the reaction mixture was concentrated in vacuo, and the residue was diluted a saturated aqueous NH$_4$Cl solution. The organic material was extracted with EtOAc, and the extracts were dried over MgSO$_4$, filtered and concentrated in vacuo. The residue was purified by column chromatography (eluent: EtOAc/Hex=1/1) to give the title compound (205 mg, 92.0%).
MS[M+H]=585(M+1)

Step C: (2R)-2-[2-(dimethylamino)ethyl]amino-N-{(3S)-3-[cyclohexyl(isobutyryl)amino]pyrrolidine-1-yl}-3-(4-chlorophenyl)propionamide 2TFA To a solution of (2R)-2-{(2-nitrobenzene)sulfonyl[2-(dimethylamino)ethyl]}amino-N-{(3S)-3-[cyclohexyl(isobutyryl)amino]pyrrolidine-1-yl}-3-(4-chlorophenyl)propionamide (100 mg, 0.148 mmol), prepared in Step B, in DMF (3 mL) were added K$_2$CO$_3$ (61.3 mg, 0.429 mmol) and thiobenzene (45.6 μl, 0.429 mmol). After being stirred at rt for 2 h, the reaction mixture was concentrated in vacuo to remove DMF, and the residue was diluted with water. The organic material was extracted with EtOAc, and the extracts were dried over MgSO$_4$, filtered and concentrated in vacuo. The residue was purified by HPLC to give the title compound (89 mg, 84.0%).
MS[M+H]=470(M+1)

Example 359

(2R)-2-[2-(methylamino)ethyl]amino-N-{(3S)-3-[cyclohexyl(isobutyryl)amino]pyrrolidine-1-yl}-3-(4-chlorophenyl)propionamide 2TFA Step A: (2R)-2-{(2-nitrobenzene)sulfonyl[2-(BOC)aminoethyl]}amino-N-{(3S)-3-[cyclohexyl(isobutyryl)amino]pyrrolidine-1-yl}-3-(4-chlorophenyl)propionamide The title compound was prepared following the procedure described in Step B of Example 358 using (2R)-2-[(2-nitrobenzene)sulfonyl]amino-N-{(3S)-3-[cyclohexyl(isobutyryl)amino]pyrrolidine-1-yl}-3-(4-chlorophenyl)propionamide prepared in Step A of Example 358 and N-BOC-aminoethylbromide.
MS[M+H]=642(M+1)

Step B: ((2R)-2-{(2-nitroenzene)sulfonyl[2-(methyl(BOC)amino)ethyl]}amino-N-{(3S)-3-[(cyclohexyl(isobutyryl)amino)pyrrolidine-1-yl]-3-(4-chlorophenyl)propionamide The title compound was prepared following the procedure described in Step A of Example 128 using (2R)-2-{(2-nitrobenzene)sulfonyl[2-(BOC)aminoethyl]}amino-N-{(3S)-3-[cyclohexyl(isobutyryl)amino]pyrrolidine-1-yl}-3-(4-chlorophenyl)propionamide prepared in the above Step A and methyliodide.
MS[M+H]=657(M+1)

Step C: (2R)-2-{2-[methyl(BOC)amino]ethyl}amino-N-{(3S)-3-[cyclohexyl(isobutyryl)amino]pyrrolidine-1-yl}-3-(4-chlorophenyl)propionamide The title compound was prepared following the procedure described in Step C of Example 358 using (2R)-2-{[2-BOC(methyl)amino]ethyl(2-nitrobenzenesulfonyl)}amino-N-{(3S)-3-[(cyclohexyl(isobutyryl)amino)pyrrolidine-1-yl]-3-(4-chlorophenyl)propionamide prepared in Step B.
MS[M+H]=657(M+1)

Step D: (2R)-2-[2-(methylamino)ethyl]amino-N-{(3S)-3-[cyclohexyl(isobutyryl)amino]pyrrolidine-1-yl}-3-(4-chlorophenyl)propionamide 2TFA The title compound was prepared following the procedure described in Step B of Example 1 using (2R)-2-{2-[methyl(BOC)amino]ethyl}amino-N-{(3S)-3-[cyclohexyl(isobutyryl)amino]pyrrolidine-1-yl}-3-(4-chlorophenyl)propionamide prepared in Step C.
MS[M+H]=657(M+1)

Example 360

(2R)-2-(2-aminoethyl)amino-N-{(3S)-3-[cyclohexyl(isobutyryl)amino]pyrrolidine-1-yl}-3-(4-chlorophenyl)propionamide 2TFA Step A: (2R)-2-[2-(BOC)aminoethyl]amino-N-{(3S)-3-[cyclohexyl(isobutyryl)amino]pyrrolidine-1-yl}-3-(4-chlorophenyl)propionamide The title compound was prepared following the procedure described in Step C of Example 358 using (2R)-2-{(2-nitrobenzene)sulfonyl[2-(BOC)aminoethyl]}amino-N-{(3S)-3-[cyclohexyl(isobutyryl)amino]pyrrolidine-1-yl}-3-(4-chlorophenyl)propionamide prepared in Step A of Example 359.
MS[M+H]=563(M+1)

Step B: (2R)-2-(2-aminoethyl)amino-N-{(3S)-3-[cyclohexyl(isobutyryl)amino]pyrrolidine-1-yl}-3-(4-chlorophenyl)propionamide 2TFA The title compound was prepared following the procedure described in Step B of Example 1 using (2R)-2-[2-(BOC)

aminoethyl]amino-N-{(3S)-3-[cyclohexyl(isobutyryl)amino]pyrrolidine-1-yl}-3-(4-chlorophenyl)propionamide prepared in Step A.
MS[M+H]=463(M+1)

Example 361

(2R)-2-[2-(acetylamino)ethyl]amino-N-{(3S)-3-[cyclohexyl(isobutyryl)amino]pyrrolidine-1-yl}-3-(4-chlorophenyl)propionamide TFA The title compound was prepared following the procedure described in Example 358 using acetylaminoethyl bromide.
MS[M+H]=505(M+1)

Example 362

(2R)-2-{methyl[2-(methylamino)ethyl]}amino-N-{(3S)-3-[cyclohexyl(isobutyryl)amino]pyrrolidine-1-yl}-3-(4-chlorophenyl)propionamide 2TFA Step A: (2R)-2-{methyl[2-(BOC)aminoethyl]}amino-N-{(3S)-3-[cyclohexyl(isobutyryl)amino]pyrrolidine-1-yl}-3-(4-chlorophenyl)propionamide The title compound was prepared following the procedure described in Step A of Example 3 using (2R)-2-[2-(BOC)aminoethyl]amino-N-{(3S)-3-[cyclohexyl(isobutyryl)amino]pyrrolidine-1-yl}-3-(4-chlorophenyl)propionamide prepared in Step A of Example 360 and formaline.
MS[M+H]=577(M+1)

Step B: (2R)-2-{methyl[2-(methyl(BOC)amino)ethyl]}amino-N-{(3S)-3-[cyclohexyl(isobutyryl)amino]pyrrolidine-1-yl}-3-(4-chlorophenyl)propionamide The title compound was prepared following the procedure described in Step A of Example 128 using (2R)-2-{methyl[2-(BOC)aminoethyl]}amino-N-{(3S)-3-[cyclohexyl(isobutyryl)amino]pyrrolidine-1-yl}-3-(4-chlorophenyl)propionamide prepared in the above Step A and methyliodide.
MS[M+H]=591(M+1)

Step C: (2R)-2-{methyl[2-(methylamino)ethyl]}amino-N-{(3S)-3-[cyclohexyl(isobutyryl)amino]pyrrolidine-1-yl}-3-(4-chlorophenyl)propionamide 2TFA The title compound was prepared following the procedure described in Step B of Example 1 using (2R)-2-{methyl[2-[methyl(BOC)amino]ethyl]}amino-N-{(3S)-3-[cyclohexyl(isobutyryl)amino]pyrrolidine-1-yl}-3-(4-chlorophenyl)propionamide prepared in Step B.
MS[M+H]=491(M+1)

Example 363

(2R)-2-{methyl[2-(amino)ethyl]}amino-N-{(3S)-3-[cyclohexyl(isobutyryl)amino]pyrrolidine-1-yl}-3-(4-chlorophenyl)propionamide 2TFA The title compound was prepared following the procedure described in Step B of Example 1 using (2R)-2-{methyl[2-(BOC)aminoethyl]}amino-N-{(3S)-3-[cyclohexyl(isobutyryl)amino]pyrrolidine-1-yl}-3-(4-chlorophenyl)propionamide prepared in Step A of Example 362.
MS[M+H]=477(M+1)

Example 364

(2R)-2-(methyl)amino-N-{(3S)-3-[cyclohexyl(isobutyryl)amino]pyrrolidine-1-yl}-3-(4-chlorophenyl)propionamide 2TFA Step A: (2R)-2-{methyl[(2-nitrobenzene)sulfonyl]}amino-N-{(3S)-3-[cyclohexyl(isobutyryl)amino]pyrrolidine-1-yl}-3-(4-chlorophenyl)propionamide The title compound was prepared following the procedure described in Step B of Example 358 using (2R)-2-[(2-nitrobenzene)sulfonyl]amino-N-{(3S)-3-[cyclohexyl(isopropyl)amino]pyrrolidine-1-yl}-3-(4-chlorophenyl)propionamide prepared in Step A of Example 358 and methyliodide.
MS[M+H]=619(M+1)

Step B: (2R)-(methyl)amino-N-{(3S)-3-[cyclohexyl(isobutyryl)amino]pyrrolidine-1-yl}-3-(4-chlorophenyl)propionamide TFA The title compound was prepared following the procedure described in Step C of Example 358 using (2R)-2-{methyl[(2-nitrobenzene)sulfonyl]}amino-N-{(3S)-3-[cyclohexyl(isobutyryl)amino]pyrrolidine-1-yl}-3-(4-chlorophenyl)propionamide prepared in Step A.
MS[M+H]=434(M+1)

Example 365-388

The compounds below were prepared following the procedure described in Example 358 and 364 using piperidine derivatives prepared in the above Intermediates.

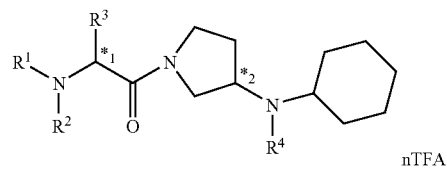

nTFA

| Example | R¹ | R² | R³ | *1 | *2 | R⁴ | n | MS (M + 1) |
|---|---|---|---|---|---|---|---|---|
| 365 | $MeO_2C$—$CH_2$ | H | 4-Cl-Bn | R | S | $C(O)CH(Me)_2$ | 2 | 492 |
| 366 | N-Me-Gly | H | 4-Cl-Bn | R | S | $C(O)CH(Me)_2$ | 1 | 491 |
| 367 | N-Me-β-Ala | H | 4-Cl-Bn | R | S | $C(O)CH(Me)_2$ | 1 | 505 |
| 368 | (Me)NH—$(CH_2)_2$ | H | 4-Cl-Bn | R | R | $C(O)CH(Me)_2$ | 2 | 477 |

-continued

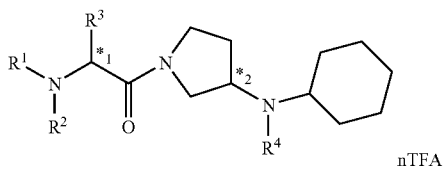

| Example | R¹ | R² | R³ | *1 | *2 | R⁴ | n | MS (M + 1) |
|---|---|---|---|---|---|---|---|---|
| 369 | (Me)₂N—(CH₂)₂ | H | 4-Cl-Bn | R | S | C(O)C(Me)₃ | 2 | 505 |
| 370 | (Me)₂N—(CH₂)₂ | H | Bn | R | S | C(O)CH(Me)₂ | 2 | 457 |
| 371 | (Me)₂N—(CH₂)₂ | H | (c-Hex)-CH₂— | R | S | C(O)CH(Me)₂ | 2 | 463 |
| 372 | (Me)₂N—(CH₂)₂ | Me | 4-Cl-Bn | R | S | C(O)CH(Me)₂ | 2 | 484 |
| 373 | (Et)₂N—(CH₂)₂ | H | 4-Cl-Bn | R | S | C(O)CH(Me)₂ | 2 | 519 |
| 374 | [Me(Et)]N—(CH₂)₂ | H | 4-Cl-Bn | R | S | C(O)CH(Me)₂ | 2 | 505 |
| 375 | (aziridine-1-yl)-(CH₂)₂ | H | 4-Cl-Bn | R | S | C(O)CH(Me)₂ | 2 | 489 |
| 376 | (3R)Pyd-3-yl | H | 4-Cl-Bn | R | S | C(O)CH(Me)₂ | 2 | 489 |
| 377 | (azetidine-2-yl)-CO | H | 4-Cl-Bn | R | S | C(O)CH(Me)₂ | 2 | 503 |
| 378 | Pyd-1-(CH₂)₂ | H | 4-Cl-Bn | R | S | C(O)CH(Me)₂ | 2 | 517 |

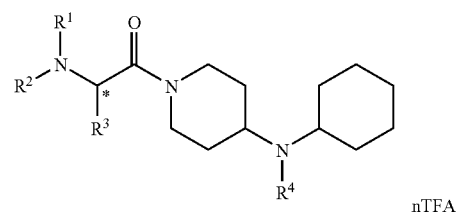

| Example | R¹ | R² | R³ | * | R⁴ | n | MS (M + 1) |
|---|---|---|---|---|---|---|---|
| 379 | Me | H | 4-Cl-Bn | R | C(O)CH(Me)₂ | 1 | 448 |
| 380 | MeO₂C—CH₂ | H | 4-Cl-Bn | R | C(O)CH(Me)₂ | 1 | 506 |
| 381 | NH₂—(CH₂)₂ | H | 4-Cl-Bn | R | C(O)CH(Me)₂ | 2 | 477 |
| 382 | (Me)₂N—(CH₂)₂ | H | 4-Cl-Bn | R | C(O)CH(Me)₂ | 2 | 505 |
| 383 | (3R)Pyd-3-yl | H | 4-Cl-Bn | R | C(O)CH(Me)₂ | 2 | 503 |
| 384 | (3R)Pyd-3-yl | H | Bn | R | C(O)CH(Me)₂ | 2 | 489 |

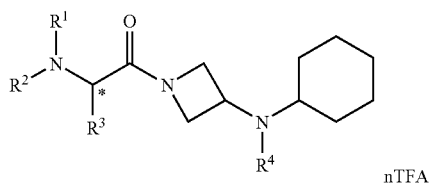

| Example | R¹ | R² | R³ | * | R⁴ | n | MS (M + 1) |
|---|---|---|---|---|---|---|---|
| 385 | MeO₂C—CH₂ | H | 4-Cl-Bn | R | C(O)CH(Me)₂ | 1 | 478 |
| 386 | (Me)₂N—(CH₂)₂ | H | 4-Cl-Bn | R | C(O)CH(Me)₂ | 2 | 505 |
| 387 | (Me)₂N—(CH₂)₂ | H | 4-Cl-Bn | R | C(O)C(Me)₃ | 2 | 519 |
| 388 | Pyd-1-(CH₂)₂ | H | 4-Cl-Bn | R | C(O)CH(Me)₂ | 2 | 503 |

Example 389

(2R)-2-[(dimethylamino)methylene]amino-N-{(3S)-3-{[cyclohexyl(isobutyryl)amino]pyrrolidine-1-yl}-3-(4-chlorophenyl)propionamide TFA (2R)-2-amino-N-{(3S)-3-[cyclohexyl(isobutyryl)amino]pyrrolidine-1-yl}-3-(4-chlorophenyl)propionamide TFA (51.4 mg, 0.1 mmol) and dimethylformamide dimethoxyformat (0.24 mg, 0.2 mmol) were dissolved in methanol (5 mL). After the reaction mixture was stirred at rt for 1 h, the solvent was distilled out in vacuo to remove, the residue was purified by HPLC to give the title compound (46 mg, 99%).

MS[M+H]=477 (M+1)

Example 390

(2R)-2-(carboxymethyl)amino-N-{(3S)-3-{[cyclohexyl(isobutyryl)amino]pyrrolidine-1-yl}-3-(4-chlorophenyl)propionamide TFA The title compound was prepared following the procedure described in Step B of Example 135 using Example 365.
MS[M+H]=478 (M+1)

Example 391

(2R)-2-(carboxymethyl)amino-N-{4-[cyclohexyl(isobutyryl)amino]piperidine-1-yl}-3-(4-chlorophenyl)propionamide TFA The title compound was prepared following the procedure described in Step B of Example 135 using Example 380.
MS[M+H]=492 (M+1)

Example 392

(2R)-2-(carboxymethyl)amino-N-{(3S)-3-[cyclohexyl(isobutyryl)amino]azetidine-1-yl}-3-(4-chlorophenyl)propionamide TFA The title compound was prepared following the procedure described in Step B of Example 135 using Example 385.
MS[M+H]=464 (M+1)

Example 393

(2R)-2-(methyl)amino-N-{(3S)-3-[cyclohexyl(hydroxypivaloyl)amino]pyrrolidine-yl}-3-(4-chlorophenyl)propionamide 2HCl Step A: (2R)-2-[(2-nitrobenzene)sulfonyl]amino-3-(4-chlorophenyl)propionic acid methylester The title compound was prepared following the procedure described in Step C of Example 151 using p-chlorophenylalanine methylester.
MS[M+H]=399(M+1)

Step B: (2R)-2-{[(2-nitrobenzene)sulfonyl]methyl}amino-3-(4-chlorophenyl)propionic acid methylester To a solution of (2R)-2-[(2-nitrobenzene)sulfonyl]amino-3-(4-chlorophenyl)propionic acid methylester (1 g, 2.51 mmol), prepared in Step A, in DMF (10 mL) were added $K_2CO_3$ (678 mg, 5.00 mmol) and methyliodide (427 mg, 3.01 mmol). After the reaction solution was stirred at rt for 12 h, the solvent was concentrated in vacuo, and the residue was diluted with aqueous 1n HCl solution. The organic material was extracted with EtOAc, and the extracts were washed with 1N HCl, dried over $MgSO_4$, and concentrated in vacuo. The residue was purified by column chromatography (eluent: EtOAc:Hex=1/2) to give the title compound (932 mg, 90.0%).
MS[M+H]=413(M+1)

Step C: (2R)-2-{[(2-nitrobenzene)sulfonyl]methyl}amino-3-(4-chlorophenyl)propionic acid The title compound was prepared following the procedure described in Step C of Example 187 using (2R)-2-{[(2-nitrobenzene)sulfonyl]methyl}amino-3-(4-chlorophenyl)propionic acid methyl ester prepared in Step B.
MS[M+H]=399(M+1)

Step D: (2R)-2-{[(2-nitrobenzene)sulfonyl]methyl}amino-N-{(3S)-3-[cyclohexyl(acetyloxypivaloyl)amino]pyrrolidine-1-yl}-3-(4-chlorophenyl)propionamide The title compound was prepared following the procedure described in Step A of Example 188 using (2R)-2-{[(2-nitrobenzene)sulfonyl]methyl}amino-3-(4-chlorophenyl)propionic acid prepared in Step B and (3S)-3-N-[cyclohexyl(acetyloxypivaloyl)amino]pyrrolidine prepared in Intermediate 81.
MS[M+H]=521(M+1)

Step E: (2R)-2-(methyl)amino-N-{(3S)-3-[cyclohexyl(acetyloxypivaloyl)amino]pyrrolidine-1-yl}-3-(4-chlorophenyl)propionamide To a solution of (2R)-2-{[(2-nitrobenzene)sulfonyl]methyl}amino-N-{(3S)-3-[cyclohexyl(acetyloxypivaloyl)amino]pyrrolidine-1-yl}-3-(4-chlorophenyl)propionamide, prepared in Step D, (691 mg, 1.00 mmol) in DMF (5 mL) were added $K_2CO_3$ (270 mg, 2.00 mmol) and mercaptobenzene (0.154 mL, 1.5 mmol), and the mixture was stirred at rt for 2 h. The reaction mixture was concentrated in vacuo and the residue was diluted with aqueous 1N HCl solution. The organic material was extracted with EtOAc, and the extracts were washed with 1N HCl, dried over $MgSO_4$, and concentrated in vacuo to give the title compound. This product was used without further purification.
MS[M+H]=506(M+1)

Step F: (2R)-2-(methyl)amino-N-{(3S)-3-[cyclohexyl(hydroxypivaloyl)amino]pyrrolidine-1-yl}-3-(4-chlorophenyl)propionamide 2TFA The title compound was prepared following the procedure described in Step C of Example 187 using (2R)-2-(methyl)amino-N-{(3S)-3-[cyclohexyl(acetyloxypivaloyl)amino]pyrrolidine-1-yl}-3-(4-chlorophenyl)propionamide prepared in Step E.
MS[M+H]=464(M+1)

Step G: (2R)-2-(methyl)amino-N-{(3S)-3-[cyclohexyl(hydroxypivaloyl)amino]pyrrolidine-1-yl}-3-(4-chlorophenyl)propionamide 2HCl The title compound was prepared following the procedure described in Step D of Example 187 using (2R)-2-(methyl)amino-N-{(3S)-3-[cyclohexyl(hydroxypivaloyl)amino]pyrrolidine-1-yl}-3-(4-chlorophenyl)propionamide 2TFA prepared in Step F.
MS[M+H]=464(M+1)

Example 394

(2R)-2-[2-(dimethylamino)ethyl]amino-N-{(3S)-3-[cyclohexyl(hydroxypivaloyl)amino]pyrrolidine-1-yl}-3-(4-chlorophenyl)propionamide 2HCl Step A: (2R)-2-[(2-nitrobenzene)sulfonyl]amino-N-{(3S)-3-[cyclohexyl(acetyloxypivaloyl)amino]pyrrolidine-1-yl}-3-(4-chlorophenyl)propionamide The title compound was prepared following the procedure described in Step A of Example 358 using (2R)-2-amino-N-

{(3S)-3-[cyclohexyl(acetyloxypivaloyl)amino]pyrrolidine-1-yl}-3-(4-chlorophenyl)propionamide prepared in Example 190 and 2-nitrobenzenesulfonylchloride.
MS[M+H]=677(M+1)

Step B: (2R)-2-{(2-nitrobenzene)sulfonyl[2-(dimethylamino)ethyl]}amino-N-{(3S)-3-[cyclohexyl(acetyloxypivaloyl)amino]pyrrolidine-1-yl}-3-(4-chlorophenyl) propionamide The title compound was prepared following the procedure described in Step B of Example 358 using (2R)-2-[(2-nitrobenzene)sulfonyl]amino-N-{(3S)-3-[cyclohexyl(acetyloxypivaloyl)amino]pyrrolidine-1-yl}-3-(4-chlorophenyl) propionamide prepared in Step A and dimethylaminoethylchloride.
MS[M+H]=748(M+1)

Step C: (2R)-2-[2-(dimethylamino)ethyl]amino-N-{(3S)-3-[cyclohexyl(acetyloxypivaloyl)amino]pyrrolidine-1-yl}-3-(4-chlorophenyl)propionamide The title compound was prepared following the procedure described in Step C of Example 358 using (2R)-2-{(2-nitrobenzene)sulfonyl[2-(dimethylamino)ethyl]}amino-N-{(3S)-3-[cyclohexyl(acetyloxypivaloyl)amino]pyrrolidine-1-yl}-3-(4-chlorophenyl) propionamide prepared in Step B.
MS[M+H]=565(M+1)

Step D: (2R)-2-[2-(dimethylamino)ethyl]amino-N-{(3S)-3-[cyclohexyl(hydroxypivaloyl)amino]pyrrolidine-1-yl}-3-(4-chlorophenyl)propionamide 2TFA The title compound was prepared following the procedure described in Step B of Example 187 using (2R)-2-[2-(dimethylamino)ethyl]amino-N-{(3S)-3-[cyclohexyl(acetyloxypivaloyl)amino]pyrrolidine-1-yl}-3-(4-chlorophenyl) propionamide prepared in Step C.
MS[M+H]=521(M+1)

Step E: (2R)-2-[2-(dimethylamino)ethyl]amino-N-{(3S)-3-[cyclohexyl(hydroxypivaloyl)amino]pyrrolidine-1-yl}-3-(4-chlorophenyl)propionamide 2HCl The title compound was prepared following the procedure described in Step D of Example 187 using (2R)-2-[2-(dimethylamino)ethyl]amino-N-{(3S)-3-[cyclohexyl(hydroxypivaloyl)amino]pyrrolidine-1-yl}-3-(4-chlorophenyl)propionamide 2TFA prepared in Step D.
MS[M+H]=521(M+1)

Example 395-463

The compounds below were prepared following the procedure described in Example 394 using pyrrolidine or piperidine derivatives prepared in the above Intermediates.

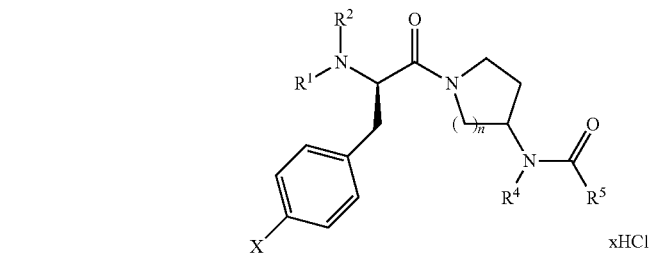

| Exm. | $R^1$ | $R^2$ | X | $R^4$ | $R^{5'}$ | * | n | x | MS [M + 1] |
|---|---|---|---|---|---|---|---|---|---|
| 395 | Me | H | Cl | c-Hex | C(Me)(CH$_2$OH)$_2$ | S | 1 | 1 | 480 |
| 396 | Me | H | Cl | c-Hex | C(Me)$_2$CH$_2$OMe | S | 1 | 1 | 478 |
| 397 | Me | H | Cl | c-Hex | C(Me)$_2$CH$_2$OMOM | S | 1 | 1 | 508 |
| 398 | Me | H | Cl | c-Hex | cyclopropyl-CH$_2$OH | S | 1 | 1 | 462 |
| 399 | Me | H | Cl | 4-cis-Me-c-Hex | C(Me)$_2$CH$_2$OH | S | 1 | 1 | 478 |
| 400 | Me | H | Cl | 4-trans-Me-c-Hex | C(Me)$_2$CH$_2$OH | S | 1 | 1 | 478 |
| 401 | Me | H | Cl | 4-diMe-c-Hex | C(Me)$_2$CH$_2$OH | S | 1 | 1 | 492 |
| 402 | Me | H | Cl | 4-t-Bu-c-Hex | C(Me)$_2$CH$_2$OH | S | 1 | 1 | 520 |
| 403 | Me | H | Cl | 4,4-diF-c-Hex | C(Me)$_2$CH$_2$OH | S | 1 | 1 | 500 |
| 404 | Me | H | Cl | Spiro[2.5]octane | C(Me)$_2$CH$_2$OH | S | 1 | 1 | 490 |
| 405 | Me | H | Cl | 4-F-c-Hex | C(Me)$_2$CH$_2$OH | S | 1 | 1 | 482 |
| 406 | Me | H | Cl | 4-cis-Et-c-Hex | C(Me)$_2$CH$_2$OH | S | 1 | 1 | 492 |
| 407 | Me | H | Cl | 4-trans-Et-c-Hex | C(Me)$_2$CH$_2$OH | S | 1 | 1 | 492 |
| 408 | Me | H | Cl | 4-cis-Me-c-Hex | C(Me)(CH$_2$OH)$_2$ | S | 1 | 1 | 494 |
| 409 | Me | H | Cl | 4-trans-Me-c-Hex | C(Me)(CH$_2$OH)$_2$ | S | 1 | 1 | 494 |
| 410 | Me | H | Cl | 4-diMe-c-Hex | C(Me)(CH$_2$OH)$_2$ | S | 1 | 1 | 508 |
| 411 | Me | H | H | c-Hex | C(Me)$_2$CH$_2$OH | S | 1 | 1 | 430 |
| 412 | Me | H | F | c-Hex | C(Me)$_2$CH$_2$OH | S | 1 | 1 | 448 |
| 413 | Me | H | Me | c-Hex | C(Me)$_2$CH$_2$OH | S | 1 | 1 | 444 |
| 414 | Me | H | OMe | c-Hex | C(Me)$_2$CH$_2$OH | S | 1 | 1 | 460 |
| 415 | i-Pr | H | Cl | 4-cis-Me-c-Hex | C(Me)$_2$CH$_2$OH | S | 1 | 1 | 506 |
| 416 | i-Pr | H | Cl | 4,4-diMe-c-Hex | C(Me)$_2$CH$_2$OH | S | 1 | 1 | 520 |
| 417 | i-Pr | H | Cl | 4,4-diF-c-Hex | C(Me)$_2$CH$_2$OH | S | 1 | 1 | 528 |
| 418 | —(CH$_2$)$_4$— | | Cl | c-Hex | C(Me)$_2$CH$_2$OH | S | 1 | 1 | 520 |

-continued

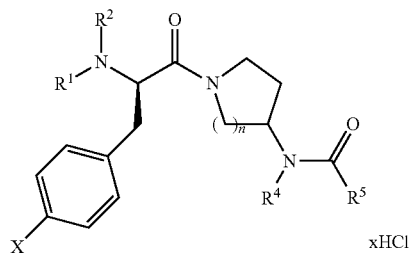

xHCl

| Exm. | R¹ | R² | X | R⁴ | R⁵' | * | n | x | MS [M + 1] |
|---|---|---|---|---|---|---|---|---|---|
| 419 | —(CH₂)₅— | | Cl | c-Hex | C(Me)₂CH₂OH | S | 1 | 1 | 534 |
| 420 | i-Pen | H | Cl | c-Hex | C(Me)₂CH₂OH | S | 1 | 1 | 520 |
| 421 | MeO—(CH₂)₂— | H | Cl | c-Hex | C(Me)₂CH₂OH | S | 1 | 1 | 508 |
| 422 | HO—(CH₂)₂— | H | Cl | c-Hex | C(Me)₂CH₂OH | S | 1 | 1 | 494 |
| 423 | (Me)₂N—(CH₂)₂— | H | Cl | 4-cis-Me-c-Hex | C(Me)₂CH₂OH | S | 1 | 2 | 535 |
| 424 | (Me)₂N—(CH₂)₂— | H | Cl | 4,4-diMe-c-Hex | C(Me)₂CH₂OH | S | 1 | 2 | 549 |
| 425 | (Me)₂N—(CH₂)₂— | H | Cl | c-Hex | C(Me)(CH₂OH)₂ | S | 1 | 2 | 537 |
| 426 | (Me)₂N—(CH₂)₂— | H | Cl | c-Hex | C(Me)₂CH₂N(Me) | S | 1 | 3 | 548 |
| 427 | (Me)₂N—(CH₂)₂— | H | Cl | c-Hex | C(Me)₂CH₂OMe | S | 1 | 2 | 535 |
| 428 | (Me)₂N—(CH₂)₂— | H | Cl | c-Hex | C(Me)₂CH₂OMOM | S | 1 | 2 | 565 |
| 429 | (Me)₂N—(CH₂)₂— | H | Cl | c-Hex | C(Me)₂CH₂OBn | S | 1 | 2 | 611 |
| 430 | (Me)₂N—(CH₂)₂— | H | Cl | c-Hex | C(Me)₂CH₂O(i-Bu) | S | 1 | 2 | 577 |
| 431 | (Me)₂N—(CH₂)₂— | H | Cl | c-Hex | C(Me)₂CH₂OPh | S | 1 | 2 | 597 |
| 432 | (Me)₂N—(CH₂)₂— | H | Cl | c-Hex | C(Me)₂CH₂SPh | S | 1 | 2 | 613 |
| 433 | (Me)₂N—(CH₂)₂— | H | Cl | c-Hex | C(Me)₂CH₂OCOPh | S | 1 | 2 | 625 |
| 434 | (Me)₂N—(CH₂)₂— | H | Cl | c-Hex | C(Me)₂CH₂OCO(c-Hex) | S | 1 | 2 | 631 |
| 435 | (Me)₂N—(CH₂)₂— | H | Cl | c-Hex | C(Me)₂CH₂OCOBn | S | 1 | 2 | 639 |
| 436 | (Me)₂N—(CH₂)₂— | H | Cl | c-Hex | C(Me)₂CH₂OCOBu | S | 1 | 2 | 605 |
| 437 | (Me)₂N—(CH₂)₂— | H | Cl | c-Hex | C(Me)₂CH₂OCO(i-Pr) | S | 1 | 2 | 591 |
| 438 | (Me)₂N—(CH₂)₂— | H | Cl | c-Hex | C(Me)₂CH₂OCO(2,5-diF—Ph) | S | 1 | 2 | 661 |
| 439 | (Me)₂N—(CH₂)₂— | H | Cl | c-Hex | C(Me)₂OAc | S | 1 | 2 | 563 |
| 440 | (Me)₂N—(CH₂)₂— | H | Cl | c-Hex | 2-(HOCH₂)-1-(c-penten)-1-yl | S | 1 | 2 | 545 |
| 441 | (Me)₂N—(CH₂)₂— | H | Cl | c-Hex | (3S)-3-(OH)-Pyd-1-yl | S | 1 | 2 | 534 |
| 442 | (Me)₂N—(CH₂)₂— | H | Cl | 2,3-diF—Ph | C(Me)₂CH₂OH | S | 1 | 2 | 566 |
| 443 | (Me)₂N—(CH₂)₂— | H | Cl | 2,3-diF—Ph | N(Me)₂ | S | 1 | 2 | 580 |
| 444 | (Me)₂N—(CH₂)₂— | H | Cl | c-Hex | N(Me)OMe | | 2 | 2 | 522 |
| 445 | (Me)₂N—(CH₂)₂— | H | Cl | c-Hex | N(Et)(CH₂)₂F | | 2 | 2 | 552 |
| 446 | (Me)₂N—(CH₂)₂— | H | Cl | c-Hex | N(Et)(CH₂)₃F | | 2 | 2 | 566 |
| 447 | (Me)₂N—(CH₂)₂— | H | Cl | c-Hex | N(Et)(CH₂)₃OH | | 2 | 2 | 564 |
| 448 | (Me)₂N—(CH₂)₂— | H | Cl | c-Hex | N(Et)(CH₂)₂OH | | 2 | 2 | 550 |
| 449 | (Me)₂N—(CH₂)₂— | H | Cl | c-Hex | N(n-Pr)(CH₂)₂OH | | 2 | 2 | 564 |
| 450 | (Me)₂N—(CH₂)₂— | H | Cl | c-Hex | N(i-Pr)(CH₂)₂OH | | 2 | 2 | 564 |
| 451 | (Me)₂N—(CH₂)₂— | H | Cl | c-Hex | N[(CH₂)₂OH]₂ | | 2 | 2 | 566 |
| 452 | (Me)₂N—(CH₂)₂— | H | Cl | c-Hex | N[(CH₂)₂OMe]₂ | | 2 | 2 | 594 |
| 453 | (Me)₂N—(CH₂)₂— | H | Cl | c-Hex | (2R)-2-(HOCH₂)-Pyd-1-yl | | 2 | 2 | 562 |
| 454 | (Me)₂N—(CH₂)₂— | H | Cl | c-Hex | 4-amino-Pid-1-yl | | 2 | 2 | 561 |
| 455 | (Me)₂N—(CH₂)₂— | H | Cl | c-Hex | N(Me)(CH₂)₂OH | | 2 | 2 | 536 |
| 456 | (Me)₂N—(CH₂)₂— | H | Cl | c-Hex | N(Me)(CH₂)₂OMe | | 2 | 2 | 550 |
| 457 | (Et)₂N—(CH₂)₂— | H | Cl | c-Hex | N(i-Pr)(CH₂)₂OH | | 2 | 2 | 592 |
| 458 | (Et)₂N—(CH₂)₂— | H | Cl | c-Hex | N(Et)(CH₂)₂OH | | 2 | 2 | 578 |
| 459 | 1-pyd-(CH₂)₂— | H | Cl | c-Hex | N(Et)(CH₂)₂F | | 2 | 2 | 578 |
| 460 | 1-pyd-(CH₂)₂— | H | Cl | c-Hex | N(Et)(CH₂)₃F | | 2 | 2 | 592 |
| 461 | (R)-3-OBn-1-Pyd-(CH₂)₂— | H | Cl | c-Hex | N(Et)(CH₂)₃F | | 2 | 1 | 698 |
| 462 | (R)-3-OBn-1-Pyd-(CH₂)₂— | H | Cl | c-Hex | N(Et)(CH₂)₂OH | | 2 | 1 | 682 |
| 463 | [Me(i-Pr)]N—(CH₂)₂— | H | Cl | c-Hex | N(Et)(CH₂)₃F | | 2 | 2 | 594 |

Example 464

(2R)-2-[2-(dimethylamino)ethyl]amino-N-{(3S)-3-[cyclohexyl((2-formyl)isobutyryl)amino]pyrrolidine-1-yl}-3-(4-chlorophenyl)propionamide 2HCl Step A: (2R)-2-[2-(diethylamino)ethyl]amino-N-{(3S)-3-[cyclohexyl((2-formyl)isobutyryl)amino]pyrrolidine-1-yl}-3-(4-chlorophenyl)propionamide 2TFA To a solution of (2R)-2-[2-(dimethylamino)ethyl]amino-N-{(3S)-3-[cyclohexyl(hydroxypivaloyl)amino]pyrrolidine-1-yl}-3-(4-chlorophenyl)propionamide 2HCl, prepared in Example 394, (521 mg, 1 mmol) in DCM (5 mL) was added Dess-Martin reagent (4M in THF, 0.5 mL). After the reaction mixture was stirred at rt for 12 h, an aqueous Na₂S₂O₃ solution was added portionwise, and the aqueous NaHCO₃ solution was added when the reaction solution is clear. The organic layer was extracted with EtOAc, dried over MgSO₄, and concentrated in vacuo. The residue was purified by prep HPLC to give the title compound (610 mg, 85.1%).

MS[M+H]=519(M+1)

Step B: (2R)-2-[2-(dimethylamino)ethyl]amino-N-{(3S)-3-[cyclohexyl((2-formyl)isobutyryl)amino]pyrrolidine-1-yl}-3-(4-chlorophenyl)propionamide 2HCl The title compound was prepared following the procedure described in Step D of Example 187 using (2R)-2-[2-(dimethylamino)ethyl]amino-N-{(3S)-3-[cyclohexyl((2-formyl)isobutyryl)amino]pyrrolidine-1-yl}-3-(4-chlorophenyl)propionamide 2TFA prepared in Step A.
MS[M+H]=519(M+1)

Example 465

(2R)-2-[2-(dimethylamino)ethyl]amino-N-{(3S)-3-[cyclohexyl((methoxyimino)isobutyryl)amino]pyrrolidine-1-yl}-3-(4-chlorophenyl)propionamide HCl Step A: (2R)-2-[2-(dimethylamino)ethyl]amino-N-{(3S)-3-[cyclohexyl((1-methoxyimino)isobutyryl)amino]pyrrolidine-1-yl}-3-(4-chlorophenyl)propionamide TFA To a solution of (2R)-2-[2-(dimethylamino)ethyl]amino-N-{(3S)-3-[cyclohexyl((2-formyl)isobutyryl)amino]pyrrolidine-1-yl}-3-(4-chlorophenyl)propionamide 2HCl, prepared in Example 464, (704 mg, 1.00 mmol) in pyridine (5 mL) was methoxyamine (HCl salts, 167 mg, 2.00 mmol). After the reaction mixture was stirred at rt for 12 h, the solvent was removed in vacuo, and the residue was diluted with a saturated aqueous NaHCO$_3$ solution. The organic material was extracted with EtOAc, and the extracts were dried over MgSO$_4$ and concentrated in vacuo. The residue was purified by prep HPLC to give the title compound (500 mg, 91.2%).
MS[M+H]=617(M+1)

Step B: (2R)-2-[2-(dimethylamino)ethyl]amino-N-{(3S)-3-[cyclohexyl((1-methoxyimino)isobutyryl)amino]pyrrolidine-1-yl}-3-(4-chlorophenyl)propionamide HCl The title compound was prepared following the procedure described in Step D of Example 187 using (2R)-2-[2-(dimethylamino)ethyl]amino-N-{(3S)-3-[cyclohexyl((1-methoxyimino)isobutyryl)amino]pyrrolidine-1-yl}-3-(4-chlorophenyl)propionamide TFA prepared in Step A.
MS[M+H]=617(M+1)

Biological Assays
A. Binding Assay

The membrane fraction binding assay was used to identify competitive inhibitors of $^{125}$I-NDP--MSH binding to cloned human MCRs expressed in HEK cells.

Cell lines expressing human melanocortin receptor 4 (MC4R) were grown in Φ150 mm culture dishes in DMEM (GIBCO-BRL) supplemented with 10% FBS, 200 ug/ml Geneticin (GIBCO-BRL), and antibiotics (penicillin and streptomycin) (GIBCO-BRL) in an atmosphere of 6% CO$_2$ at 37° C. When the cells were fully grown, the cells were washed once with 10 ml of Ca$^{++}$, Mg$^{++}$ free DPBS. The cells were incubated with 8 ml of Ca$^{++}$, Mg$^{++}$ free DPBS for 15-30 min at 37° C. until the cells were easily detached by triturating with pipette. The cells were harvested into 50 ml of conical tubes, and spun at 1500 rpm for 5 min. The supernatant was discarded, and the cells were resuspended in 8 ml of Ca$^{++}$, Mg$^{++}$ free DPBS, and spun at 1500 rpm for 5 min. The supernatant was discarded, and pellets were resuspended in 3 ml of membrane preparation buffer (50 mM Tris, pH 7.2~7.4, 4 ug/ml Leupeptin; 10 uM Phosphoramidon; 40 ug/ml Bacitracin; 5 ug/ml Aprotinin; 10 mM Pefabloc). The pellets were homogenized with dounce homogenizer (Bellco with type "B" glass pestle) using 10-12 strokes. The homogenate was centrifuged (Beckman XL-100K Ultracentrifuge, Rotor 45 Ti, 50 ml centrifuge tube) at 40,000 rpm (100,000×g) for 30 min at 4° C. The pellets were resuspended in 20 ml of membrane preparation buffer, and protein was determined by BCA assay kit (PIERCE). Aliquots were placed in tubes and stored at −80° C.

Membrane fraction was diluted with membrane binding buffer to make final 600 ug/ml, and 50 ul of membrane fraction containing 30 ug of membrane protein was added onto each well of 96-well assay plate. 25 ul of test compounds or 20 uM unlabelled NDP--MSH (to make the final concentration at 5 uM) diluted with membrane binding buffer was added onto each well of 96-well assay plate. 25 ul of 0.4 nM $^{125}$I-NDP--MSH [NEN, Cat. # NEX352 (50 uCi), $t_{1/2}$=60 days] diluted with membrane binding buffer was added onto each well to make the final concentration of 0.1 nM. The resulting mixture was incubated for 2 h at rt. The reaction mixture was filtered with 96 well GF/C filter plate (Unifilter GF/C™, Packard) presoaked with 0.1% polyethleneimine for 30 min. The filter plate was washed 3 times with 200 ul of washing buffer (50 mM Tris pH 7.2; 20 mM NaCl) under vacuo at 8 "Hg. The filter was dried for 15 min at rt, and the bottom was sealed. 40 ul of Packard Microscint™-20 was added to each well. The top was sealed, and the radioactivity was quantitated in a Packard Topcount Microplate Scintillation Counter. The IC$_{50}$ was defined as the concentration of test compound that results in the half maximal inhibition of $^{125}$I-NDP--MSH binding to cloned human MCRs. The IC$_{50}$ values obtained in the competition assay were converted to affinity constants (Ki values).

B. Functional Assay
1. Luciferase Assay.

Cell lines expressing human melanocortin receptor 4 (MC4R) were dissociated from tissue culture dishes by rinsing with Ca$^{++}$, Mg$^{++}$ free DPBS, treated with 1× Trypsin/EDTA solution for 1 min at 37° C., and resuspended with DMEM (GIBCO-BRL) supplemented with 10% FBS. The cells were counted and diluted with DMEM supplemented with 10% FBS and 200 ug/ml of Geneticin to 5×10$^5$ cells/ml. 90 ul of cell suspension was plated onto each well of 96-well black and clear bottom culture plates (Costar). After the incubation for 24 h in the atmosphere of 6% CO$_2$ at 37° C., 10 ul of NDP--MSH and test compounds diluted in DMSO were added to each well. The final DMSO concentration was 1%. After 4 h of incubation in the atmosphere of 6% CO$_2$ at 37° C., 50 ul of Bright-Glo (Promega) was added to each well. Luciferase activity was measured by using L-Max luminometer (Molecular Device). The amount of luciferase activity induced by treatment with NDP--MSH was defined as 100% to obtain the relative efficacy of test compounds. The EC$_{0.5\ MSH}$ was defined as the concentration of test compounds that results in half maximal activity of NDP--MSH. The EC$_{50}$ was defined as the concentration of test compound that results in half maximal activity of its own.

2. cAMP Accumulation Assay.

The membrane fraction cAMP assay was used to identify MC4R agonist compounds.

Cell lines expressing human melanocortin receptor 4 (MC4R) were grown in Φ150 mm culture dishes in DMEM (GIBCO-BRL) supplemented with 10% FBS, 200 ug/ml Geneticin (GIBCO-BRL), and antibiotics (penicillin and streptomycin) (GIBCO-BRL) in an atmosphere of 6% CO$_2$ at 37° C. When the cells were fully grown, the cells were washed once with 10 ml of $Ca^{++}$, $Mg^{++}$ free DPBS. The cells were incubated with 8 ml of $Ca^{++}$, $Mg^{++}$ free DPBS for 15-30 min at 37° C. until the cells were easily detached by triturating with pipette. The cells were harvested into 50 ml of conical tubes, and spun at 1500 rpm for 5 min. The supernatant was discarded, and the cells were resuspended in 8 ml of $Ca^{++}$, $Mg^{++}$ free DPBS, and spun at 1500 rpm for 5 min. The supernatant was discarded, and the pellets were resuspended in 3 ml of membrane preparation buffer (10 mM Tris pH 7.4; 0.32M sucrose; 4 ug/ml leupeptin; 10 uM phosphoramidon; 40 ug/ml bacitracin; 5 ug/ml aprotinin). The pellets were homogenized with dounce homogenizer (Bellco with type "B" glass pestle) using 20 strokes. The homogenate was centrifuged at 1300×g at 4° C. for 10 min. The supernatants were collected, and the pellets were resuspended in membrane preparation buffer, and homogenization and centrifugation were repeated. All of the supernatants were collected and centrifuged at 40,000 rpm (Beckman XL-100K Ultracentrifuge, Rotor 45 Ti, 50 ml centrifuge tube) at 4° C. for 15 min. The pellets were resuspended in membrane preparation buffer, and protein was determined by BCA assay kit (PIERCE). Aliquots were placed in tubes and stored at −80° C.

20 ul of NDP- -MSH or test compounds diluted in DMSO were added onto each well of 96 well V-plate. 20 ul of 750 ug/ml membrane fraction in MP buffer was added onto each well. After the reaction was performed at rt for 15 min, cAMP was measured using cAMP ($^3$H) assay Kit (Amersham, cat. No. TRK 432). The amount of cAMP produced by the treatment with test compound was compared to that produced in the response to NDP- -MSH which was defined as 100% agonist. The $EC_{50}$ was defined as the concentration of test compound that results in half maximal activity of its own.

As can be seen from the above results, the compounds according to the present invention showed agonistic efficacy and binding affinity to each MCR. In particular, the compounds according to the present invention showed excellent agonistic efficacy and binding affinity to the MCR4. i.e., 0.005 μM-10 μM of $EC_{50}$ value and 0.01 μM-50 μM of $IC_{50}$ value. For example, the compounds of examples 1, 2 and 3 showed 0.005 μM-0.5 μM of $EC_{50}$ value, and 0.1 μM-0.5 μM of $IC_{50}$ value, against MCR4.

C. In Vivo Food Intake Models

1. Hypophasic Effects in Fasted Mice

Hypophasic effects of melanocortinergic ligands are determined by using the food-deprived mouse model (male ddY mice). The animals are individually housed. One day before treatment, the animals are grouped (7-10 animals/group), based on their basal daily food intakes, and then their food is removed for 20 h fasting before treatment. In the morning of the test day, each animal receives the administration of vehicle or test substance via oral gavage, and 1 h after, food is re-supplied. Food intakes after the food-supply are measured for the first 1 h period.

2. Effects on Nocturnal Food Intake

Effects on nocturnal food intake are determined in male ICR mice. The animals are housed individually, and are grouped (7-10 animals/group) based on their basal daily food intakes. Each animal receives the administration of vehicle or test substance via oral gavage 1 h before starting the dark phase, and food is removed. Food is resupplied 1 h after the administration, and food intakes are measured at 1, 2, 4, 8, 24 h after the food is supplied.

3. Effects on Food Intake and Body Weight Change in Ob/Ob Mice

Effects on food intake and body weight change are determined in male 8 wks old ob/ob mice. The animals are housed individually, and are grouped (7-10 animals/group) based on their basal body weights. Each animal receives the administration of vehicle or test substance via oral gavage once a day for 14 days. Food intakes and body weigh changes are measured daily.

4. Effects on Food Intake and Body Weight Change in Diet-Induced Obese (DIO) Mice Effects on food intake and body weight change are determined in male DIO mice. The DIO mice are prepared by feeding C57BL/6 mice on high fat diet for more than 8 weeks. The DIO animals are housed individually, and are grouped (7-10 animals/group) based on their basal body weights. Each animal receives the administration of vehicle or test substance via oral gavage once a day for 14 days. Food intakes and body weigh changes are measured daily.

D. Anti-Inflammatory Effects in an Acute Inflammation Model

Anti-inflammatory effects are determined as the effects on crystal-induced Polymorphonuclear Neutrophil (PMN) rec met. Each Balb/c mouse receives the administration of vehicle or test substance via oral gavage. One hour after the vehicle or drug treatment, the animals receive 3 mg of monosodium urea crystals in 0.5 ml of PBS (H 7.4) buffer (time=0) by the intraperitoneal injection. At 6 hs after the crystal injection, the animals are euthanized by $CO_2$ exposure, and then their peritoneal cavities are washed with 3 ml of PBS buffer. Aliquots of the lavage fluids are stained with Turk's solution (0.01% crystal violet in 3% acetic acid), and the number of cells are counted by using a hemacytometer and a light microscope. PMNs are counted as many as $(1~10)×10^6$ per mouse. Data are presented as $10^6$ PMN per mouse.

E. Erectile Effects

The erectile effect of the test substance is determined by counting the number of erection of male Sprague Dawley rats. Each animal receives the administration of vehicle or test substance via oral gavage 30 min before the test session, and then is placed in a 2-liter glass beaker. The beakers are located on an observation box designed for the ventral view of the animals. The number of erection is counted by observing the posture of the animals (hip constriction, hip thust, tiptoe posture) for 1 h.

The invention claimed is:

1. A compound of the following formula (1):

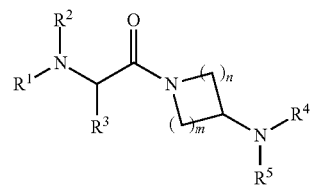

in which m and n each independently represents 2, $R^1$ represents hydrogen;

heterocycle which is selected from the group consisting of morpholine, pyrrolidine, piperidine, furan and tetrahydroisoquinoline ring and which is unsubstituted, or mono- or polysubstituted by substituents selected from halogen and $C_1$-$C_{10}$-alkyl;

—$(CH_2)_{1-3}$—$R^6$, wherein $R^6$ is selected from the group consisting of hydrogen, $C_1$-$C_{10}$-alkyl, $C_1$-$C_8$-alkoxy, heterocycle, hydroxy, $C_1$-$C_8$-alkoxycarbonyl, carboxy, amino, $C_1$-$C_{10}$-alkylamino, di($C_1$-$C_{10}$-alkyl)amino, and $C_1$-$C_8$-alkylcarbonylamino, wherein heterocycle is selected from the group consisting of morpholine, pyrrolidine, piperidine, furan and tetrahydroisoquinoline ring and is substituted by one or more substituents selected from the group consisting of halogen, oxo, hydroxy, $C_1$-$C_{10}$-alkyl, $C_1$-$C_8$-alkylcarbonyl and $C_6$-$C_{10}$-aryloxy;

glycine, alanine, histidine, phenylalanine or proline, wherein one or more hydrogen atoms on nitrogen atom are unsubstituted or substituted by a substituent selected from the group consisting of $C_1$-$C_{10}$-alkyl, $C_1$-$C_8$-alkylcarbonyl, $C_1$-$C_8$-alkoxycarbonyl and $C_1$-$C_8$-alkylsulfonyl; or —$SO_2$—$C_1$-$C_3$-alkyl, $R^2$ represents hydrogen;

$C_1$-$C_8$-alkyl;

—CO—$(CH_2)_{1-3}$-hydroxy; or

—$CH_2$—CO-hydroxy, $R^3$ represents $C_1$-$C_8$-alkyl which is unsubstituted, or mono- or polysubstituted by substituents selected from $C_1$-$C_8$-alkyl and carbamoyl;

—$(CH_2)_{1-3}$—$C_3$-$C_8$-cycloalkyl; or

—$(CH_2)_{0-3}$—$C_6$-$C_{10}$-aryl which is unsubstituted, or mono- or polysubstituted by substituents selected from the group consisting of halogen, hydroxy, $C_1$-$C_8$-alkoxy and $C_1$-$C_8$-alkyl, $R^4$ represents $C_1$-$C_8$-alkyl;

—$(CH_2)_{1-3}$—$C_3$-$C_8$-cycloalkyl;

$C_3$-$C_8$-cycloalkyl which is unsubstituted, or mono- or polysubstituted by substituents selected from the group consisting of halogen, $C_1$-$C_8$-alkyl and $C_6$-$C_{10}$-aryl; or heterocycle which is selected from the group consisting of morpholine, pyrrolidine, piperidine, furan and tetrahydroisoquinoline ring, $R^5$ represents carbonyl substituted by a substituent selected from the group consisting of $C_1$-$C_8$-alkyl, $C_1$-$C_6$ alkoxy, $C_3$-$C_7$-cycloalkyl, heterocycle and $C_6$-$C_{10}$-aryl unsubstituted or substituted by hydroxyl, wherein alkyl is unsubstituted, or mono- or polysubstituted by substituents selected from the group consisting of amino, $C_1$-$C_8$-alkylamino, di($C_1$-$C_8$-alkyl)amino, hydroxy, $C_1$-$C_8$-alkoxy, $C_6$-$C_{10}$-ar-$C_1$-$C_8$-alkyloxy, $C_1$-$C_8$-alkyl $C_6$-$C_{10}$-aryloxy, $C_6$-$C_{10}$-aryloxy, $C_6$-$C_{10}$-arylthio, formyl, $C_2$-$C_8$-alkanoyloxy, $C_3$-$C_8$-cycloalkylcarbonyloxy, $C_6$-$C_{10}$-arylcarbonyloxy unsubstituted or substituted by halogen, $C_6$-$C_{10}$-ar-$C_1$-$C_8$-alkylcarbonyloxy; cycloalkyl is unsubstituted, or mono- or polysubstituted by substituents selected from the group consisting of hydroxycarbonyl, $C_1$-$C_8$-alkoxycarbonyl, hydroxyl-$C_1$-$C_8$alkyl, and wherein heterocycle is selected from the group consisting of morpholine, pyrrolidine, piperidine, furan and tetrahydroisoquinoline ring and is unsubstituted, or mono- or polysubstituted by the substituents selected from the group consisting of hydroxy, hydroxy$C_1$-$C_8$-alkyl, amino and 2-nitrobenzenesulfonyl;

—$(CH_2)_{1-3}$—C(=O)—$C_1$-$C_6$-alkoxy;

carbamoyl which is mono- or polysubstituted by substituents selected from the group consisting of hydrogen, $C_1$-$C_8$-alkyl, $C_1$-$C_6$-alkoxy, $C_3$-$C_7$-cycloalkyl, $C_6$-$C_{10}$-aryl and $C_1$-$C_8$-alkylcarbonyl substituted by hydroxy, wherein alkyl is unsubstituted, or mono- or polysubstituted by substituents selected from the group consisting of halogen, hydroxy, amino and $C_1$-$C_8$-alkoxy;

—$(CH_2)_{1-3}$—C(=O)N($C_1$-$C_8$-alkyl)($C_1$-$C_8$-alkyl);

—C(=S)N(H)($C_1$-$C_8$-alkyl) or —C(=S)N(H)($C_1$-$C_8$-alkyl)($C_1$-$C_8$-alkyl); or —$SO_2$—$NH_2$ or —$(CH_2)_{0-3}$—$SO_2$—$C_1$-$C_8$alkyl, wherein heterocycle can be fused with benzo or $C_3$-$C_8$-cycloalkyl, and which is saturated or has 1 or 2 double bond, or a pharmaceutically acceptable salt, hydrate, or stereoisomer thereof.

2. The compound according to claim 1, wherein $R^1$ represents hydrogen; or

—$(CH_2)_{1-3}$—$R^6$, wherein $R^6$ selected from the group consisting of hydrogen, $C_1$-$C_{10}$-alkyl, $C_1$-$C_8$-alkoxy, heterocycle, hydroxy, $C_1$-$C_8$-alkoxylcarbonyl, carboxy, amino, $C_1$-$C_{10}$-alkylamino, di($C_1$-$C_{10}$-alkyl)amino, and $C_1$-$C_8$-alkylcarbonylamino, wherein heterocycle is selected from the group consisting of morpholine, pyrrolidine, piperidine, furan and tetrahydroisoquinoline ring and is substituted by one or more substituents selected from the group consisting of halogen, oxo, hydroxy, $C_1$-$C_{10}$-alkyl, $C_1$-$C_8$-alkylcarbonyl and $C_6$-$C_{10}$-aryloxy; or a pharmaceutically acceptable salt, hydrate, or stereoisomer thereof.

3. The compound according to claim 1, wherein $R^2$ represents hydrogen or $C_1$-$C_6$-alkyl, or a pharmaceutically acceptable salt, hydrate, or stereoisomer thereof.

4. The compound according to claim 1, wherein $R^3$ represents —$CH_2$-phenyl which is unsubstituted or mono- to tri-substituted by substituents selected from the group consisting of chloro, bromo, hydroxy, methoxy and methyl, or a pharmaceutically acceptable salt, hydrate, or stereoisomer thereof.

5. The compound according to claim 1, wherein $R^4$ represents $C_3$-$C_8$-cycloalkyl which is unsubstituted, or mono- or polysubstituted by substituents selected from the group consisting of halogen, $C_1$-$C_8$-alkyl and $C_6$-$C_{10}$-aryl, or a pharmaceutically acceptable salt, hydrate, or stereoisomer thereof.

6. The compound according to claim 1, wherein $R^5$ represents carbonyl substituted by the substituent selected from the group consisting of $C_1$-$C_8$-alkyl, $C_1$-$C_6$-alkoxy, $C_3$-$C_7$-cycloalkyl, heterocycle and $C_6$-$C_{10}$-aryl unsubstituted or substituted by hydroxyl, wherein alkyl is unsubstituted, or mono- or polysubstituted by the substituents selected from the group consisting of amino, $C_1$-$C_6$-alkylamino, di($C_1$-$C_6$-alkyl) amino, hydroxy, $C_1$-$C_8$-alkoxy, $C_6$-$C_{10}$-ar $C_1$-$C_8$-alkyloxy, $C_1$-$C_8$-alkyl $C_6$-$C_{10}$-aryloxy, $C_6$-$C_{10}$-aryloxy, $C_6$-$C_{10}$-arylthio, formyl, $C_2$-$C_8$-alkanoyloxy, $C_3$-$C_8$-cycloalkylcarbonyloxy, $C_6$-$C_{10}$-arylcarbonyloxy unsubstituted or substituted by halogen, $C_6$-$C_{10}$-ar-$C_1$-$C_8$-alkylcarbonyloxy; cycloalkyl is unsubstituted, or mono- or polysubstituted by substituents selected from the group consisting of hydroxycarbonyl, $C_1$-$C_8$-alkoxycarbonyl, hydroxyl-$C_1$-$C_8$-alkyl, and wherein heterocycle is selected from the group consisting of morpholine, pyrrolidine, piperidine, furan and tetrahydroisoquinoline ring and is unsubstituted, or mono- or polysubstituted by the substituents selected from the group consisting of hydroxy, hydroxyC$_1$-C$_8$-alkyl, amino and 2-nitrobenzenesulfonyl, or a pharmaceutically acceptable salt, hydrate, or stereoisomer thereof.

7. An agonistic composition of melanocortin receptor comprising the compound of formula (1), or a pharmaceutically acceptable salt, hydrate, or stereoisomer thereof as defined in claim 1 together with a pharmaceutically acceptable carrier.

* * * * *